US010537541B2

(12) United States Patent
Jorkasky

(10) Patent No.: US 10,537,541 B2
(45) Date of Patent: Jan. 21, 2020

(54) TREATMENT OF FOCAL SEGMENTAL GLOMERULAR SCLEROSIS (FSGS) USING THERAPEUTICALLY EFFECTIVE ORAL DOSES OF 10-NITRO-9(E)-OCTADEC-9-ENOIC ACID

(71) Applicant: Complexa, Inc., Radnor, PA (US)

(72) Inventor: Diane Jorkasky, Devon, PA (US)

(73) Assignee: Complexa Inc., Berwyn, PA (US)

( * ) Notice: Subject to any disclaimer, the term of this patent is extended or adjusted under 35 U.S.C. 154(b) by 0 days.

(21) Appl. No.: 15/283,887

(22) Filed: Oct. 3, 2016

(65) Prior Publication Data
US 2017/0095437 A1 Apr. 6, 2017

Related U.S. Application Data

(60) Provisional application No. 62/236,702, filed on Oct. 2, 2015.

(51) Int. Cl.
A61K 31/201 (2006.01)
A61P 9/12 (2006.01)
A61P 13/12 (2006.01)
A61P 11/00 (2006.01)

(52) U.S. Cl.
CPC .................. A61K 31/201 (2013.01)

(58) Field of Classification Search
CPC .......... A61K 31/201; A61P 9/12; A61P 13/12; A61P 11/00
USPC ........................................ 514/560
See application file for complete search history.

(56) References Cited

U.S. PATENT DOCUMENTS

| | | | |
|---|---|---|---|
| 3,578,687 A | 5/1971 | Larkin et al. | |
| 3,819,561 A | 6/1974 | Bruenner | |
| 3,917,660 A | 11/1975 | Sasaki et al. | |
| 4,599,430 A | 7/1986 | Milberger et al. | |
| 5,412,137 A | 5/1995 | Prashad | |
| 5,741,211 A | 4/1998 | Renirie et al. | |
| 5,919,816 A | 7/1999 | Hausheer et al. | |
| 6,187,747 B1 | 2/2001 | Singh et al. | |
| 6,262,029 B1 | 7/2001 | Press et al. | |
| 6,346,231 B1 | 2/2002 | Opheim | |
| 6,376,688 B1 | 4/2002 | Ferrante et al. | |
| 6,407,075 B1 | 6/2002 | Scott et al. | |
| 6,410,802 B1 | 6/2002 | Dasseux et al. | |
| 6,531,150 B1 | 3/2003 | Sunohara et al. | |
| 6,652,879 B2 | 11/2003 | Opheim | |
| 6,924,309 B2 | 8/2005 | Ferrante et al. | |
| 6,998,395 B2 | 2/2006 | Jackson et al. | |
| 7,312,191 B2 | 12/2007 | Rose et al. | |
| 7,452,907 B2 | 11/2008 | Cheng et al. | |
| 7,776,916 B2 * | 8/2010 | Freeman ................ | A61K 31/21 514/558 |
| 7,977,315 B2 | 7/2011 | Rose et al. | |
| 8,309,526 B2 * | 11/2012 | Freeman ................ | A61K 31/21 514/25 |
| 8,324,277 B2 | 12/2012 | Freeman et al. | |
| 8,563,609 B2 * | 10/2013 | Miller ..................... | A23L 33/12 424/523 |
| 8,686,038 B2 * | 4/2014 | Yang ..................... | A61K 31/201 514/560 |
| 8,686,167 B2 | 4/2014 | Miller | |
| 8,735,449 B2 | 5/2014 | Freeman | |
| 8,933,255 B2 | 1/2015 | Miller | |
| 8,937,194 B2 | 1/2015 | Miller | |
| 9,006,473 B2 | 4/2015 | Freeman et al. | |
| 9,066,902 B2 | 6/2015 | Freeman et al. | |
| 9,186,408 B2 | 11/2015 | Freeman et al. | |
| 9,192,600 B2 | 11/2015 | Yang | |
| 9,271,952 B2 | 3/2016 | Cushing | |
| 9,295,678 B2 | 3/2016 | Freeman et al. | |
| 9,308,189 B2 | 4/2016 | Miller | |
| 9,522,156 B2 | 12/2016 | Freeman et al. | |
| 9,700,534 B2 | 7/2017 | Freeman | |
| 2001/0037598 A1 | 11/2001 | Suppes et al. | |
| 2002/0128510 A1 | 9/2002 | Durley et al. | |
| 2003/0078299 A1 | 4/2003 | Ferrante et al. | |
| 2004/0006248 A1 | 1/2004 | Paiocchi et al. | |
| 2004/0092590 A1 | 5/2004 | Arterburn et al. | |
| 2004/0147599 A1 | 7/2004 | Gagnon et al. | |
| 2004/0176451 A1 | 9/2004 | Tamai et al. | |
| 2004/0254240 A1 | 12/2004 | Ferrante et al. | |
| 2005/0136103 A1 | 6/2005 | Ben-Sasson et al. | |
| 2005/0232981 A1 | 10/2005 | Ben-Sasson | |
| 2006/0018874 A1 | 1/2006 | Radhakrishnan et al. | |
| 2006/0063953 A1 | 3/2006 | Maurizio et al. | |
| 2006/0100278 A1 | 5/2006 | Cooper et al. | |
| 2006/0241088 A1 | 10/2006 | Arterburn et al. | |
| 2007/0232579 A1 * | 10/2007 | Freeman ................ | A61K 31/21 514/178 |

(Continued)

FOREIGN PATENT DOCUMENTS

DE 102012008730 A1 6/2013
EP 1407767 A1 4/2004

(Continued)

OTHER PUBLICATIONS

Shanshan Liu et al. (Abstract, Am. J. Physiol. 305 (11): F1533-F1541, Dec. 1, 2013).*

(Continued)

Primary Examiner — Sabiha N Qazi

(74) Attorney, Agent, or Firm — Fenwick & West LLP

(57) ABSTRACT

Various embodiments of this invention are directed to pharmaceutical compositions and methods for treating diseases, including focal segmental glomerulosclerosis or pulmonary arterial hypertension. The compositions of such embodiments include activated fatty acids such as alkyl substituted fatty acids, keto fatty acids and nitro fatty acids. The methods of various embodiments include administering an effective amount of 10-nitro-9(E)-octadec-9-enoic acid to treat such diseases.

6 Claims, 35 Drawing Sheets

(56) References Cited

U.S. PATENT DOCUMENTS

| | | | |
|---|---|---|---|
| 2007/0275893 A1 | 11/2007 | Quay | |
| 2008/0096961 A1 | 4/2008 | Serhan et al. | |
| 2009/0074857 A1 | 3/2009 | Dror et al. | |
| 2009/0326070 A1 | 12/2009 | Freeman et al. | |
| 2010/0166918 A1* | 7/2010 | Miller | A61K 45/06 426/73 |
| 2010/0216884 A1 | 8/2010 | Freeman | |
| 2010/0286257 A1 | 11/2010 | Perricone | |
| 2010/0286271 A1 | 11/2010 | Perricone | |
| 2010/0286272 A1 | 11/2010 | Perricone | |
| 2010/0331268 A1* | 12/2010 | Freeman | A61K 31/21 514/25 |
| 2011/0082206 A1 | 4/2011 | Miller | |
| 2011/0092594 A1 | 4/2011 | Yang | |
| 2011/0196037 A1 | 8/2011 | Yang | |
| 2011/0280852 A1* | 11/2011 | Miller | A61K 9/4858 424/94.1 |
| 2011/0312909 A1 | 12/2011 | Marina et al. | |
| 2011/0319325 A1 | 12/2011 | Miller | |
| 2012/0136034 A1 | 5/2012 | Freeman et al. | |
| 2013/0005730 A1 | 1/2013 | Sun et al. | |
| 2013/0039956 A1* | 2/2013 | Dietz | A61K 31/04 424/400 |
| 2013/0059912 A1 | 3/2013 | Freeman | |
| 2013/0101514 A1 | 4/2013 | Cushing | |
| 2013/0210917 A1 | 8/2013 | Freeman et al. | |
| 2014/0024713 A1 | 1/2014 | Yang | |
| 2014/0243380 A1 | 8/2014 | Yang | |
| 2014/0271844 A1* | 9/2014 | Miller | A61K 31/201 424/463 |
| 2015/0018417 A1 | 1/2015 | Freeman et al. | |
| 2015/0051283 A1 | 2/2015 | Dighiero et al. | |
| 2015/0246059 A1 | 9/2015 | Freeman et al. | |
| 2016/0081961 A1 | 3/2016 | Cushing | |
| 2016/0081962 A1 | 3/2016 | Miller et al. | |
| 2016/0151318 A1 | 6/2016 | Yang | |
| 2017/0095437 A1* | 4/2017 | Jorkasky | A61K 31/201 |
| 2018/0092948 A1* | 4/2018 | Weiss | A61K 35/744 |

FOREIGN PATENT DOCUMENTS

| | | |
|---|---|---|
| EP | 1772149 A1 | 4/2007 |
| GB | 587992 | 5/1947 |
| GB | 1407932 | 10/1975 |
| JP | 62-132804 | 6/1987 |
| JP | 2001-520189 A | 10/2001 |
| JP | 2003-509485 A | 3/2003 |
| JP | 2004-509097 A | 3/2004 |
| JP | 2008-520739 A | 6/2008 |
| JP | 2011-525525 A | 9/2011 |
| WO | WO 1998/09621 A | 3/1998 |
| WO | WO 2001/06983 A2 | 2/2001 |
| WO | WO 2001/15673 A3 | 3/2001 |
| WO | WO 2001/21575 A1 | 3/2001 |
| WO | WO 2001/060778 A2 | 8/2001 |
| WO | WO 2001/78654 A2 | 10/2001 |
| WO | WO 2001/78719 A1 | 10/2001 |
| WO | WO 2001/79156 A1 | 10/2001 |
| WO | WO 2002/022559 A2 | 3/2002 |
| WO | WO 2002/102364 A1 | 12/2002 |
| WO | WO 2003/031399 A1 | 4/2003 |
| WO | WO 2003/039533 A1 | 5/2003 |
| WO | WO 2005/073164 A1 | 8/2005 |
| WO | WO 2005/110396 A2 | 11/2005 |
| WO | WO 2006/055965 A2 | 5/2006 |
| WO | WO 2006/086727 A2 | 8/2006 |
| WO | WO 2007/140433 A2 | 12/2007 |
| WO | WO 2008/008767 A2 | 1/2008 |
| WO | WO 2008/011085 A1 | 1/2008 |
| WO | WO 2008/103753 A2 | 8/2008 |
| WO | WO 2009/017802 A1 | 2/2009 |
| WO | WO 2009/038671 A2 | 3/2009 |
| WO | WO 2009/129495 A1 | 10/2009 |
| WO | WO 2009/134383 A2 | 11/2009 |
| WO | WO 2009/149496 A1 | 12/2009 |
| WO | WO 2009/155439 A2 | 12/2009 |
| WO | WO 2010/012777 A1 | 2/2010 |
| WO | WO 2010/042877 A1 | 4/2010 |
| WO | WO 2010/078504 A1 | 7/2010 |
| WO | WO 2010/129763 A1 | 11/2010 |
| WO | WO 2010/129777 A1 | 11/2010 |
| WO | WO 2011/011882 A1 | 2/2011 |
| WO | WO 2011/014261 A1 | 2/2011 |
| WO | WO 2011/056126 A1 | 5/2011 |
| WO | WO 2011/098746 A1 | 8/2011 |
| WO | WO 2015/073527 | 5/2015 |

OTHER PUBLICATIONS

FIRSTx—A study of oral CXA-10, Primary FSGS, ClinicalTrial. Gov.NCT03422510 (Feb. 5, 2018), NIH US National Library of Medicine.*

Ian Grade, (Clinical Development of compound CXA-10, Complexa, Inc, pblication date Jun. 4, 2014).*

Shanshan Lui et al. (Am J Physiol Renal Physiol. Dec. 1, 2013; 305(11): F1533-F1541).*

Halying Lui et al. (Renal Physiol Renal Physiology 295:F942-1948, 2008).*

Abud-Mendoza et al., "Treating severe systemic lupus erythematosus with rituximab. An open study," *Reumatol. Clin.* 2009, vol. 5, No. 4, 147-152.

Adjei et al., "A Phase I Trial of the Farnesyl Transferase Inhibitor SCH66336: Evidence for Biological and Clinical Activity," *Cancer Res.* Apr. 1, 2000, vol. 60, 1871-1877.

Akaike et al., "Antagonistic Action of Imidazolineoxyl N-Oxides against Endothelium-Dreived Relaxing Factor/*NO through a Radical Reaction," *Biochem.* 1993, vol. 32, 827-832.

Alber, "Signaling mechanisms of the *Mycobacterium tuberculosis* receptor Ser/Thr protein kinases," *Curr. Opin. Struct. Biol.* Dec. 2009, vol. 19, No. 6, 650-657.

Altschul et al., "Gapped BLAST and PSI-BLAST: a new generation of protein database search programs," *Nucleic Acids Res.* 1997, vol. 25, No. 17, 3389-3402.

Anand et al., "Synthesis and Evaluation of Small Libraries of Triazolylmethoxy Chalcones, Flavanones and 2-aminopyrimidines as Inhibitors of Mycobacterial FAS-II and PknG," *Bioorganic & Medicinal Chem.* 2012, vol. 20, No. 17, 5150-5183.

Aunapuu, et al., "Morphological changes in experimental psotischemic rat kidney. A pilot study,"*Ann. Anat.* (2005), 63-70.

Arnold et al., "Nitric oxide activates guanylate cyclase and increases guanosine 3':5'-cyclic monophosphate levels in various tissue preparations," *Proc. Natl. Acad. Sci.* 1977. vol. 74, 3203-3207.

Artim et al., "Nitro-oleic acid targets transient receptor potential (TRP) channels in capsaicin sensitive afferent nerves of rat urinary bladder," *Expt. Neurol.* 2011, vol. 232, 90-99.

Asakura et al., "Synthesis and biological evaluation of γ-fluoro-β, γ-unsaturated acids," *J. of Flourine Chem.* 2006, vol. 127, 800-808.

Baker et al., "Fatty Acid Transduction of Nitric Oxide Signaling," *J. Biol. Chem.* Dec. 23, 2005, vol. 280(51), 42464-42475.

Baker et al., "Red cell membrane and plasma linoleic acid nitration products: Synthesis, clinical identification, and quantitation," *Proc. Natl. Acad. Sci.* Aug. 10, 2004, vol. 101, No. 32, 11577-11582.

Baker et al., "Convergence of nitric oxide and lipid signaling: Anti-inflammatory nitro-fatty acids," *Free Radic. Biol. Med.* 2009, vol. 46, 989-1003.

Baker et al., "Nitro-fatty Acid Reaction with Glutathione and Cysteine; Kinetic Analysis of Thiol Alkylation by a Michael Addition Reaction," *J. of Biol. Chem.* Oct. 19, 2007, vol. 282, No. 42, 31085-31093.

Balazy et al., "Vicinal Nitrohydroxyeicosatrienoic Acids: Vasodilator Lipids Formed by Reaction of Nitrogen Dioxide with Arachidonic Acid," *J. Pharmacol. ExTher.* 2001, vol. 299, No. 2, 611-619.

Balazy, "Isomerization and Nitration of Arachidonic Acid by Nitrogen Dioxide," *Advances in Mass Spectrometry* 2001, vol. 15, 375-376.

(56) References Cited

OTHER PUBLICATIONS

Baldus et al., "Endothelial transcytosis of myeloperoxidase confers specificity to vascular ECM proteins as targets of tyrosine nitration," *J. Clin. Invest.* 2001, vol. 108, No. 12, 1759-1770.
Baldus et al., "Is NO News Bad News in Acute Respiratory Distress Syndrome," *Am. J. Respir. Crit. Care Med.* 2001, vol. 163, 308-310.
Ballini et al., "Nitroalkanes and Ethyl Glyoxalate as Common Precursors for the Preparation of both β-keto Esters and α,β-unsaturated Esters," *Tetrahedron Letters* 2004, vol. 45, 7027-7029.
Ballini et al., "Fast Diastereoselective Baylis-Hillman Reaction by Nitroalkenes: Synthesis of Di- and Triene Derivatives," *Tetrahedron* 2004, vol. 60, 4995-4999.
Ballini et al., "(Z)-7-Nitro-3-Heptene as Central Intermediate for the Synthesis of Jasmone, Methyl Jasmonate and γ-Jasmolactone," *Synthetic Communications* 1989, vol. 19, Nos. 3-4, 575-583.
Banker et al., *Modern Pharmaceutics*, Marcel Dekker, Inc. 1979, New York (TOC).
Bates et al., "Nitroalkene Fatty Acids Mediate Activation of Nrf2/ARE-Dependent PPARγ-Dependent Transcription by Distinct Signaling Pathways and with and Significantly Different Potencies," *Biochem.* 2011, vol. 50, 7765-7773.
Bates et al., "Noncatalytic Interactions between Glutathione S-Transferases and Nitroalkene Fatty Acids Modulate Nitroalkene-Mediated Activation of Peroxisomal Proliferator-Activated Receptor γ," *Biochem.* 2009, vol. 48, 4159-4169.
Batthyany et al., "Reversible Post-translational Modification of Proteins by Nitrated Fatty Acids in Vivo," *J. Biol. Chem.* Jul. 21, 2006, vol. 281, No. 29, 20450-20463.
Baumer, "Iodostarin 'Roche' in the treatment of Syphilis," *Deutsche Medizinische Wochenschrift* 1913, vol. 39, 1361 (case abstract) (1 page).
Beckman et al., "Apparent hydroxyl radical production by peroxynitrite: Implications for endothelial injury from nitric oxide and superoxide," *Proc. Natl. Acad. Sci.* 1990, vol. 87, 1620-1624.
Bell-Parikh et al., "Biosynthesis of 15-deoxy-$\Delta^{12,14}$-PGJ$_2$ and the ligation of PPARγ," *J. Clin. Invest.* 2003, vol. 112, No. 6, 945-955.
Bennett et al., *Cecil Textbook of Medicine* 1996, 20$^{th}$ Ed., vol. 1, 1004-1010.
Bervejillo et al., "Estudio del Potencial Anti-Aterogenico del AANO$_2$ in Vivo," *Tesina del grado de la Licenciatura en Bioquiica, Facultad de Ciencias*, UdelR Feb. 2012, 5-6, Fig. 2 (in Spanish with English summary).
Biegert et al., "Sequence Context-specific Profiles for Homology Searching," *PNAS* 2009, vol. 106, No. 10, 3770-3775.
Bjorn, "Clues emerge about benefits of briefly blocking blood flow," *Nature* Feb. 2009, vol. 15, No. 2, 132.
Blair et al., "Bathophenanthrolinedisulphonic Acid and Bathocuproinedisulphonic Acid, Water Soluble Reagents for Iron and Copper," *Talanta* 1961, vol. 7, Nos. 3-4, 163-174 (abstract).
Blakemore, "The modified Julia olefination: alkene synthesis via the condensation of metallated heteroarylalkylsulfones with carbonyl compounds," *J. Chem. Soc. Perkin Trans.* I, Nov. 4, 2002, 2563-2585.
Blanco et al., "6-Methylnitroarachidonate: A novel esterified nitroalkene that potently inhibits platelet aggregation and exerts cGMP-mediated vascular relaxation," *Free Radic. Biol. Med.* 2011, vol. 50, 411-418.
Bligh et al., "A Rapid Method of Total Lipid Extraction and Purification," *Can. J. Biochem. Physiol.* 1959, vol. 37, No. 8, 911-917.
Bloodsworth et al., "Nitric Oxide Regulation of Free Radical- and Enzyme-Medicated Lipid and Lipoprotein Oxidation," *Arterioscler. Thromb. Vasc. Biol.* Jul. 2000, vol. 20, 1707-1715.
Boden et al., "Free fatty acids in obesity and type 2 diabetes: defining their role in the development of insulin resistance and β-cell dysfunction," *Euro. J. Clin. Invest.* 2002, 32 (Suppl. 3), 14-23.
Bonacci et al., "Gas-Phase Fragmentation Analysis of Nitro-Fatty Acids," *J. Am. Soc. Mass Spec.* 2011, vol. 22, 1534-1551.

Bonacci et al., "Nitro-oleic Acid Improves Insulin Signaling via Protein Tyrosine Phosphatase-1b Inhibition," *Free Radical Bio. Med.* Jan. 1, 2008, Elsevier Science, vol. 45, Suppl. 1, S154 (abstract).
Bonacci et al., "Electrophilic Fatty Acids Regulate Matrix Metalloproteinase Activity and Expression," *J. Biolo. Chem.* 2011, vol. 286, No. 18, 16074-16081 (abstract).
Bonomi et al., "Direct Metal Ion Substitution at the [M(Scys)$_4$]$^2$ Site of Rubredoxin," *J. Biol. Inorg. Chem.* 1998, vol. 3, No. 6, 595-605.
Borniquel et al., "Nitrated oleic acid up-regulates PPARγ and attenuates experimental inflammatory bowel disease," *Free Radic. Bio. Med.* 2010, vol. 49, Iss. 4, 499-505.
Boruwa et al., "Catalytic Asymmetric Henry Reaction," *Tetrahedron: Asymmetry* Dec. 27, 2006, Report No. 90, 17, 3315-3326.
Burdge, "α-Linolenic Acid Metabolism in Men and Women: Nutritional and Biological Implications," *Clin. Nutri. Metabol. Care* 2004, vol. 7, 137-144.
Cannon, *Burger's Medicinal Chemistry and Drug Discovery* 1995, Fifth Edition, vol. I: Principles and Practice, Chap. 19, John Wiley & Sons, Inc., 783-802.
Castro et al., "Cytochrome c: a catalyst and target of nitrate-hydrogen peroxide-dependent protein nitration," *Arch. Biochem. Biophys.* 2004, vol. 421, 99-107.
Chawla et al., "PPAR-γ dependent and independent effects on macrophage-gene expression in lipid metabolism and inflammation," *Nat. Med.* 2001, vol. 7, No. 1, 48-52.
Chen et al., "Peroxisome Proliferator-Activated Receptors and the Cardiovascular System," *Vitam. Horm.* 2003, vol. 66, 157-188.
Chen et al., "Synthesis and Screening of Novel Vitamin E Derivatives for Anticancer Functions," *European J. of Medicinal Chem.* 2012, vol. 58, 72-83.
Chen et al., "Troglitazone Inhibits Aterhosclerosis in Apolipoprotein E-Knockout Mice: Pleiotropic Effects on CD36 Expression and HDL," *Arterioscler. Thromb. Vasc. Biol.* 2001, vol. 21, 372-377.
Clapp et al., "Oxygenation of Monounsaturated Fatty Acids by Soybean Liposygenase-1: Evidence for Transient Hydroperoxide Formation," *Biochem.* 2006, vol. 45, 15884-15892.
Claudel et al., "Reduction of atherosclerosis in apolipoprotein E knockout mice by activation of the retinoid X receptor," *Proc. Natl. Acad. Sci.* 2001, vol. 98, No. 5, 2610-2615.
Coffey et al., "Catalytic consumption of nitric oxide by 12/15-lipoxygenase: Inhibition of monocyte soluble guanylate cyclase activation," *Proc. Natl. Acad. Sci.* Jul. 3, 2001, vol. 98, No. 14, 8006-8011.
Cole et al., "Deciphering the Biology of *Mycobacterium tuberculosis* from the Complete Genome Sequence," *Nature* 1998, vol. 393, 537-544.
Cole et al., "Nitro-Fatty Acid Inhibition of Neointima Formation After Endoluminal Vessel Injury," *Circ. Res.* Nov. 6, 2009, 1-8; Suppl. Materials 1-6.
Coles et al., "Nitrolinoleate Inhibits Platelet Activation by Attenuating Calcium Mobilization and Inducing Phosphorylation of Vasodilator-stimulated Phosphoprotein through Elevation of cAMP," *J. Biol. Chem.* Feb. 22, 2002, vol. 277, No. 8, 5832-5840.
Coles et al., "Nitrolinoleate Inhibits Superoxide Generation, Degranulation, and Integrin Expression by Human Neutrophils. Novel Antiinflammatory Properties of Nitric Oxide-Derived Reactive Species in Vascular Cells," *Circ. Res.* Sep. 6, 2002, vol. 91, 375-381.
Collins et al., "Troglitazone Inhibits Formation of Early Atherosclerotic Lesions in Diabetic and Nondiabetic Low Density Lipoprotein Receptor-Deficient Mice," *Arterioscler. Thromb. Vasc. Biol.* 2001, vol. 21, 365-371.
Communication pursuant to Article 94(3) EPC for European Application No. 08 780 348.2 dated Jul. 26, 2011.
Cosby et al., "Nitrite reduction to nitric oxide by deoxyhemoglobin vasodilates the human circulation," *Nat. Med.* 2003, vol. 9, No. 12, 1498-1505.
Cowley et al., "The *Mycobacterium tuberculosis* Protein Serine/threonine Kinase PknG Is Linked to Cellular Glutamate/glutamine Levels and Is Important for Growth in Vivo," *Molecular Microbio.* 2004, vol. 52, No. 6, 1691-1702.

(56) References Cited

OTHER PUBLICATIONS

Cui et al., "Nitrated Fatty Acids: Endogenous Anti-inflammatory Signaling Mediators," *J. Biol. Chem.* Nov. 24, 2006, vol. 281, No. 47, 35686-35698.

Dang et al. (Hung), "Anti-inflammatory Constituents of the Red Alga *Gracilaria verrucosa* and Their Synthetic Analogues," *J. Nat. Prod.* 2008, vol. 71, No. 2, 232-240.

Dangi et al., "Biogenic Synthesis, Purification, and Chemical Characterization of Anti-Inflammatory Resolvins Derived from Docosapentaenoic Acid (DPAn-6)," *J. Biol. Chem.* May 29, 2009, vol. 284, No. 22, 14744-14759.

Davies et al., "Oxidized Alkyl Phospholipids Are Specific, High Affinity Peroxisome Proliferator-activated Receptor γ Ligands and Agonists," *J. Biol. Chem.* May 11, 2001, vol. 276, No. 19, 16015-16023.

Defronzo et al., "Insulin Resistance: A Multifaceted Syndrome Responsible for NIDDM, Obesity, Hypertension, Dyslipidemia, and Atherosclerotic Cardiovascular Disease," *Diabetes Care* Mar. 1991, vol. 14, No. 3, 175-194.

Delerive et al., "Oxidized Phospholipids Activated PPARα in a Phospholipase A2-Dependent Manner," *FEBS Lett.* 2000, vol. 471, 34-38.

Del Mar Grasa et al., "Daily Oral Oleoyl-estrone Gavage Induces a Dose-dependent Loss of Fat in Wistar Rats," *Obesity Res.* Mar. 1, 2001, vol. 9, No. 3, 202-209.

Dembitsky et al., "Natural halogenated fatty acids: their analogues and derivatives," *Progress in Lipid Research* 2002, vol. 41, No. 4, 315-367.

De Meijere et al., "Metal-Catalyzed Cross-Coupling Reactions," *Wiley-VCH Verlag GMbH & Co.* 2004, Weinheim, vols. 1 and 2, XXII, ISBN-10: 3-527-30518-1 and ISBN-13: 978-3-527-30518-6 (TOC).

Denicola et al., "Diffusion of Nitric Oxide into Low Density Lipoprotein," *J. Biol. Chem.* 2002, vol. 277, No. 2, 932-936.

Denicola et al., "Diffusion of peroxynitrite across erythrocyte membranes," *Proc. Natl. Acad. Sci.* 1998, vol. 95, 3566-3571.

Desper et al., "Getting a Tree Fast: Neighbor Joining, FastME, and Distance-Based Methods," *Curr. Protoc. Bioinformatics* 2006, Chap. 6, Unit 6.3.

Diabetic ketoacidosis in www.mayoclinic.org/diseases-conditions/diabetic-ketoacidosis/basics/treatment/con-20026470 (retrieved from the internet Jan. 21, 2016).

D'Ischia, "Oxygen-Dependent Nitration of Ethyl Linoleate with Nitric Oxide," *Tetrahedron Lett.* 1996, vol. 37, No. 32, 5773-5774.

D'Ischia et al., "Medium-dependent Competitive Pathways in the Reactions of Polyunsaturated Fatty Acids with Nitric Oxide in the Presence of Oxygen. Structural Characterisation of Nitration Products and a Theoretical Insight," *Tetrahedron* 1999, vol. 55, 9297-9308.

Dodge et al., "Composition of phospholipids and of phospholipids fatty acids and aldehydes in human red cells," *J. Lipid Res.* 1967, vol. 8, 667-675.

Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm.

Dorwald, "Side reactions in Organic Synthesis," 2005, Wiley-VCH, 1-16.

Duan et al., "Nephrotoxicity of high- and low-osmolar contrast media: Protective role of forsinopril or telmisartan in a rat model," *J. Central S. Univ.* (Dec. 31, 2007), vol. 32, No. 5, 812-818.

Easton et al., "Polyunsaturated Nitroalkanes and Nitro-Substituted Fatty Acides," *Synthesis* 2001, vol. 3, 451-457.

Eberhardt et al., "Prevalence of Overweight and Obesity Among Adults with Diagnosed Diabetes—United States, 1988-1994 and 1999-2002," *CDC*, Nov. 19, 2004; vol. 53, No. 45, 1066-1068.

Eiserich et al., "Myeloperoxidase, a Leukocyte-Derived Vascular NO Oxidase," *Sci.* Jun. 28, 2002, vol. 296, 2391-2394.

Eiserich et al., "Pathophysiology of Nitric Oxide and Related Species: Free Radical Reactions and Modification of Biomolecules," *Molec. Aspects Med.* 1998, vol. 19, 221-357.

EP Communication issued on European Patent Application No. 09767748.8 dated Dec. 27, 2011.

Escudier et al., "Bevacizumab plus interferon alfa-2a for treatment of metastatic renal cell carcinoma: a randomized, double-blind phase III trial," *The Lancet* Dec. 22/29, 2007, vol. 370, 2103-2111.

European Examination Report issued in corresponding foreign application, EP Appl. 09767748.8, 1-3, dated Oct. 23, 2012.

Evans et al., "PPARs and the complex journey to obesity," *Nat. Med.* Apr. 2004, vol. 10, No. 4, 1-7.

Extended European Search Report and Written Opinion issued in corresponding foreign application, EP 10821313.3, 1-9 (dated Jul. 2013).

Extended European Search Report and Written Opinion issued in corresponding foreign application, EP 11804082.3, 1-5 (dated Nov. 29, 2013).

Extended European Search Report and Written Opinion issued in corresponding European Patent Application No. 12825790.4, 1-7 (dated Dec. 11, 2014).

Extended European Search Report and Written Opinion issued in corresponding European Patent Application No. 12839555.5, 1-6 (dated Feb. 2, 2015).

Extended European Search Report for EP08780348.2 dated Jul. 30, 2010.

Extended European Search Report and Written Opinion issued in European Patent Application No. 09767748.8, 1-6, dated Dec. 8, 2011.

Extended European Search Report and Written Opinion issued in EP Patent Application No. 09732031.1 dated Dec. 22, 2011.

Extended European Search Report and Written Opinion issued in EP Patent Application No. 13743207.6-1464, dated Jun. 22, 2015.

Extended European Search Report and Written Opinion issued in corresponding European Patent Application No. 16157509.7, 1-9 (dated May 30, 2016).

Feelisch et al., "Concomitant S-, N-, and heme-nitros(yl)ation in biological tissues and fluids: implications for the fate of NO in vivo," *FASEB J.* Nov. 2002, vol. 16, 1775-1785.

Ferreira et al., "Macrophage activation induces formation of the anti-inflammatory lipid cholesteryl-nitrolinoleate," *Biochem. J.* 2009, vol. 417, 223-234.

Ferry et al., "Binding of prostaglandins to human PPARγ: tool assessment and new natural ligands," *Eur. J. Pharmacol.* 2001, vol. 417, 77-89.

Finlayson-Pitts et al., "A Fourier Transform Infrared Spectrometry Study of the Reactions of Phosphatidylcholines with Gaseous $N_2O_5$ and $NO_2$," *Toxicol. Appl. Pharmacol.* 1987, vol. 89, 438-448.

Fiuza et al., "From the Characterization of the Four Serine/Threonine Protein Kinases (PknA/B/G/L) of Corynebacterium Glutamicum Toward the Role of PknA and PknB in Cell Division," *J. Biolo. Chem.* 2008, vol. 283, No. 26, 10899-18112.

Forman et al., "15-Deoxy-$\Delta^{12,14}$-Prostaglandin $J_2$ is a Ligand for the Adipocyte Determination Factory PPARγ," *Cell* 1995, vol. 83, 803-812.

Freeman et al., "Nitro-fatty Acid Formation and Signaling," *J. of Biol. Chem.* Jun. 6, 2008, vol. 283, No. 23, 15515-15519.

Freshney, "Culture of Animal Cells," *A Manual of Basic Technique* 1983, Alan R. Liss, Inc., New York, 1-6.

Fu et al., "Oleylethanolamide regulates feeding and body weight through activation of the nuclear receptor PPAR-α," *Nature* Sep. 4, 2003, vol. 425, 90-93.

Furstner et al., "Total Synthesis of Epohelmin B and Its Analogues," *Chem. Asian J.* 2008, vol. 3, 310-318.

Gallon et al., "The Identification of the Allylic Nitrite and Nitro Derivatives of Methyl Linoleate and Methyl Linolenate by Negative Chemical Ionization Mass Spectroscopy," *Lipids* 1993, vol. 28, No. 2, 125-133.

Gallon et al., "The Reaction of Low Levels of Nitrogen Dioxide with Methyl Linoleate in the Presence and Absence of Oxygen," *Lipids* 1994, vol. 29, No. 3, 171-176.

Gavin III et al., "Reducing Cardiovascular Disease Risk in Patients with Type 2 Diabetes: A Message from the National Diabetes Education Program," *Am. Fam. Physician* Oct. 15, 2003, vol. 68, No. 8, 1569-74.

(56) References Cited

OTHER PUBLICATIONS

Gladwin et al., "The emerging biology of the nitrite anion," *Nature* Nov. 2005, vol. 1, No. 6, 308-314.
Gladwin et al., "Role of circulating nitrite and S-nitrosohemoglobin in the regulation of regional blood flow in humans," *Proc. Natl. Acad. Sci.* 2000, vol. 97, No. 21, 11482-11487.
Gladwin et al., "S-Nitrosohemoglobin Is Unstable in the Reductive Erythrocyte Environment and Lacks $O_2$/NO-linked Allosteric Function," *J. Biol. Chem.* 2002, vol. 277, No. 31, 27818-27828.
Glauser et al., "The inflammatory response and tissue damage. The example of renal scars following acute renal infection," *Pediatric Nephrology* Oct. 1987, vol. 1, No. 4, 615-622 (Abstract) (from PubMed website Jan. 22, 2016).
Goodman & Gilman's *The Pharmacological Basis of Therapeutics*, Sixth Edition 1980, MacMillan Publishing Co., New York (TOC).
Goodman & Gilman's *The Pharmacological Basis of Therapeutics*, Ninth Edition 1996, McGraw-Hill Book Company, New York, Appendix II, 1707-1711 (TOC).
Goodman & Gilman's *The Pharmacological Basis of Therapeutics*, Tenth Edition 2001, McGraw-Hill Book Company, New York (TOC).
Gorczynski et al., "Evaluation of Nitroalkenes as Nitric Oxide Donors," *Bioorg. Med. Chem. Lett.* 2007, vol. 17, 2013-2017.
Gorczynski et al., "Regio-and Stereospecific Synthesis and Nitric Oxide Donor Properties of (E)-9- and (E)-10-Nitrooctadec-9-enoic Acids," *Org. Lett.* Apr. 25, 2006, vol. 8, No. 11, 2305-2308.
Gregory et al., "5-$HT_3$ Receptor Antogonists for the Prevention of Chemotherapy-Induced Nausea and Vomiting: A Comparison of Their Pharmacoogy and Clinical Efficacy," *Drugs* Feb. 1998, vol. 55, No. 2, 173-189.
Grisham, "Myoglobin-Catalyzed Hydrogen Peroxide Dependent Arachidonic Acid Peroxidation," *Free Radic. Biol. Med.* 1985, vol. 1, 227-232.
Groeger et al., "Discovery, Structural Characterization and Quantification of Novel Inflammatory-Induced Electrophilic Fatty Acid Derivatives," *Free Radical Bio. & Med.* 2008, vol. 45, No. 1, S134.
Groeger et al., "Cyclooxygenase-2 generates anti-inflammatory mediators from omega-3 fatty acids," *Nat. Chem. Bio.* Jun. 2010, vol. 6, 433-441.
Groeger et al., "Signaling Actions of Electrophiles: Anti-inflammatory Therapeutic Candidates," *Molec. Interven.* Feb. 2010, vol. 10, Issue 1, 39-50.
Guindon et al., "A Simple, Fast, and Accurate Algorithm to Estimate Large Phylogenies by Maximum Likelihood," *Systematic Bio.* 2003, vol. 52, No. 5, 696-704.
Guindon et al., "Estimating Maximum Likelihood Phylogenies with PhyML," *Methods in Molecular Bio.* 2009, vol. 537, 113-137.
Guo et al., "Atypical PKCζ transduces electrophilic fatty acid signaling in pulmonary epithelial cells," *Nitric Oxide* 2011, vol. 25, 366-372.
Gutierrez et al., "Nitric Oxide Regulation of Superoxide-Dependent Lung Injury: Oxidant-Protective Actions of Endogenously Produced and Exogenously Administered Nitric Oxide," *Free Radic. Biol. Med.* 1996, vol. 21, No. 1, 43-52.
Hartmann et al., "A randomized trial comparing the nephrotoxicity of cisplatin/ifosfamide-based combination chemotherapy with or without amifostine in patients with solid tumors," *Investigational New Drugs* 2000, vol. 18, 281-289.
Hogg et al., "Reactions of Nitric Oxide With Nitronyl Nitroxides and Oxygen: Prediction of Nitrate Formation by Kinetic Simulation," *Free Radic. Res.* 1995, vol. 22, No. 1, 47-56.
Hogg et al., "Inhibition of low-density lipoprotein oxidation by nitric oxide Potential role in atherogenesis," *FEBS Lett.* 1993, vol. 334, No. 2, 170-174.
Hogg, "The Biochemistry and Physiology of S-nitrosothiols," *Annu. Rev. Pharmacol. Toxicol.* 2002, 42, 585-600.
Ichikawa et al., "Nitroalkenes Suppress Lipopolysaccharide-Induced Signal Transducer and Activator of Transcription Signaling in Macrophages: A Critical Role of Mitogen-Activated Protein Kinase Phosphatase 1," *Endocrinology* May 8, 2008, vol. 149, No. 8, 4086-4094.
Ignarro et al., "Endothelium-Derived Relaxing Factor From Pulmonary Artery and Vein Possesses Pharmacologic and Chemical Properties Identical to Those of Nitric Oxide Radical," *Circ. Res.* 1987, vol. 61, 866-879.
Ignarro et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," *J. Pharmacol. ExTher.* 1988, vol. 244, No. 1, 181-189.
Iles et al., "Fatty acid transduction of nitric oxide signaling: nitrolinoleic acid mediates protective effects through regulation of the ERK pathway," *Free Radic. Biol. Med.* 2009, vol. 46, 866-875.
International Preliminary Report on Patentability for PCT/US2009/0047825 dated Jan. 6, 2011.
International Preliminary Report on Patentability issued in corresponding PCT/US2012/051304, 1-8 (dated Mar. 6, 2014).
International Preliminary Report on Patentability issued in corresponding PCT/US2012/059722, 1-9 (dated Apr. 24, 2014).
International Search Report and Written Opinion dated Dec. 4, 2009, in corresponding PCT/US2009/002628.
International Search Report and Written Opinion dated Apr. 21, 2015 corresponding to PCT/US2014/065203.
International Search Report and Written Opinion dated Aug. 19, 2013 corresponding to PCT/US2012/059722.
International Search Report and Written Opinion dated Jul. 13, 2011 corresponding to PCT/US2010/051059.
International Search Report and Written Opinion dated Jun. 2, 2013 corresponding to PCT/US2013/024476.
International Search Report and Written Opinion dated Jun. 30, 2009 corresponding to PCT/US2009/041018.
International Search Report and Written Opinion dated Mar. 23, 2012 corresponding to PCT/US2011/042011.
International Search Report and Written Opinion dated Mar. 5, 2010 corresponding to PCT/US2009/047825.
International Search Report and Written Opinion dated Nov. 1, 2012 corresponding to PCT/US2012/051304.
International Search Report and Written Opinion dated Nov. 27, 2014 corresponding to PCT/US2014/047073.
International Search Report and Written Opinion dated Oct. 12, 2006 corresponding to International Patent Application No. PCT/US2005/014305.
International Search Report and Written Opinion dated Oct. 24, 2008 corresponding to International Patent Application No. PCT/US2008/009274.
International Search Report PCT/US2010/002141 dated Nov. 24, 2010.
Itoh et al., "Synthesis of Docosahexaenoic Acid Derivatives Designed as Novel PPARγ Agonists and Antidiabetic Agents," *Bioorg. Med. Chem.* 2006, vol. 14, 98-108.
Janero et al., "Differential nitros(yl)ation of blood and tissue constituents during glyceral trinitrate biotransformation in vivo," *PNAS* Nov. 30, 2004, vol. 101, No. 48, 16958-16963.
Jeong et al., "Fenofibrate Prevents Obesity and Hypertriglyceridemia in Low-Density Lipoprotein Receptor-Null Mice," *Metabolism* May 2004, vol. 53, No. 5, 607-613.
Jimenez-Estrada et al., "Allyic Nitration of 3β-Sitosterol and Cholesterol Acetate: Preparation of 7-Nitro Derivatives," *Steroid* Jun. 1997, vol. 62, 500-503.
Jourd'Heuil et al., "The Oxidative and Nitrosative Chemistry of the Nitric Oxide/Superoxide Reaction in the Presence of Bicarbonate," *Arch. Biochem. Biophys.* 1999, vol. 365, No. 1, 92-100.
Junping et al., "Pharmacokinetics and antitumor effects of vincristine carried microemulsions composed of PEG-lipid, oleic acid, vitamin E and cholesterol," *Int. J Pharm.* Jan. 30, 2003, vol. 251, No. 1-2, 13-21, abstract provided.

(56) References Cited

OTHER PUBLICATIONS

Kansanen et al., "Nrf2-Dependent and -Independent Responses to Nitro-fatty Acids in Human Endothelial Cells: Identification of Heat Shock Response as the Major Pathway Activated by Nitro-oleic Acid," *J. Biol. Chem.* Oct. 5, 2009, 1-34.

Karp et al., "Clinical and Biologic Activity of the Farnesyltransferase Inhibitor R115777 in Adults with Refractory and Relapsed Acute Leukemias: A Phase 1 Clinical-Laboratory Correlative Trial," *Blood* Jun. 2001, vol. 97, No. 11, 3361-3369.

Katoh et al., "Recent Developments in the MAFFT Multiple Sequence Alignment Program," *Briefings in Bioinformatics* 2008, vol. 9, No. 4, 286-298.

Kelley et al., "Nitro-oleic Acid, a Novel and Irreversible Inhibitor of Xanthine Oxidoreductase," *J. Biol. Chem.* Dec. 28, 2008, vol. 283, No. 52, 36176-36184.

Khoo et al., "Activation of vascular endothelial nitric oxide synthase and heme oxygenase-1 expression by electrophilic nitro-fatty acids," *Free Radic. Bio. Med.* 2010, vol. 48, 230-239.

Khoo et al., "Electrophilic nitro-fatty acids: anti-inflammatory mediators in the vascular compartment," *Curr. Opn. Pharml.* 2010, vol. 10, 179-184.

Kim et al., "The effect of PPAR-γ agonist on glucose metabolism and insulin sensitivity in on-obese type 2 diabetic rat models," *Diabetes* Jun. 1, 2006, American Diabetes Association 55: Suppl. 1.

Kim et al., "Bisubstrate Ketone Analogues as Serotonin N-Acetyltransferase Inhibitors," *J. Med. Chem.* 2001, vol. 44, No. 15, 2479-2485.

Kissner et al., "Formation and Properties of Peroxynitrite as Studied by Laser Flash Photolysis, High-Pressure Stopped-Flow Technique, and Pulse Radiolysis," *Chem. Res. Toxicol.* Sep. 4, 1997, vol. 10, 1285-1292.

Kliewer et al. "A Prostaglandin $J_2$ Metabolite Binds Peroxisome Proliferatory-Activated Receptor γ and Promotes Adipocyte Differentiation," *Cell* 1995, vol. 83, 813-819.

Kliewer et al., "Fatty acids and eicosanoids regulate gene expression through direct interactions and peroxisome proliferator-activated receptors α and γ," *Proc. Natl. Acad. Sci.* Apr. 1997, vol. 94, 4318-4323.

Kobayshi, "The Reaction of Nitrogen Dioxide with Lung Surface Components: The Reaction with cis-9-octadecenoic Acid," *Chemosphere* 1983, vol. 12, No. 9/10, 1317-1325.

Koenitzer et al., "Redox signaling in inflammation: interactions of endogenous electrophiles and mitochondria in cardiovascular disease," *Ann. N. Y. Acad. Sci.* 2010, vol. 1203, 45-52.

Kunin, "Urinary Tract Infections in Females," *Clinical Infectious Diseases*, Jan. 1994, vol. 18, 1-10.

Lai et al., "Reactions of Dinitrogen Pentoxide and Nitrogen Dioxide with 1-Palmitoyl-2-Oleoyl-sn-Glycero-3-Phosphocholine," *Lipids* 1991, vol. 26(4), 306-314. Abstract.

Lärfars et al., "Activation of Nitric Oxide Release and Oxidative Metabolism by Leukotrienes B4, C4, and D4 in Human Polymorphonuclear Leukocytes," *Blood* Feb. 15, 1999, vol. 93, No. 4, 1399-1405.

Lee et al., "Rosiglitazone ameliorates cisplatin-induced renal injury in mice," *Nephrol. Dial. Transplant.* 2006, vol. 21, 2096-2105.

Lee et al., "Peroxisome proliferators-activated receptor-γ in macrophage lipid homeostasis," *Trends Endocrinol. Metab.* Oct. 2002, vol. 13, No. 8, 331-335.

Levy et al., "Lipid mediator class switching during acute inflammation: signals in resolution," *Nat. Immunol.* Jul. 2001, vol. 2, No. 7, 612-619.

Li et al., "Molecular recognition of nitrated fatty acids by PPARγ," *Nat. Struct. Mol. Biol.* 2008, 1-3.

Li et al., "Differential inhibition of macrophage foam-cell formation and atherosclerosis in mice by PPARalpha, betta/delta, and gamma," *J. Clin. Invest.* 2004, vol. 114, No. 11, 1564-1576.

Li et al., "PPARα Ligand Protects During Cisplatin-Induced Acute Renal Failure by Preventing Inhibition of Renal FAO and PDC Activity," *Am. J. Physiol. Renal Physiol.* Mar. 2004, vol. 286, F572-F580.

Lim et al., "Nitrolinoleate, a nitric oxide-derived mediator of cell function: Synthesis, characterization, and vasomotor activity," *Proc. Natl. Acad. Sci.* Dec. 10, 2002, vol. 99, No. 25, 15941-15946.

Lima et al., "Characterization of Linoleic Acid Nitration in Human Blood Plasma by Mass Spectrometry," *Biochem.* 2002, vol. 41, No. 34, 10717-10722.

Lima et al., "Cholesteryl Nitrolinoleate, a Nitrated Lipid Present in Human Blood Plasma and Lipoproteins," *J. Lipid Res.* 2003, vol. 44, 1660-1666.

Lima et al., "Nitrated Lipids Decompose to Nitric Oxide and Lipid Radicals and Cause Vasorelaxation," *Free Radical Bio. Med.* 2005, Elsevier Sciences, vol. 39, No. 4, 532-539.

Liu et al., "Accelerated reaction of nitric oxide with $O_2$ within the hydrophobic interior of biological membranes," *Proc. Natl. Acad. Sci.* Mar. 1998, vol. 95, 2175-2179.

Liu et al., "Combined losartan and nitro-oleic acid remarkably improves diabetic nephrophaty in mice," *Am. J Physiol. Renal Physiol.* Aug. 14, 2013, vol. 305, F1555-F1562.

Liu et al., "Nitrol-Oleic Acid Protects the Mouse Kidney from Ischemia and Reperfusion Injury," *Am. J. Physiol. Renal Physiol.* Oct. 2008, vol. 295, No. 4, F942-F949.

Lopez et al., "Second Generation of α-Tocopherol Analogs-Nitric Oxide Donors: Synthesis, Physiochemical, and Biological Characterization," *Bioorg. Med. Chem.* 2007, vol. 15, 6262-6272.

Löytynoja et al., "An Algorithm for Progressive Multiple Alignment of Sequences with Insertions,"*PNAS* Jul. 26, 2005, vol. 102, No. 30, 10557-10562.

Lundberg et al., "Nitrate and nitrite in biology, nutrition and therapeutics," *Nat. Chem. Bio.* Dec. 2009, vol. 5, No. 12, 865-869.

Luzzio, "The Henry reaction: recent examples," *Tetrahedron* 2001, vol. 57, 915-945.

Ma et al., "Hydrohalogenation Reaction of Substituted 1, 2-Allenic Carboxylic Acids, Esters, Amides, Nitriles, and Diphenyl Phosphine Oxides," *Synthesis* Dec. 4, 2001, No. 5, 713-730.

Manini et al., "Chemistry of Nitrated lipids: Remarkable Instability of 9-Nitrolinoleic Acid in Neutral Aqueous Medium and a Novel Nitronitrate Ester Product by Concurrent Autoxidation/Nitric Oxide-Release Pathways," *J. Org. Chem.* 2008, vol. 73, No. 19, 7517-7525.

March, "Effects of Structure on Reactivity," *Advanced Organic Chemistry* (1977 edition), McGraw-Hill Book Company, New York, 251-259.

Marnett et al., "Regulation of Prostaglandin Biosynthesis by Nitric Oxide Is Revealed by Targeted Deletion of Inducible Nitric-oxide Synthese," *J. Biol. Chem.* 2000, vol. 275, No. 18, 13427-13430.

Marshall et al., "Nitrosation and oxidation in the regulation of gene expression," *FASEB J.* 2000, vol. 14, 1889-1900.

Marx et al., "Peroxisome Proliferator-Activated Receptors and Atherogenesis: Regulators of Gene Expression in Vascular Cells," *Circ. Res.* May 14, 2004, vol. 94, No. 9, 1168-1178.

McIntyre et al., "Identification of an intracellular receptor for lysophosphatidic acid (LPA): LPA is a transcellular PPARγ agonist,"*Proc. Nad. Acad. Sci.* 2003, vol. 100(1), 131-136.

McLean, "Iodostarin," *Archives of Internal Medicine* 1912, vol. 10, 509.

Menendez et al., "Effects of gama-linolenic acid and oleic acid on paclitaxel cytotoxicity in human breast cancer cells," *European J. of Cancer* (Oxford, England: 1990) Feb. 2001, vol. 37, No. 3, 402-213.

Messerschmidt et al., *Handbook of Metalloproteins* 2001, Hoboken, NJ, John Wiley & Sons, Inc. (abstract).

Metabolite definition at http://www.nlm.nih.gov/medlineplus/ency/article/002258.htm (retrieved from the internet Jan. 21, 2016).

Meyer et al., "Uremia," *New Engl. J. Med.* Sep. 27, 2007, vol. 357, 1316-1325.

Minghetti, "Cyclooxygenase-2 (COX-2) in Inflammatory and Degenerative Brain Diseases," *J. Neuropathol. Exp. Neurol.* Sep. 2004, vol. 63, No. 9, 901-910.

Miranda et al., "The Chemical Biology of Nitric Oxide," *Nitric Oxide: Biology and Pathobiology* 2000, Academic Press, San Diego, 41-55.

(56) References Cited

OTHER PUBLICATIONS

Mitschke et al., "9- and 10-Nitro-oleic Acid Do Not Interfere with the GC-MS Quantitative Determination of Nitrite and Nitrate in Biological Fluids When Measured as Their Pentalfluorobenzyl Derivatives," *J. Chromatography B.* 2007, vol. 85, Issue 1, 287-291.

Montuschi et al., "Isoprostanes: markers and mediators of oxidative stress," *FASEB J.* Dec. 2004, vol. 18, 1791-1800.

Morgan et al., "Use of Animal Models of Human Disease for Nonclinical Safety Assessment of Novel Pharmaceuticals," *Toxicol. Pathol.* 2013, vol. 41, No. 3, 508-518.

Mukherjee et al., "A Selective Peroxisome Proliferator-Activated Receptor-γ (PPARγ) Modulatory Blocks Adipocyte Differentiation byt Stimulates Glucose uptake in 3T3-L1 Adipocytes," *Mol. Endocrinol.* 2000, vol. 14, 1425-1433.

Nadtochiy et al. "Mitochondrial nitroalkene formation and mild uncoupling in ischaemic preconditioning: implications for cardioprotection," *Card. Res. Adv. Access* 2008, 1-8.

Nadtochiy et al., "Nitroalkenes Confer Acute Cardioprotection via Adenine Nucleotide Transloase 1," *J. Biol. Chem.* Jan. 27, 2012, vol. 287, No. 5, 3573-3580.

Nagano et al., "Use of tacrolimus, a potent antifibrotic agent, in bleomycin-induced lung fibrosis," *Eur. Respir. J.* 2006, vol. 27, 460-469.

Nagy et al., "Oxidized LDL Regulates Macrophage Gene Expression through Ligand Activation of PPARγ," *Cell* 1998, vol. 93, 229-240.

Napolitano et al., "Acid-Promoted Reactions of Ethyl Linoleate with Nitrite Ions: Formation and Structural Characterization of Isomeric Nitroalkene, Nitrohydroxy, and Novel 3-Nitro-1,5-hexadiene and 1,5-Dinitro-1,3-pentadiene Products," *J. Org. Chem.* 2000, vol. 65, No. 16, 4853-4860.

Napolitano et al., "The acid-promoted reaction of ethyl linoleate with nitrite. New insights from $^{15}$N-labelling and peculiar reactivity of a model skipped diene," *Tetrahedron* 2002, vol. 58, 5061-5067.

Napolitano et al., "Acid-Induced Structural Modifications of Unsaturated Fatty Acids and Phenolic Olive Oil Constituents by Nitrite Ions: A Chemical Assessment," *Chem. Res. Toxicol.* 2004, vol. 17, 1329-1337.

Narayan et al., "Serine Threonine Protein Kinases of *Mycobacterial* Genus: Phylogeny to Function," *Physiological Genomics* 2007, vol. 29, 66-75.

Nathan, "Nitric oxide as a secretory product of mammalian cells," *FASEB J.* 1992, vol. 6, 3051-3064.

Newman et al., "Optimized Thiol Derivatizing Reagent for the Mass Spectral Analysis of Distributed Epoxy Fatty Acids," *J. Chromato.* May 22, 2011, No. 925, 223-240.

Niebisch et al., "Corynebacterial Protein Kinase G Controls 2-Oxoglutarate Dehydrogenase Activity via the Phosphorylation Status of the Odhl Protein," *J. Biolo. Chem.* 2006, vol. 281, No. 18, 12300-12307.

Notredame et al., "T-Coffee: A novel method for fast and accurate multiple sequence alignment," *J. Molec. Bio.* 2000, vol. 302, 205-217.

Nott et al., "An Intramolecular Switch Regulates Phosphoindependent FHA Domain Interactions in *Mycobacterium tuberculosis*," *Sci. Signaling* 2009, vol. 2, No. 63, ra 12.

O'Donnell et al., "Interactions Between Nitric Oxide and Lipid Oxidation Pathways: Implications for Vascular Disease," *Circ. Res.* 2001, vol. 88, 12-21.

O'Donnell et al., "15-Lipoxygenase Catalytically Consumes Nitric Oxide and Impairs Activation of Guanylae Cyclase," *J. Biol. Chem.* Jul. 16, 1999, vol. 274, No. 29, 20083-20091.

O'Donnell et al., "Catalytic Consumption of Nitric Oxide by Prostagladin H Synthase-1 Regulates Platelet Function," *J. Biol. Chem.* Dec. 8, 2000, vol. 275, No. 49, 38239-38244.

O'Donnell et al., "Nitration of Unsaturated Fatty Acids by Nitric Oxide-Derived Reactive Nitrogen Species Peroxynitrite, Nitrous Acid, Nitrogen Dioxide, and Nitronium Ion," *Chem. Res. Toxicol.* 1999, vol. 12, No. 1, 83-92.

O'Donnell et al., "Nitric Oxide Inhibition of Lipid Peroxidation: Kinetics of Reaction with Lipid Peroxyl Radicals and Comparison with α-Tocopherol," *Biochem.* 1997, vol. 36, No. 49, 15216-15223.

O'Hare et al., "Regulation of Glutamate Metabolism by Protein Kinases in Mycobacteria," *Mol. Microbio.* 2008, vol. 70, No. 6, 1408-1423.

Ono et al., "A Convenient Procedure for the Conversion of €-Nitroalkenes to (Z)-Nitroalkenes via egthro-β-Nitroselenides," *J. Chem. Soc., Chem Commun.* 1987, 1550-1551.

Ortiz-Lombardia et al., "Crystal Structure of the Catalytic Domain of the PknB Serine/Threonine Kinase from *Mycobacterium tuberculosis*," *J. Biolo. Chem.* 2003, vol. 278, No. 15, 13094-13100.

Padmaja, "The Reaction of Nitric Oxide With Organic Peroxyl Radicals," *Biochem. Biophys. Res. Commun.* 1993, vol. 195, No. 2, 539-544.

Park et al., "Modulation of Tumor Necrosis Factor-Related Apoptosis-Inducing Ligand-Induced Apoptosis by Chemotherapy in Thyroid Cancer Cell Lines," *Thyroid* 2003, vol. 13. No. 12, 1103-1110.

Pawliczak et al., "85-kDa Cytosolic Phospholipase $A_2$ Mediates Peroxisome Proliferator-activated Receptor γ Activation in Human Lung Epithelial Cells," *J. Biol. Chem.* 2002, vol. 277, 33153-33163.

*Pharma Medica* (2002), 20(5):1999-210 (in Japanese with brief English relevance).

Pryor et al., "Reaction of Nitrogen Dioxide with Alkenes and Polyunsaturated Fatty Acids: Addition and Hydrogen Abstraction Mechanisms," *J. Amer. Chem. Soc.* 1982, vol. 104, 6685-6692.

Punchard et al., The Journal of Inflammation Editorial, Sep. 27, 2004, *The Journal of Inflammation*, BioMed Central, vol. 1, No. 1, 1-4.

Quijano et al., "Reaction of Peroxynitrite with Mn-Superoxide Dismutase: Role of the Metal Center in Decomposition Kinetics and Nitration," *J. of Biol. Chem.* Apr. 13, 2001, vol. 276, No. 15, 11631-11638.

Radi et al., "Peroxynitrite Oxidation of Sulfhydryls: The Cytotoxic Potential of Superoxide and Nitric Oxide," *J. Biol. Chem.* 1991, vol. 266, No. 7, 4244-4250.

Radi et al., "Peroxynitrite Reactions with Carbon Dioxide-Bicarbonate," *Methods Enzymol.* 1999, vol. 301, No. 37, 353-367.

Ranu et al., "Highly Selective Reduction of Conjugated Nitroalkenes with Zinc Borohydride in DME," *Tetrahedron Letters* 1991, vol. 32, No. 29, 3579-3582.

Rassaf et al., "Concomitant Presence of N-Nitroso and S-Nitroso Proteins in Human Plasma," *Free Radic. Biol. Med.* 2002, vol. 33, No. 11, 1590-1596.

Rassaf et al., "NO adducts in mammalian red blood cells: too much or too little?" *Nat. Med.* 2003, vol. 9, No. 5, 481-482.

Remington's *Pharmaceutical Sciences* 1990, 18th Ed. (TOC).

Rosen et al., "PPARγ: a Nuclear Regulator of Metabolism, Differentiation, and Cell Growth," *J. Biol. Chem.* 2001, vol. 276, No. 1, 37731-37734.

Rowe et al., "Acesulfame Potassium," *Handbook of Pharma. Excipients* 2006, $5^{th}$ Ed., Great Britain: Pharmaceutical Press (abstract).

Rowe et al., *Handbook of Pharma. Excipients* 2006, $5^{th}$ Ed., Great Britain: Pharmaceutical Press, American Pharmacists Association.

Rubbo et al., "Form on Nitric Oxide: Chemical Events in Toxicity. Nitrix Oxide Regulation of Tissue Free Radical Injury," *Chem. Res. Toxicol.* 1996, vol. 9, No. 5, 809-820.

Rubbo et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives," *Arch. Biochem. Biophys.* Dec. 1, 1995, vol. 324, No. 1, 15-25.

Rubbo et al., "Nitric Oxide Reaction with Lipid Peroxyl Radicals Spares α-Tocopherol during Lipid Peroxidation," *J. Biol. Chem.* 2000, vol. 275, No. 25, 10812-10818.

Rubbo et al., "Nitric Oxide Regulation of Superoxide and Peroxynitrite-dependent Lipid Peroxidation," *J. Biol. Chem.* Oct. 21, 1994, vol. 269, No. 42, 26066-26075.

Rudnick et al., "Contrast-induced nephropathy: How it develops, how to prevent it," *Cleveland Clinic J. Med.* Jan. 2006, vol. 73, No. 1, 75-87.

(56) References Cited

OTHER PUBLICATIONS

Rudolph et al., "Cardiovascular Consequences When Nitric Oxide and Lipid Signaling Converge," *Circ. Res.* Sep. 11, 2009, vol. 105, 511-522.

Rudolph et al., "Endogenous generation and protective effects of nitro-fatty acids in murine model of focal cardiac ischaemia and reperfusion," *Cardiov. Res. Advance Access* 2009, 1-12.

Rudolph et al., "Nitro-fatty Acid Metabolome: Saturation, Desaturation, β-Oxidation, and Protein Adduction," *J. Biol. Chem.* Jan. 16, 2009, vol. 284, No. 3, 1461-1473.

Rudolph et al., "Nitro-Fatty Acids Reduce Atherosclerosis in Apolipoprotein E-Deficient Mice," *Ather. Thromb. Vasc. Bio.* May 2010, vol. 30, 938-945.

Rudolph et al., "Transduction of Redox Signaling by Electrophile-Protein Reactions," *Sc. Signaling* Sep. 29, 2009, vol. 2, Issue 90 re7, 1-13.

Ryan et al., "Diabetes and the Mediterranean Diet: a Beneficial Effect of Oleic Acid on Insulin Sensitivity, Adipocyte Glucose Transport and Endothelium-dependent Vasoreactivity," *Q. J. Med.* 2000, vol. 93, 85-91.

Saffer et al., "Choosing Drug Therapy for Patients with Hyperlipidemia," *Am. Fam. Physic.* Jun. 1, 2000, vol. 61, No. 11, 3371-3382.

Sarver et al., "Analysis of Peptides and Proteins Containing Nitrotyrosine by Matrix-assisted Laser Desorption/ionization Mass Spectrometry," *J. Am. Soc. Mass Specfrom.* 2001, vol. 12, No. 4, 439-448.

Satyanarayana et al., "Steroselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," *Organometallics* 1991, vol. 10, 804-807.

Saulnier-Blache et al., "A simple and highly sensitive radioenzymatic assay for lysophosphatidic acid quantification," *J. Lipid Res.* 2000, vol. 41, 1947-1951.

Scarpini et al., "Treatment of Alzheimer's Disease: Current Status and New Perspectives," *Lancet Neurol.* Sep. 2003, vol. 2, 539-547.

Scherr et al., "Structural Basis for the Specific Inhibition of Protein Kinase G, a Virulence Factor of *Mycobacterium tuberculosis*," *PNAS* 2007, vol. 104, No. 29, 12151-12156.

Schopfer et al., "Fatty Acid Transduction of Nitric Oxide Signaling Nitrolinoleic Acid is a Hydrophobically Stabilized Nitric Oxide Donor," *J. Biol. Chem.* May 13, 2005, vol. 280, No. 19, 19289-19297.

Schopfer et al., "Nitrolinoleic Acid: An endogenous peroxisome proliferator-activated receptor γ ligand," *Proc. Natl. Acad. Sci.* Feb. 15, 2005, vol. 102(7), 2340-2345.

Schopfer et al., "NO-dependent protein nitration: a cell signaling event or an oxidative inflammatory response?" *Trends Biochem. Sci.* 2003, vol. 28, 646-654.

Schopfer et al., "Covalent Peroxisome Proliferator-activated Receptor γ Adduction by Nitro-fatty Acids: Selective ligand activity and anti-diabetic signaling actions," *J. Biol. Chem.* Apr. 16, 2010, vol. 285, No. 16, 12321-12333.

Schopfer et al., "Detection and quantification of protein adduction by electrophilic fatty acids: mitochondrial generation of fatty acid nitroalkene derivatives," *Free Radic. Biol. Med.* 2009, vol. 46, 1250-1259.

Sculptoreanu et al., "Nitro-Oleic Acid Inhibits Firing and Activates TRPV-1 and TRPA1-Mediated Inward Currents in Dorsal Root Ganglion Neurons from Adult Male Rats," *J. Pharm. Expt. Thera.* 2010, vol. 333, No. 3, 883-895.

Serhan et al., "Anti-Inflammatory Actions of Neuroprotectin D1/Protectin D1 and Its Natural Stereoisomers: Assignments of Dihydroxy-Containing Docosatrienes," *J. Immunology* 2006, vol. 176, 1848-1859.

Setiadi et al., "Vitamin E models. Conformational analysis and stereochemistry of tetralin, choman, thiochroman and selenochroman," *J. Molecular Structure (Theochem)* 2002, vol. 594, 161-172.

Shaner et al., "Designing Herbicide Tolerance Based on Metabolic Alteration: the Challenges and the Future," *In Pesticide Biotransformation in Plants and Microorganisms* (Hall, J. et al.); ACS Symposium Series 2000, American Chemical Society; Washington DC, 353.

Sharpless et al., "A Mild Procedure for the Conversion of Epoxides to Allylic Alcohols. The First Organoselenium Reagent," *J. Am. Chem. Soc.* Apr. 18, 1973, vol. 95, No. 8, 2697-2699.

Sieker et al., "Rubredoxin in Crystalline State," *Methods Enzymol.* 1994, vol. 243, 203-216.

Simopoulos et al., "Omega-3 Fatty Acids in Inflammation and Autoimmune Diseases," *J. Amer. College of Nutrition* 2002, vol. 21, No. 6, 495-505.

Smith, "Prostanoid biosynthesis and mechanisms of action," *Am. Physiol. Soc.* 1992, vol. 263, F181-F191.

Snider et al., "Oxidative and Dehydrative Cyclizations of Nitroacetate Esters with Mn(Oac)$_3$," *Tetrahedron*, Sep. 23, 2002, vol. 58, No. 39, 7821-7827.

Söding et al., "HHsenser: Exhaustive Transitive Profile Search Using HMM-HMM Comparison," *Nucleic Acids Res.* 2006, vol. 34, W374-378.

Strowig et al., "Combination therapy using metformin or thiazolidinediones and insulin in the treatment of diabetes mellitus," *Diabetes, Obesity, and Metabolism* 633-641.

Subczynski et al., "Permeability of Nitric Oxide through Lipid Bilayer Membranes," *Free Radic. Res.* 1996, vol. 24, 343-349.

Summons to Attend Oral Proceedings dated Oct. 2, 2012, from corresponding European Patent Application No. 08780348.2.

Szekely et al., "A Novel Drug Discovery Concept for Tuberculosis: Inhibition of Bacterial and Host Cell Signaling," *Immun. Letters* 2008, vol. 116, No. 2, 225-231.

Szoka et al., "Comparative Properties and Methods of Preparation of Lipid Vesicles (Liposomes)," *Annu. Rev. Biophys. Bioeng.* 1980, vol. 9, 467-508.

Tang et al., "Nitroalkenes induce rat aortic smooth muscle cell apoptosis via activation of caspase-dependent pathways," *Biochem. Biophys. Res. Commun.* 2010, vol. 397, 239-244.

Thatcher et al., "Nitrates and No Release: Contemporary Aspects in Biological and Medicinal Chemistry," *Free Radic. Biol. Med.* 2004, vol. 37, No. 8, 1122-1143.

Thomas et al., "The biological lifetime of nitric oxide: Implications for the perivascular dynamics of NO and O$_2$," *Proc. Natl. Acad. Sci.* Jan. 2, 2001, vol. 98, No. 1, 355-360.

Tiwari et al., "Key Residues in *Mycobacterium tuberculosis* Protein Kinase G Play a Role in Regulating Kinase Activity and Survival in the Host," *J. Biolol. Chem.* 2009, vol. 284, No. 40, 27467-27479.

Tontonoz et al., "Stimulation of Adipogenesis in Fibroblasts by PPARγ2, a Lipid-Activated Transcription Factor," *Cell* 1994, vol. 79, 1147-1156.

Tontonoz et al., "mPPARγ2: tissue-specific regulator of an adipocyte enhancer," *Genes Dev.* 1994, vol. 8, No. 10, 1224-1234.

Toth, "High-Density Lipoprotein and Cardiovascular Risk," *Circulation* 2004, vol. 109, 1809-1812.

Trostchansky et al., "Nitrated Fatty Acids: Mechanisms of Formation, Chemical Characterization, and Biological Properties," *Free Rad. Biol. Med.* 2008, vol. 44, 1887-1896.

Tsikas et al., "Nitro-fatty Acids Occur in Human Plasma in the Picomolar Range: a Targeted Nitro-lipidomics GC-MS/MS Study," *Lipids* 2009, vol. 44, 855-865.

Tzameli et al., "Regulated Production of a Peroxisome Proliferatory-Activated Receptor-gamma Ligand during an Early Phase of Adipocyte Differentiation in 3T3-L1 Adipocytes," *J. Biol. Chem.* 2004, vol. 279, No. 34, 36093-36102.

Van Beilen et al., "Rubredoxins Involved in Alkane Oxidation," *J. Biolol. Chem.* 2002, vol. 184, No. 6, 1722-1732.

Vasil'Ev et al., "The action of nitrogen dioxide upon erucic acid," *Lomonosova* 1995, vol. 5, 50-58 (English abstract).

Vickers et al., "IGF-1 Treatment Reduces Hyperphagia, Obesity, and Hypertension in Metabolic Disorders Induced by Fetal Programming," *Endocrinol.* Sep. 2001, vol. 142, No. 9, 3964-3973.

Vidwans et al., "Differential Modulation of Prostaglandin H Synthase-2 by Nitric Oxide-Related Species in Intact Cells," *Biochem.* 2001, vol. 40, 11533-11542.

(56) References Cited

OTHER PUBLICATIONS

Villacorta et al., "Nitro-linoleic Acid Inhibits Vascular Smooth Muscle Cell Proliferation via the Keap1/Nrf2 Signaling Pathway," *Am. J Physiol. Heart Circ. Physiol.* Apr. 27, 2007, 1-9.
Villacorta et al., "PPARγ and its ligands: therapeutic implications in cardiovascular disease," *Clin. Sci.* 2009, vol. 116, 205-218.
Villarino et al., "Proteomic Identification of *M. tuberculosis* Protein Kinase Substrates: PknB Recruits GarA, a FHA Domain-containing Protein, Through Activation Loop-mediated Interactions," *J. Mol. Bio.* 2005, vol. 350, No. 5, 953-963.
'Virtual Chembook' in www.elmhurst.edu/~chm/vchembook/551fattyacids.html (retrieved Dec. 12, 2012).
Von Knethen et al., "Activation of Peroxisome Proliferator-Activated Receptor γ by Nitric Oxide in Monocytes/Macrophages Down-Regulates p47$^{phox}$ and Attenuates the Respiratory Burst," *J. Immunol.* 2002, vol. 169, 2619-2626.
Walburger et al., "Protein Kinase G from Pathogenic Mycobacteria Promotes Survival Within Macrophages," *Sci.* 2004, vol. 304, 1800-1804.
Wang et al., "Constitutive Activation of Peroxisome Proliferator-activated Receptor-γ Suppresses Pro-inflammatory Adhesion Molecules in Human Vascular Endothelial Cells," *J. Biol. Chem.* 2002, vol. 277, No. 37, 34176-34181.
Wang et al., "Effects of Endogenous PPAR Agonist Nitro-Oleic Acid on Metabolic Syndrome in Obese Zucker Rats," *PPAR Res.* 2010, vol. 2010, Art. ID 601562, 1-7.
Wang et al., "Nitro-oleic acid protects against endotoxin-induced endotoxemia and multiorgan injury in mice," *Am. J. Physiol. Renal Physiol.* 2010, vol. 298, F754-762.
Weber et al., "Fragmentation of Bovine Serum Albumin by Pepsin. 1. The Origin of the Acid Expansion of the Albumin Molecule," *J. Biolo. Chem.* 1964, vol. 239, No. 5, 1415-1423.
Wehenkel et al., "Mycobacterial Ser/Thr Protein Kinases and Phosphatases: Physiological Roles and Therapeutic Potential," *Biochemica et biophysica acta* 2008, vol. 1784, No. 1, 193-202.
Woodcock, "Synthesis of Nitrolipids. All Four Possible Diastereomers of Nitrooleic Acids: (E)- and (Z)-, 9- and 10-Nitro-octadec-9-enoic Acids," *Organic Letters* 2006, vol. 8, No. 18, 3931-3934.
Wright et al., "Fatty acid transduction of nitric oxide signaling: Nitrolinoleic acid potently activates endothelial heme oxygenase 1 expression," *PNAS* Mar. 14, 2006, vol. 103, No. 11, 4299-4304.
Wright et al., "Human Heme Oxygenase-1 Induction by Nitrolinoleic Acid is Mediated by cyclic AMP, AP-1, and E-box Response Element Interactions," *Biochem. J.* 2009, m. BJ20090339, 1-31.
Xu et al., "Lysophosphatidic Acid as a Potential Biomaker for Ovarian and Other Gynecologic Cancers," *JAMA* 1998, vol. 280, 719-723.
Zhang et al., "Lysophosphatidic Acid Induces Neointima Formation Through PPARgamma Activation," *J. ExMed.* 2004, vol. 199, No. 6, 763-774.
Zhang et al., "Selective disruption of PPARgamma2 impairs the development of adipose tissue and insulin sensitivity," *Proc. Natl. Acad. Sci.* 2004, vol. 101, No. 29, 10703-10708.
Zhang et al., "Nitro-Oleic Acid Inhibits Angiotensin II-Induced Hypertension," *Circ. Res.* 2010, vol. 107, 540-548.
Arbeeny, C., et al., "Renoprotection by Treatment with CXA10, an Endogenous Nitro-Fatty Acid," J. Am. Soc. Nephrol., Nov. 3, 2015, vol. 26, p. 126A, Abstract TH-PO158.
Arbeeny, C., et al., "Renoprotection by Treatment with CXA-10, an Endogenous Nitro Fatty Acid." Poster, Nov. 5, 2015, 1 page.
Chieffo, C., et al., "Use of an Obese Population in Phase I to Evaluate the Pharmacology of Oral CXA-10, an Endogenous Nitro-fatty Acid Signaling Agent." Poster, 4 pages (Sep. 26, 2016).
Eardley, K.S., et al., "The relationship between albuminuria, MCP-1/CCL2, and interstitial macrophages in chronic kidney disease," Kidney Int., 2006, vol. 69, pp. 1189-1197.
PCT International Search Report and Written Opinion for PCT/US16/55206, dated Dec. 23, 2016, 7 Pages.
Christiansen, T. et al., "Monocyte chemoattractant protein-1 is produced in isolated adipocytes, associated with adiposity and reduced after weight loss in morbid obese subjects," International Journal of Obesity, 2005, vol. 29, pp. 146-150.
Extended European Search Report, European Application No. 16852846. 1, dated Apr. 23, 2019, 10 pages.
Fazzari, M. et al., "Generation and esterification of electrophilic fatty acid nitroalkenes in triacylglycerides," Free Radical Biology and Medicine, 2015, vol. 87, pp. 113-124.
Geiger, S.S. et al., "Chrono-immunology: progress and challenges in understanding links between the circadian and immune systems," Immunology, 2015, vol. 146, No. 3, pp. 349-358.
Kalliokoski, A. et al., "Impact of OATP transporters on pharmacokinetics," British Journal of Pharmacology, 2009, vol. 158, No. 3, pp. 693-705.
Kelley, E.E. et al., "Fatty acid nitroalkenes ameliorate glucose intolerance and pulmonary hypertension in high-fat diet-induced obesity," Cardiovascular Research, 2014, vol. 101, No. 3, pp. 352-363.
Klinke, A. et al., "Protective Effects of 10-nitro-oleic Acid in a Hypoxia-Induced Murine Model of Pulmonary Hypertension," Jul. 1, 2014, vol. 51, No. 1, pp. 155-162.
König, J. et al., "Transporters and drug-drug interactions: important determinants of drug disposition and effects,"Pharmacological Review,, 2013, vol. 65, No. 3, pp. 944-966.
Martini, S. et al., "Integrative biology identifies shared transcriptional networks in CKD," Journal of the American Society of Nephrology, 2014, vol. 25, pp. 2559-2572.
Villacorta, L. et al., "Electrophilic nitro-fatty acids inhibit vascular inflammation by disrupting LPS-dependent TLR4 signaling in lipid rafts," Cardiovascular Research, 2013, vol. 98, No. 1, pp. 116-124.
Wang, H. et al., "Nitrooleic Acid Attenuates Lipid Metabolic Disorders and Liver Steatosis in DOCA-Salt Hypertensive Mice," PPAR Research, Mar. 1, 2015, vol. 2015, pp. 1-9.
Aunapuu, M., et al., "Morphological changes in experimental postischemic rat kidney. A pilot study," Annals of Anatomy, 2005, vol. 187, pp. 63-70.
Final Office Action for U.S. Appl. No. 14/962,170, dated Nov. 1, 2017, 8 Pages.
Liu, H., et al., "Nitro-oleic acid protects the mouse kidney from ischemia and reperfusion injury," Am J. Physiol. Renal. Physiol., 2008, vol. 295, pp. F942-F949.
United States Notice of Allowance, U.S. Appl. No. 14/921,880, dated Mar. 8, 2018, nine pages.
United States Allowed Claims, U.S. Appl. No. 14/921,880, dated Mar. 8, 2018, two pages.

* cited by examiner

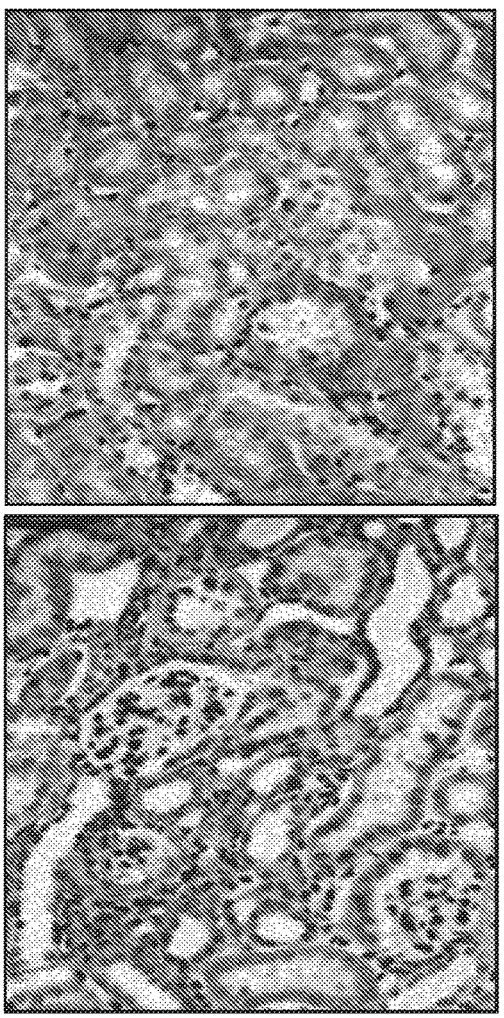
FIG. 11

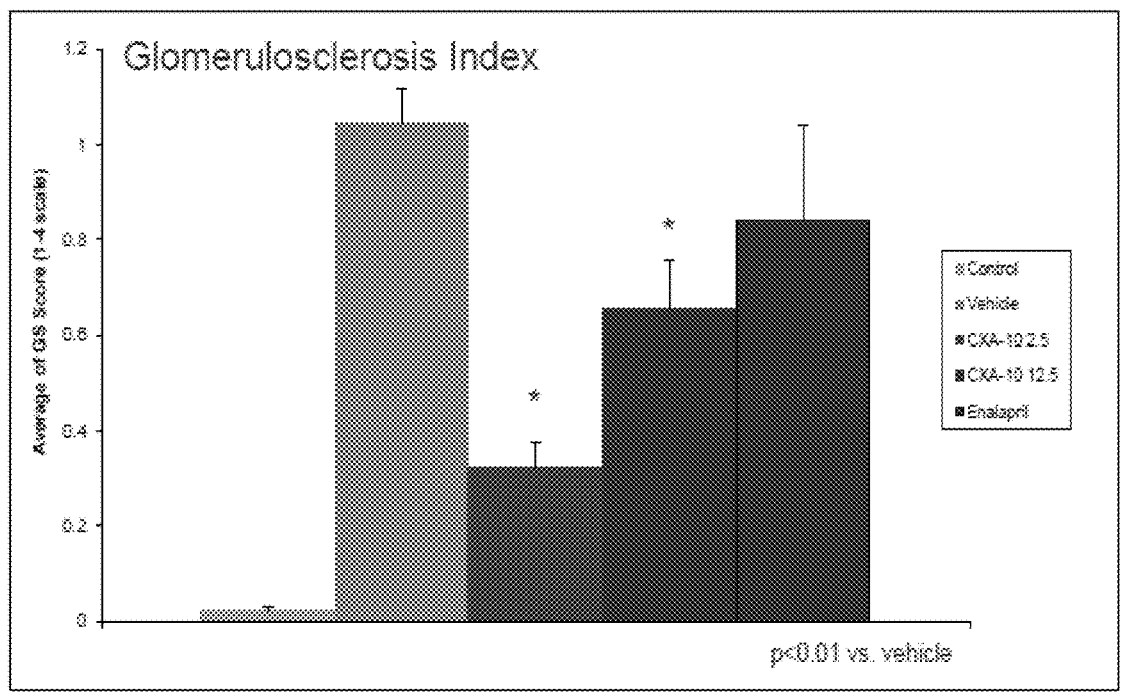
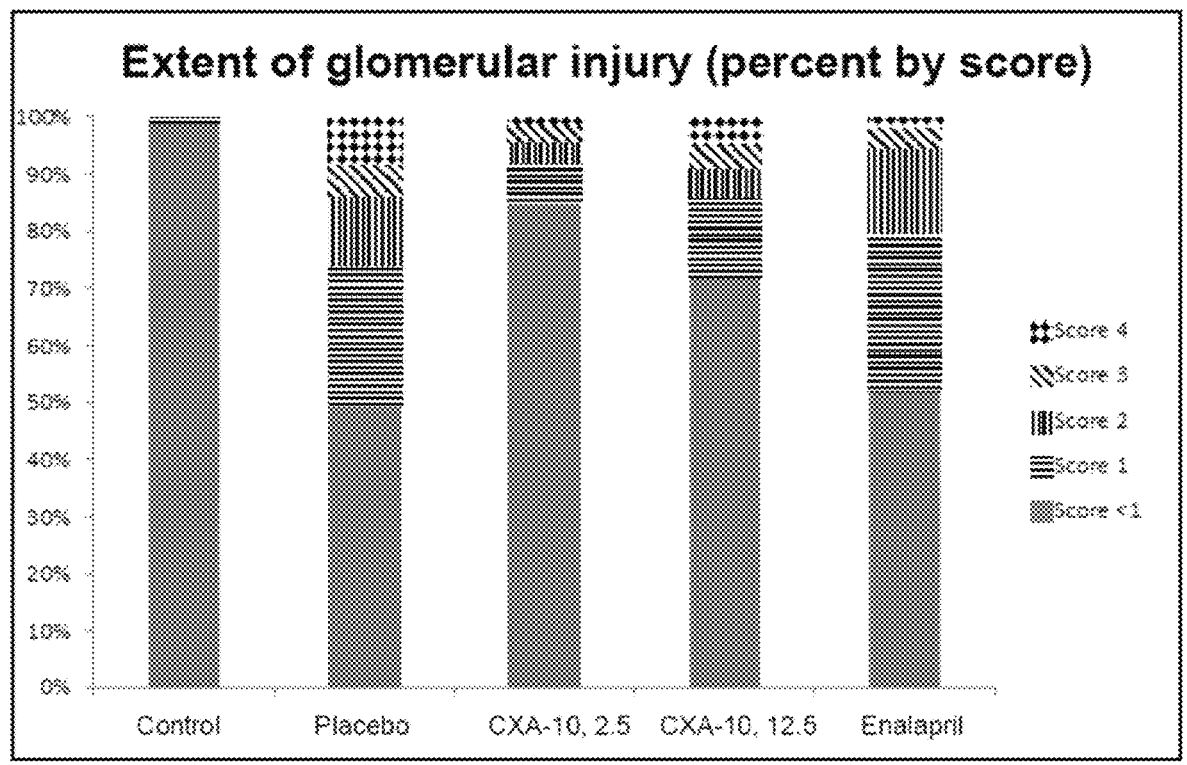
Figure 12

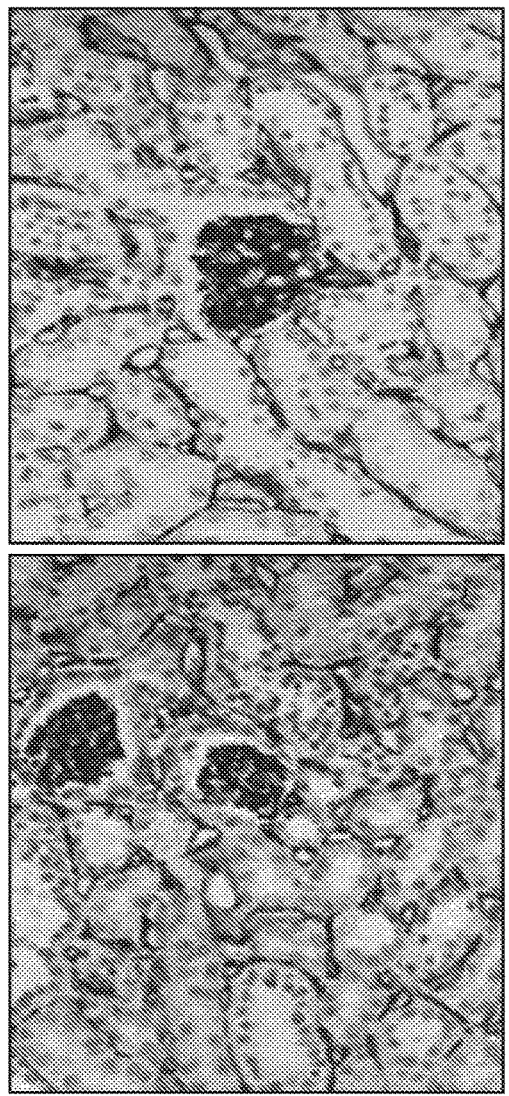
FIG. 14

A. CXA-10 2.5 mg/kg
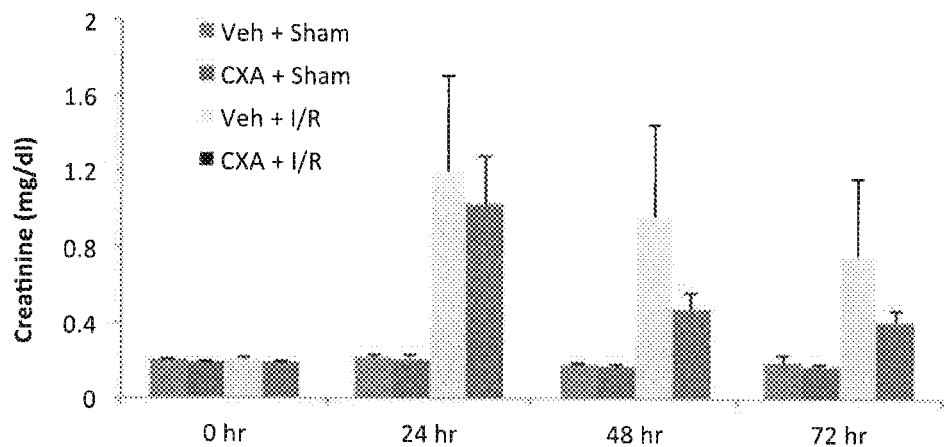
B. CXA-10 12.5 mg/kg
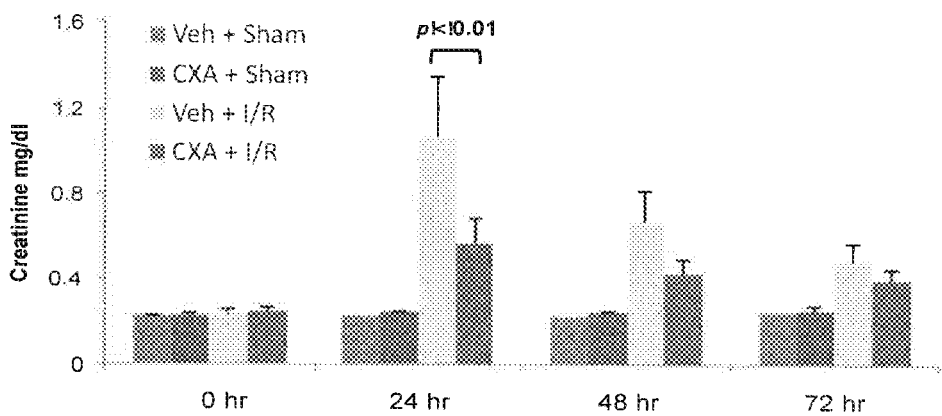
C. CXA-10 25 mg/kg
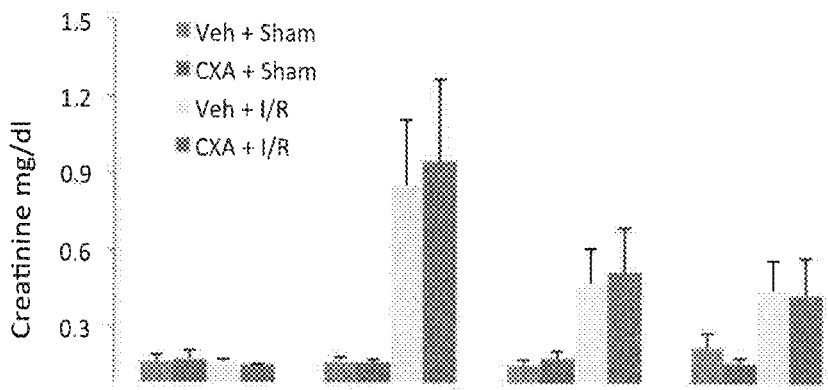
Figure 20

|  |  |  | Daily Assessments | | | | | | | | | | | | | | |
|---|---|---|---|---|---|---|---|---|---|---|---|---|---|---|---|---|---|
|  |  |  | Days | | | | | | | | | | | | | | |
| Time | Scrn | -1 OR Pre-dose | 1 | 2 | 3 | 4 | 5 | 6 | 7 | 8 | 9 | 10 | 11 | 12 | 13 | 14 | 19 |
| Procedure | | | | | | | | | | | | | | | | | |
| PK blood sampling |  |  | ✔ | ✔ | ✔ | ✔ |  |  |  |  |  | ✔ | ✔ | ✔ | ✔ | ✔ |  |
| Pravastatin |  |  | ✔ | ✔ |  |  |  |  |  |  |  | ✔ | ✔ |  |  |  |  |
| Vytorin® (simvastatin + ezetimibe) |  |  |  | ✔ | ✔ | ✔ |  |  |  |  |  |  |  | ✔ | ✔ | ✔ |  |
| 10-nitro-9(E)-octadec-9-enoic acid |  |  |  |  |  |  |  |  |  |  |  | ✔ | ✔ |  |  |  |  |

Figure 29

| Analyte | Parameter | n | Point Estimate | 95% CI's | Assessment | p-value |
|---|---|---|---|---|---|---|
| pravastatin | $C_{max}$ | 10 | 74.2 | (47.4, 116) | No conclusion | 0.1654 |
| | $AUC_{(0-t)}$ | 10 | 74.2 | (47.4, 116) | No conclusion | 0.1654 |
| | $AUC_{(0-inf)}$ | 9 | 67.3 | (43.8, 103) | No conclusion | 0.0659 |
| 3-alpha-hydroxy pravastatin | $C_{max}$ | 10 | 80.3 | (41.2, 156) | No conclusion | 0.4757 |
| | $AUC_{(0-t)}$ | 10 | 76.6 | (43.2, 136) | No conclusion | 0.3208 |
| | $AUC_{(0-inf)}$ | 5 | 215 | (33.3, 1390) | No conclusion | 0.3178 |
| ezetimbe | $C_{max}$ | 9 | 76.5 | (47.7, 123) | No conclusion | 0.2267 |
| | $AUC_{(0-t)}$ | 9 | 89.9 | (75.6, 107) | No conclusion | 0.1948 |
| | $AUC_{(0-inf)}$ | 9 | 96.2 | (69.5, 133) | No conclusion | 0.7925 |
| simvastatin | $C_{max}$ | 9 | 108 | (45.9, 254) | No conclusion | 0.8435 |
| | $AUC_{(0-t)}$ | 9 | 121 | (65.8, 222) | No conclusion | 0.4944 |
| | $AUC_{(0-inf)}$ | 9 | 118 | (65.6, 214) | No conclusion | 0.5291 |
| Simvastatin hydroxy acid | $C_{max}$ | 9 | 237 | (118, 478) | No conclusion | 0.0218 |
| | $AUC_{(0-t)}$ | 9 | 223 | (117, 425) | No conclusion | 0.0213 |

Test: CXA-10 with pravastatin or Vytorin Reference: pravastatin or Vytorin alone; Cmax = maximum concentration, AUC = area under the concentration time curve; n = number; CI: Confidence Interval

Figure 33

|  | Visit 1 | Visit 2 | Visit 3 | Visit 4 | Visit 5 | Visit 6 | Visit 7 |
|---|---|---|---|---|---|---|---|
| Time | Screening (Day-42 to -1) | Baseline (Day -14 to -1) | Day 14 | Day 28 (Wk 4) | Day 56 (Wk 8) | Day 84 (Wk 12) | Follow-up 112 (Wk 16) |
| Procedure | | | | | | | |
| Informed consent | ✓ | | | | | | |
| Demographics | ✓ | | | | | | |
| Medical/Surgical History | ✓ | ✓ | | | | | |
| Review eligibility | ✓ | ✓ | ✓ | ✓ | ✓ | ✓ | |
| 12-lead ECGs | ✓ | ✓ | ✓ | ✓ | ✓ | ✓ | |
| Vital signs, including BP | ✓ | ✓ | ✓ | ✓ | ✓ | ✓ | ✓ |
| Body Weight | ✓ | ✓ | ✓ | ✓ | ✓ | ✓ | ✓ |
| Clinical lab tests incl Mg and CPK | ✓ | ✓ | ✓ | ✓ | ✓ | ✓ | ✓ |
| Dose Adjustment as per protocol | | | ✓ | | | | |
| Dispense Study Medication | | ✓ | | | ✓ | ✓ | |
| Prior/Concomitant meds | ✓ | ✓ | ✓ | ✓ | ✓ | ✓ | ✓ |
| Adverse events | | ✓ | ✓ | ✓ | ✓ | ✓ | ✓ |
| Serum Biomarker includes extensive lipid profile | | ✓ | | | ✓ | ✓ | |
| PK blood sampling | | day 1 ✓ (8) * | ✓ | ✓ | ✓ | ✓ | ✓ |
| Urine biomarkers | | ✓ | | | | ✓ | |
| Up/c urine collection | ✓ | ✓ | | ✓ | ✓ | ✓ | ✓ |
| Blood for Genotype | ✓ | | | | | | |

Figure 34

TREATMENT OF FOCAL SEGMENTAL GLOMERULAR SCLEROSIS (FSGS) USING THERAPEUTICALLY EFFECTIVE ORAL DOSES OF 10-NITRO-9(E)-OCTADEC-9-ENOIC ACID

CROSS-REFERENCE TO RELATED APPLICATION

The present application claims the benefit of U.S. Provisional Application No. 62/236,702, filed Oct. 2, 2015, the disclosure of which is hereby incorporated by reference in its entirety.

SUMMARY

Various embodiments of the invention are directed to methods for treating a disease comprising administering a therapeutically effective amount of an activated fatty acid, such as an alkyl substituted fatty acid, a keto fatty acid, or a nitro fatty acid to a patient in need thereof. Various embodiments of the invention are directed to pharmaceutical compositions comprising a therapeutically effective amount of an activated fatty acid. In some embodiments described herein, the activated fatty acid is a nitro fatty acid. In some embodiments described herein, the activated fatty acid is a nitro oleic acid. In some embodiments described herein, the activated fatty acid is a 10-nitro-oleic acid, also known as CXA-10 or 10-nitro-9(E)-octadec-9-enoic acid.

BRIEF DESCRIPTION OF THE DRAWINGS

FIG. 11 shows the histological assessment of renal tissue obtained from the DOCA salt study following treatment. Representative photomicrographs of picosirius red stained sections are shown (×200). The top three photomicrographs are the control, untreated, and CXA-10 2.5 mpk (10-nitro-9(E)-octadec-9-enoic acid, 2.5 mg). The bottom two photomicrographs are CXA-10 12.5 mpk (10-nitro-9(E)-octadec-9-enoic acid, 12.5 mg) and Enalapril.

FIG. 12 shows the effect of treatment on glomerulosclerosis obtained from the DOCA salt study. Top graph: reading from left to right, the first bar represents the control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril. Bottom graph: score <1 is represented by the solid shaded area, score 1 is above score <1 and is represented by the horizontal lines, score 2 is above score 1 and is represented by the vertical lines, score 3 is above score 2 and is represented by the diagonal lines and score 4 is above score 3 and is represented by the diamond lines.

FIG. 14 shows the $CD31^+$ staining in renal tissue obtained from the DOCA salt study. The top three images are the control, vehicle, and CXA-10 2.5 mpk (10-nitro-9(E)-octadec-9-enoic acid, 2.5 mg). The bottom two images are CXA-10 12.5 mpk (10-nitro-9(E)-octadec-9-enoic acid, 12.5 mg) and Enalapril.

FIG. 20 shows serum creatinine levels after 10-nitro-9(E)-octadec-9-enoic acid treatment in rats in the ischemia/reperfusion study. Within each graph at 0, 24, 48 and 72 hours, reading from left to right, the first bar represents vehicle+sham, the second bar is CXA-10(10-nitro-9(E)-octadec-9-enoic acid)+sham, the third bar is vehicle+I/R and the final bar is CXA-10(10-nitro-9(E)-octadec-9-enoic acid)+I/R.

FIG. 29 shows the time and events table for PK blood sampling for the study of the pharmacokinetic interaction of 10-nitro-9(E)-octadec-9-enoic acid administered to steady state with pravastatin and Vytorin® (Simvastatin and Ezetimibe) in Healthy Males.

Pravastain+CXA-10 (10-nitro-9(E)-octadec-9-enoic acid) is represented by a light gray line with an unshaded square.

Figure 31:
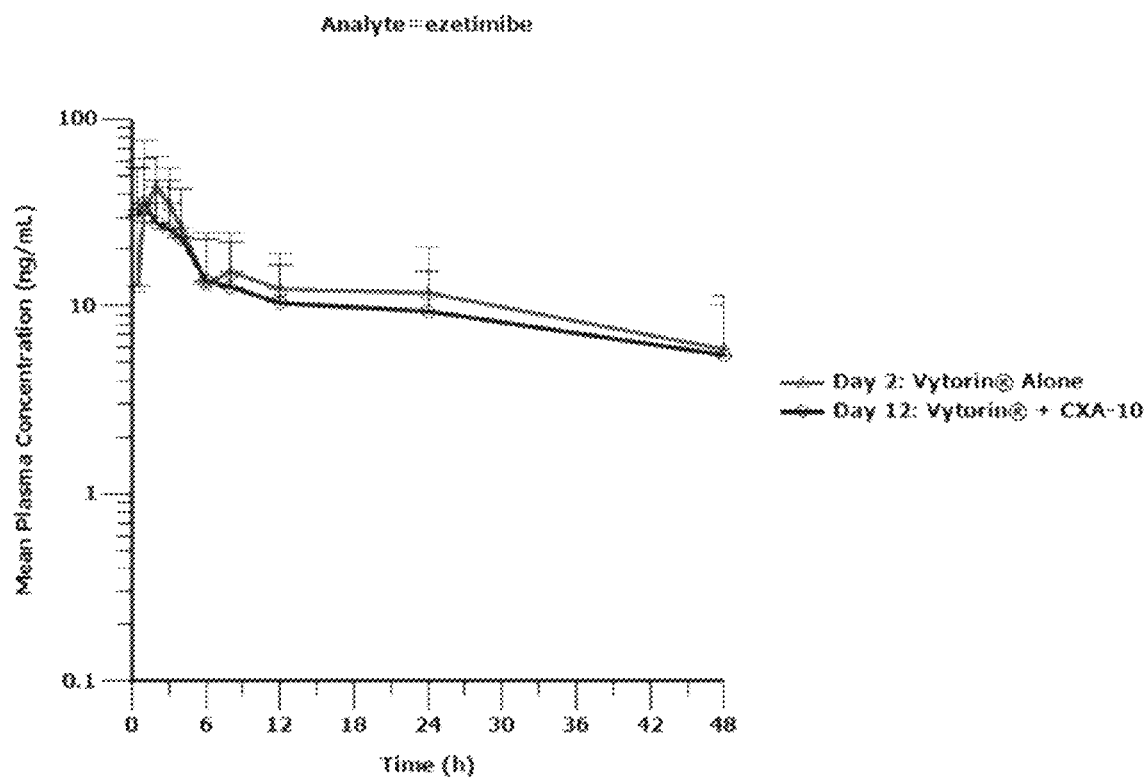

FIG. 31 shows mean (+SD) plasma ezetimbe total concentration-time profiles following oral administration of 10/20 mg of ezetimbe from the study of the pharmacokinetic interaction of 10-nitro-9(E)-octadec-9-enoic acid administered to steady state with pravastatin and Vytorin® (Simvastatin and Ezetimibe) in Healthy Males. Day 2: Vytorin® Alone is represented by a light grey line with and unshaded triangle and Day 12: Vytorin®+CXA-10 (10-nitro-9(E)-octadec-9-enoic acid) is represented by a dark gray line with an unshaded square.

Figure 32:
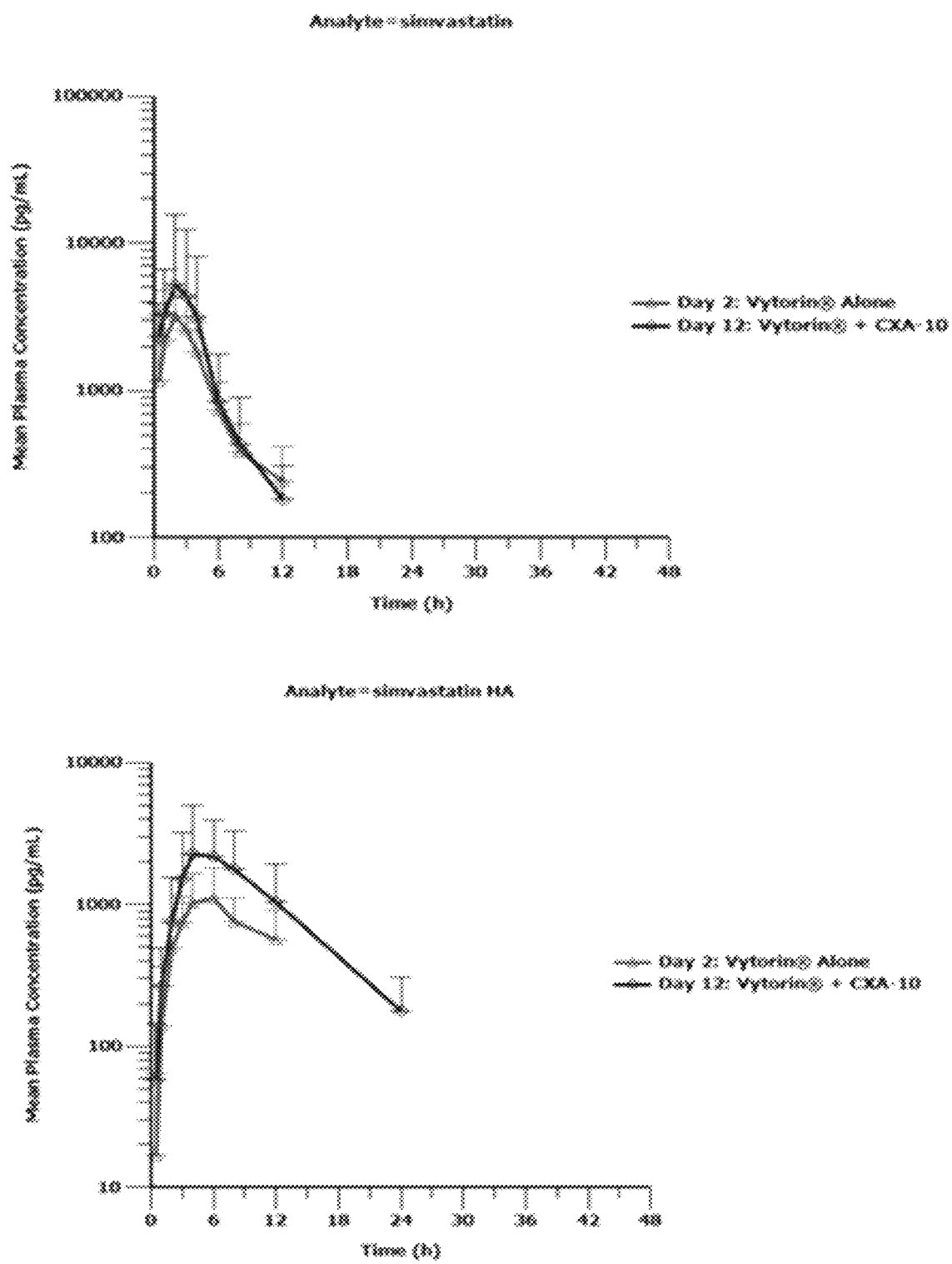

FIG. 32 shows mean (+SD) plasma simvastatin and simvastatin hydroxyl acid concentration-time profiles following oral administration of 10/20 mg of Vytorin® from the study of the pharmacokinetic interaction of 10-nitro-9 (E)-octadec-9-enoic acid administered to steady state with pravastatin and Vytorin® (Simvastatin and Ezetimibe) in Healthy Males. Day 2: Vytorin® Alone is represented by a light grey line with and unshaded triangle and Day 12: Vytorin®+CXA-10 (10-nitro-9(E)-octadec-9-enoic acid) is represented by a dark gray line with an unshaded square.

FIG. 33 is a table of summary statistics of comparison of test (analyte given with CXA-10) to reference analyte (analyte given as a single agent) from the study of the pharmacokinetic interaction of 10-nitro-9(E)-octadec-9-enoic acid administered to steady state with pravastatin and Vytorin® (Simvastatin and Ezetimibe) in Healthy Males.

FIG. 34 is a table of study assessments for the three month open label randomized study of two titration regimens of 10-nitro-9(E)-octadec-9-enoic acid in patients with nephrotic syndrome due to primary focal segmental glomerulosclerosis (FSGS).

Figure 35:
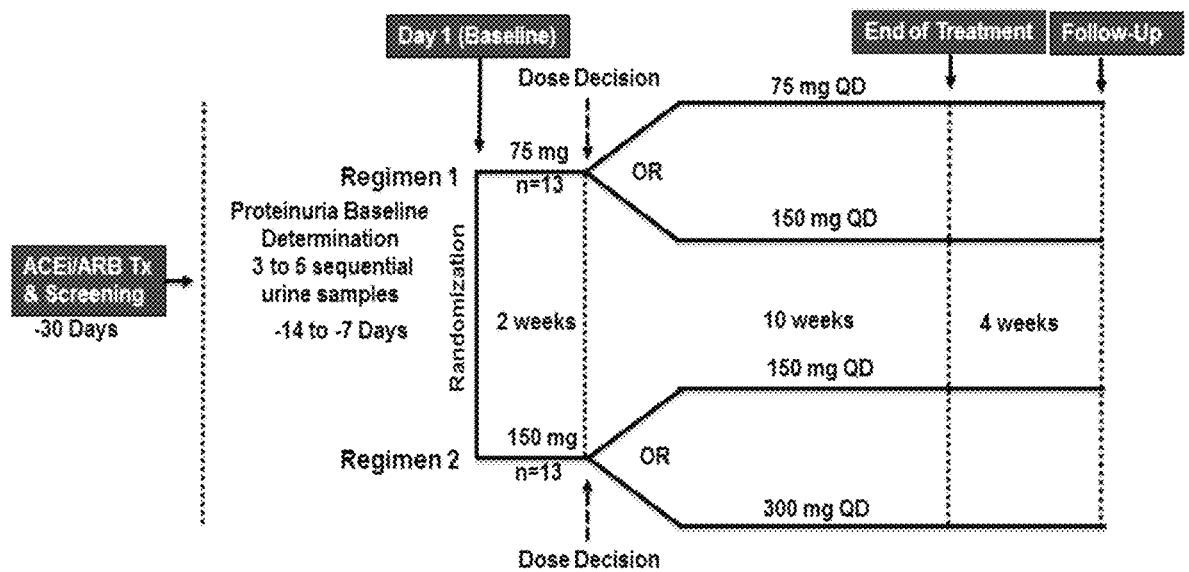

FIG. 35 is a study design for the three month open label randomized study of two titration regimens of 10-nitro-9 (E)-octadec-9-enoic acid in patients with nephrotic syndrome due to primary focal segmental glomerulosclerosis (FSGS).

DETAILED DESCRIPTION

Abbreviations and Definitions

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

Table 1 provides a list of abbreviations and definition of terms.

TABLE 1

| | |
|---|---|
| AE | Adverse Event |
| ALT | Alanine aminotransferase |
| AST | Aspartate aminotransferase |
| AUC0-∞ | Area under the plasma drug concentration time curve from time 0 to infinity |
| AUC0-last | Area under the plasma drug concentration versus time curve from time 0 to time of last measurable concentration |
| BHT | Butylated hydroxytoluene |

TABLE 1-continued

| | |
|---|---|
| BID | Twice daily |
| BMI | Body mass index |
| BP | Blood pressure |
| BPM | Beats per minute |
| BUN | Blood urea nitrogen |
| CI | Confidence Interval |
| CKD | Chronic Kidney Disease |
| CKI | Chronic Kidney Injury |
| CL/F | Clearance following oral administration |
| Cmax | Maximum observed plasma drug concentration |
| CPK | Creatine phosphokinase |
| CRF | Case report form |
| CRP | C-Reactive Protein |
| DBP | Diastolic blood pressure |
| DHETs | Dihydroxyeicosatrienoic acids |
| DL | Dose level |
| DOCA | Deoxycorticosterone acetate |
| E/T | Early termination |
| ECG | Electrocardiogram |
| EETs | Epoxyeicosatrienoic acids |
| eGFR | Estimated glomerular filtration rate |
| ELISA | Enzyme-linked immunosorbent assay |
| ES | Exposure response |
| FBG | Fasting blood glucose |
| FDA | Food and Drug Administration |
| FIH | First-in-human |
| GCLM | Glutamate cysteine ligase modifier subunit |
| GLP | Good laboratory practice |
| GGT | Gamma-glutamyl transferase |
| HbA1c | Hemoglobin A1c |
| HBsAg | Hepatitis B virus surface antigen |
| HCV Ab | Hepatitis C virus antibody |
| HDL | High density lipoprotein |
| HIPAA | Health Insurance Portability and Accountability Act of 1996 |
| HIV | Human immunodeficiency virus |
| HO-1 | Heme oxygenase-1 |
| HR | Heart rate |
| HSP | Heat shock proteins |
| ICH | International Conference on Harmonization |
| IEC | Independent Ethics Committee |
| IL-1 | Interleukin 1 |
| IL-6 | Interleukin 6 |
| IRB | Institutional Review Board |
| IVCD | Intra-ventricular conduction delay |
| Keap 1 | Kelch-like ECH-associated protein |
| Kim-1 | Kidney injury molecule-1 |
| LBBB | Left bundle branch block |
| LDL | Low density lipoprotein |
| LFT | Liver function test |
| LQTS | Long QT syndrome |
| MCH | Mean corpuscular hemoglobin |
| MCHC | Mean cell hemoglobin concentration |
| MCP-1 | Monocyte chemoattractant protein-1 |
| MCV | Mean cell volume |
| NCA | Non-compartmental analysis |
| NF-κB | Nuclear factor κB |
| NKDEP | National Kidney Disease Education Program |
| NOAEL | No observed adverse effect level |
| NQO1 | NAD(P)H quinone oxidoreductase 1 |
| Nrf2 | Nuclear factor E2-related factor 2 |
| NSAIDs | Non-steroidal anti-inflammatory drugs |
| OA-NO2 | Nitro-oleic acid |
| PAI-1 | Plasminogen activator inhibitor-1 |
| PBMCs | Peripheral blood mononuclear cells |
| PD | Pharmacodynamics |
| PGx | Pharmacogenetic |
| PK | Pharmacokinetics |
| qRT-PCR | Quantitative reverse transcriptase-polymerase chain reaction |
| RAS | Renin-angiotensin system |
| RBBB | Right bundle branch block |
| RBC | Red blood cell |
| RBP4 | Retinol binding protein |
| RQ | Relative Quantity |
| RR | Respiratory rate |
| SAE | Serious Adverse Event |
| SAP | Statistical Analysis Plan |

TABLE 1-continued

| | |
|---|---|
| sEH | Soluble epoxide hydrolase |
| SBP | Systolic blood pressure |
| SOP | Standard Operating Procedure |
| SPM | Study Procedures Manuals |
| t½ | Terminal phase half-life |
| Tmax | Time to maximum plasma drug concentration |
| TNFα | Tumor Necrosis Factor alpha |
| UAE | Urinary albumin excretion |
| ULN | Upper limit of normal |
| WBC | White blood cell |
| Vd/F | Volume of distribution following oral administration |
| WNL | Within normal limits |
| λz | Terminal elimination rate constant |

The term "alkyl" is used in this description to denote a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

An "alkenyl group" is as a branched or unbranched hydrocarbon group of 2 to 24 carbon atoms and structural formula containing at least one carbon-carbon double bond. Examples of alkenyl groups include, without limitations, ethylenyl, hexenyl, octandecenyl, octadecadienyl.

The phrase "alkynyl group" as employed here refers to a branched or unbranched hydrocarbon group of 2 to 24 carbon atoms and containing at least one carbon-carbon triple bond.

As used herein, "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, trifluoromethoxy, nitro, cyano, isocyano, hydroxy, alkoxy, amino, carboxy, alkoxycarbonyl, aryl, and heteroaryl. Exemplary aryl groups include but are not limited to phenyl, naphthyl, tetrahydronaphthyl, chlorophenyl, methylphenyl, methoxyphenyl, trifluoromethylphenyl, nitrophenyl, and 2,4-methoxychlorophenyl.

The term "halogen" and "halo" refers to —F, —Cl, —Br or —I.

The term "heteroatom" is meant to include oxygen (O), nitrogen (N), and sulfur (S).

The term "hydroxyalkyl," refers to an alkyl radical having the indicated number of carbon atoms wherein one or more hydrogen atoms of the alkyl group is replaced with a hydroxy group. Examples of hydroxyalkyl groups include, but are not limited to, hydroxymethyl, hydroxyethyl, hydroxypropyl, hydroxybutyl, hydroxypentyl, hydroxyhexyl, and branched versions thereof.

The term "haloalkyl," refers to an —$(C_1-C_8)$alkyl group wherein one or more hydrogen atoms in the $C_1-C_8$ alkyl group is replaced with a halogen atom, which can be the same or different. Examples of haloalkyl groups include, but are not limited to, difluoromethyl, trifluoromethyl, 2,2,2-trifluoroethyl, 4-chlorobutyl, 3-bromopropylyl, pentachloroethyl, and 1,1,1-trifluoro-2-bromo-2-chloroethyl.

The term "amine or amino" refers to an —$NR^pR^q$ group wherein $R^p$ and $R^q$ each independently refer to a hydrogen, $(C_1-C_8)$alkyl, $(C_1-C_8)$haloalkyl, and $(C_1-C_6)$hydroxyalkyl group.

The term "oxo" refers to an oxygen atom doubly bonded to a carbon or another element such as, for example a nitrogen, sulfur or selenium.

The term "heterocyclyl" refers to a monocyclic, bicyclic, tricyclic, or polycyclic system, which is either unsaturated or aromatic and which contains from 1 to 4 heteroatoms, independently selected from nitrogen, oxygen and sulfur, wherein the nitrogen and sulfur heteroatoms are optionally oxidized and the nitrogen heteroatom optionally quaternized, including bicyclic, and tricyclic ring systems. The heterocyclyl may be attached via any heteroatom or carbon atom. Heterocyclyl groups include heteroaryls as defined above. Representative examples of heterocyclyl includes, but is not limited to, benzoxazolyl, benzisoxazolyl, benzthiazolyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocyclyl group can be unsubstituted or optionally substituted with one or more substituents.

The term "cycloalkyl" refers to a monocyclic or bicyclic ring system containing one or two saturated or unsaturated rings.

The term "haloalkyl," refers to a $C_1-C_8$ alkyl group wherein one or more hydrogen atoms in the $C_1-C_8$ alkyl group is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" is employed here to refer to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and preferably one to four, substituents selected from, for example, halo, alkyl, alkenyl, trifluoromethoxy, nitro, cyano, isocyano, hydroxy, alkoxy, amino, carboxy, alkoxycarbonyl, aryl, and heteroaryl. Examples of heteroaryl groups include, but are not limited to, thienyl, furyl, pyridinyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term n-3, n-6, or n-9 polyunsaturated fatty acids (PUFA); n-3, n-6, or n-9 electrophilic fatty acid derivative (EFAD), respectively; or any of their respective metabolites is used interchangeably with the term ω-3, ω-6, or ω-9 polyunsaturated fatty acids (PUFA), respectively or ω-3, ω-6, or ω-9 electrophilic fatty acid derivatives (EFAD), respectively or its metabolites. Similarly, the term omega-3, omega-6, or omega-9 polyunsaturated fatty acids (PUFA), or omega-3, omega-6, or omega-9 electrophilic fatty acid derivatives (EFAD), or its metabolites, refers to the same.

In this context, the category of "metabolites" includes regioisomers, stereoisomers, and structural analogs of fatty acids. Thus, the inventive metabolites include activated fatty acids having tails of different carbon length, as well as positional isomers of the double bond. Also included within the class of metabolites are positional isomers and derivatives of PUFA's. Additionally, the double bond can be a cis (Z) double bond or a trans (E) double bond. Pursuant to the invention the metabolite category can encompass a small-molecule analogs of activated fatty acids, as described in greater detail below.

The term "derivative" refers to a compound that is derived from a similar compound, or a compound that can be imagined to arise from another compound, if one or more atoms are replaced with another atom or group of atoms. Derivatives of the fatty acid metabolites in accordance with the present invention include without limitation all compounds in which one or more carbon atoms in the activated fatty acid tail are substituted with oxygen, sulfur or amino groups. For example, the activated fatty acid tail can contain one of more polyethylene glycol units or one or more 1,2-diaminoethane units or combinations thereof.

The term "biological sample" refers to tissue, cells, cellular extract, homogenized tissue extract, a mixture of one or more enzymes in a suitable physiologically acceptable carrier, such as a mixture that includes without limitation the hydoxy dehydrogenases and cyclooxygenases.

The compounds of the invention can exist in various isomeric forms, including configurational, geometric, and conformational isomers, as well as existing in various tautomeric forms, particularly those that differ in the point of attachment of a hydrogen atom. The term "isomer" is intended to encompass all isomeric forms of a compound of this invention, including tautomeric forms of the compound.

Certain compounds described here may have on or more asymmetric carbon atoms and therefore exist in different enantiomeric and diastereomeric forms. The compounds of the invention can be in the form of an optical isomers or a diastereomers. Accordingly, the invention encompasses compounds in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6th ed. (Wiley, 2001) and DESIGN AND APPLICATION OF PRODRUGS (Harwood Academic Publishers Gmbh, 1985).

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 100 mg means in the range of 90 mg-110 mg.

"Administering" when used in conjunction with a therapeutic, means to administer a therapeutic to a patient whereby the therapeutic positively impacts the tissue to which it is targeted. Thus, as used herein, the term "administering", when used in conjunction with a nitrated lipid can include, but is not limited to, providing a nitrated lipid to a subject systemically by, for example, intravenous injection, whereby the therapeutic reaches the target tissue. "Administering" a composition may be accomplished by, for example, injection, oral administration, topical administration, or by these methods in combination with other known techniques. Administering may be self-administration, wherein the subject in need of such treatment administers a therapeutic or administering may be by a medical or other health care professional or a caretaker of the subject in need of such treatment.

The term "animal," "patient," or "subject" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviate the symptoms, or eliminate the disease, condition, disorder or a symptom or symptoms thereof.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, improve, prevent, inhibit, block or reverse an unwanted condition, disease or symptom of a patient as may be indicated by the particular embodiment. In part, embodiments of the present invention are directed to solid organ fibrosis, inflammatory disease, cardiovascular disease, renal disease, kidney failure, ischemic kidney injury, acute kidney injury (AKI), chronic kidney injury (CKI), chronic kidney disease (CKD), obesity associated chronic kidney disease, diabetic nephropathy, kidney fibrosis, focal segmental glomerulosclerosis (FSGS), including primary FSGS, and secondary FSGS, sickle cell nephropathy, glomerulonephritis (with and without nephrotic syndrome), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases.

A "therapeutically effective amount" or "effective amount" of a composition is a predetermined amount calculated to achieve the desired effect, i.e., to discourage, combat, ameliorate, improve, prevent, inhibit, block, or reverse an unwanted condition, disease or symptom of a patient as may be indicated by the particular embodiment. For example, a "therapeutically effective amount" as recited in a "method of treating" embodiment is a predetermined amount calculated to achieve the desired treatment effect, i.e., to discourage, combat, ameliorate, or improve an unwanted condition, disease or symptom. For example, a "therapeutically effective amount" as recited in a "method of preventing" embodiment is a predetermined amount calculated to achieve the desired treatment effect, i.e., to prevent or inhibit or block an unwanted condition, disease or symptom prior to its occurrence. The therapeutically effective amount may therefore be in an amount sufficient for a certain exposure of the compound in the patient. In part, embodiments of the present invention are directed to solid organ fibrosis, inflammatory disease, cardiovascular disease, renal disease, kidney failure, ischemic kidney injury, acute kidney injury (AKI), chronic kidney injury (CKI), chronic kidney disease (CKD), obesity associated chronic kidney disease, diabetic nephropathy, kidney fibrosis, focal segmental glomerulosclerosis (FSGS), including primary FSGS, and secondary FSGS, sickle cell nephropathy, glomerulonephritis (with and without nephrotic syndrome), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases. The activity contemplated by the present methods includes both medical therapeutic and/or prophylactic treatment, as appropriate. The specific dose of a compound administered according to this invention to obtain therapeutic and/or prophylactic effects will be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue (also referred to as "exposure").

The terms "treat," "treated," "treating," "ameliorate," "improve," or "promote" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms of the condition, disorder or disease; diminishment of the extent of the condition, disorder or disease; stabilization (i.e., not worsening) of the state of the condition, disorder or disease; maintain the condition, disorder or disease; delay in onset or slowing of the progression of the condition, disorder or disease; and remission (whether partial or total), whether detectable or undetectable, or enhancement or improvement of the condition, disorder or disease. Amelioration or promotion includes eliciting a clinically significant response without excessive levels of side effects.

Generally speaking, the term "tissue" refers to any aggregation of similarly specialized cells which are united in the performance of a particular function.

Methods of Treating a Disease

Various embodiments of the invention describe a method of treating a disease in a patient in the need thereof by administering a therapeutically effective amount of an activated fatty acid.

In some embodiments, the disease to be treated may be solid organ fibrosis, inflammatory disease, cardiovascular disease, renal disease, kidney failure, ischemic kidney injury, acute kidney injury (AKI), chronic kidney injury (CKI), chronic kidney disease (CKD), obesity associated chronic kidney disease, diabetic nephropathy, kidney fibrosis, focal segmental glomerulosclerosis (FSGS), including primary FSGS, and secondary FSGS, sickle cell nephropathy, glomerulonephritis (with and without nephrotic syndrome), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases.

In some preferred embodiments of the invention, the disease is focal segmental glomerulosclerosis (FSGS) or pulmonary arterial hypertension (PAH). In some preferred embodiments of the invention the disease is focal segmental glomerulosclerosis (FSGS). In some preferred embodiments the FSGS is primary FSGS. In some embodiments the FSGS is secondary FSGS.

In the various embodiments described above, a therapeutically effective amount of an activated fatty acid may be as a daily dose or a single dose within a range of a lower limit amount and an upper limit amount. In some embodiments, the lower limit amount is about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, or about 425 mg. In some embodiments, the upper limit amount is about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed.

For example, the range may be from about 75 mg to about 300 mg, about 100 mg to about 400 mg, about 100 mg to about 200 mg, about 100 mg to about 300 mg, from about 150 mg to about 350 mg, from about 25 mg to about 75 mg, or from about 225 to about 450 mg and so on. In some embodiments, the lower limit of the range of a therapeutically effective amount may be selected from about 25 mg, 50 mg, 75 mg, 100 mg, 125 mg, 150 mg, 175 mg or 200 mg. In some embodiments, the upper limit of the range of a therapeutically effective amount may be selected from about 450 mg, 425 mg, 400 mg, 375 mg, 350 mg, 325 mg, 300 mg or 275 mg.

In some embodiments, the therapeutically effective amount may be from about 25 mg to about 450 mg, about 25 mg to about 425 mg, about 25 mg to about 400 mg, about 25 mg to about 375 mg, about 25 mg to about 350 mg, about 25 mg to about 325 mg, about 25 mg to about 300 mg, about 25 mg to about 275 mg, about 25 mg to about 250 mg, about 25 mg to about 225 mg, about 25 mg to about 200 mg, about 25 mg to about 175 mg, or about 25 mg to about 150 mg. In some embodiments, the therapeutically effective amount may be from about 50 mg to about 450 mg, about 75 mg to about 450 mg, about 100 mg to about 450 mg, about 150 mg to about 450 mg, about 175 mg to about 450 mg, about 200 mg to about 450 mg, about 225 mg to about 450 mg, about 250 mg to about 450 mg or about 275 mg to about 450 mg.

In some embodiments of the invention, the therapeutically effective amount is from about 75 mg to about 300 mg. In some embodiments of the invention, the therapeutically effective amount is from about 100 mg to about 300 mg. In some embodiments of the invention, the therapeutically effective amount is from about 100 mg to about 200 mg. In some embodiments of the invention, the therapeutically effective amount is from about 150 mg to about 300 mg. In some embodiments of the invention, the therapeutically effective amount is about 150 mg. In some embodiments, the activated fatty acid is administered in an amount sufficient for an exposure of about 75 mg twice per day. In some embodiments, the activated fatty acid is administered in an amount sufficient for an exposure of about 150 mg once per day.

In some embodiments the therapeutically effective amount of an activated fatty acid is about 75 mg, 150 mg or 300 mg. In some embodiments the therapeutically effective amount of an activated fatty acid is about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg or about 300 mg. In some embodiments the therapeutically effective amount of an activated fatty acid is an amount sufficient for an exposure of about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg or about 300 mg.

In some embodiments of the invention, the activated fatty acid is 10-nitro-9(E)-octadec-9-enoic acid and the therapeutically effective amount is from about 75 mg to about 300 mg. In some embodiments of the invention, the activated fatty acid is 10-nitro-9(E)-octadec-9-enoic acid and the therapeutically effective amount is from about 100 mg to about 300 mg. In some embodiments of the invention, the activated fatty acid is 10-nitro-9(E)-octadec-9-enoic acid and the therapeutically effective amount is from about 100 mg to about 200 mg. In some embodiments of the invention, the activated fatty acid is 10-nitro-9(E)-octadec-9-enoic acid and the therapeutically effective amount is from about 150 mg to about 300 mg. In some embodiments of the invention, the activated fatty acid is 10-nitro-9(E)-octadec-9-enoic acid and the therapeutically effective amount is about 150 mg.

In some embodiments, the activated fatty acid is 10-nitro-9(E)-octadec-9-enoic acid and the therapeutically effective amount is about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg or about 300 mg. In some embodiments, the therapeutically effective amount of the 10-nitro-9(E)-octadec-9-enoic acid is an amount that sufficient for an exposure of about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg or about 300 mg.

In some embodiments, the therapeutically effective amount as described above may be administered once per day. In some embodiments, the therapeutically effective amount as described above may administered in equal amounts twice per day. In some embodiments, the therapeutically effective amount as described above may administered in equal amounts three times per day. In some embodiments, the therapeutically effective amount as described above may administered in equal amounts four times per day.

In some embodiments, the therapeutically effective amount of an activated fatty acid is as a single dose, which is administered once per day or multiple times per day. For example, the above mentioned single dose may be administered as a single dose two times per day, three times per day or four times per day.

In some embodiments of the invention, the activated fatty acid is 10-nitro-9(E)-octadec-9-enoic acid and the therapeutically effective amount is in an amount sufficient for an exposure of about 75 mg to about 300 mg administered once per day. In some embodiments of the invention, the activated fatty acid is 10-nitro-9(E)-octadec-9-enoic acid and the therapeutically effective amount is in an amount sufficient for an exposure of about 100 mg to about 300 mg administered once per day. In some embodiments of the invention, the activated fatty acid is 10-nitro-9(E)-octadec-9-enoic acid and the therapeutically effective amount is in an amount sufficient for an exposure of about 100 mg to about 200 mg administered once per day. In some embodiments of the invention, the activated fatty acid is 10-nitro-9(E)-octadec-9-enoic acid and the therapeutically effective amount is in an amount sufficient for an exposure of about 150 mg to about 300 mg administered once per day. In some embodiments of the invention, the activated fatty acid is 10-nitro-9(E)-octadec-9-enoic acid and the therapeutically effective amount is in an amount sufficient for an exposure of about 150 mg administered once per day. In some embodiments, the 10-nitro-9(E)-octadec-9-enoic acid is administered in an amount sufficient for an exposure of about 75 mg twice per day.

In some embodiments the activated fatty acid is 10-nitro-9(E)-octadec-9-enoic acid and the therapeutically effective amount is about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg or about 300 mg administered once per day. In some embodiments the activated fatty acid is 10-nitro-9(E)-octadec-9-enoic acid and the therapeutically effective amount is in an amount sufficient for an exposure of about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg, or about 300 mg administered once per day. In some embodiments the activated fatty acid is 10-nitro-9(E)-octadec-9-enoic acid and the therapeutically effective amount is in an amount sufficient for an exposure of about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 155, about 160 mg, about 165 mg, about 170 mg, about 175 mg, about 180 mg, about 190 mg, about 200 mg, about 205 mg, about 210 mg, about 220 mg, about 225 mg, about 230 mg, about 235 mg, about 240 mg, about 250 mg, about 255 mg, about 260 mg, about 265 mg, about 270 mg, about 275 mg, about 280 mg, about 285 mg, about 290 mg, or about 300 mg administered twice per day. In some embodiments, the 10-nitro-9(E)-octadec-9-enoic acid is administered in an amount sufficient for an exposure of about 75 mg twice per day. In some embodiments, the 10-nitro-9(E)-octadec-9-enoic acid is administered in an amount sufficient for an exposure of about 150 mg once per day.

In yet other embodiments, a therapeutically effective amount of an activated fatty acid may vary as treatment progresses. For example, the daily dose (or dosing regimen) may be increased or decreased as treatment proceeds through administration cycles, or the daily dosage may increase or decrease throughout administration.

The activated fatty acids of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intranasally, intravaginally, by inhalation, by depot injections, or by implants. In certain embodiments, the activated fatty acids are administered orally. In certain embodiments, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including an activated fatty acid may be deposited to a site of injury or inflammation, such as, for example, the site of a surgical incision or a site of inflammation due to arthroscopy, angioplasty, stent placement, by-pass surgery and so on.

In certain other embodiments, the activated fatty acids of the invention may be applied locally as a salve or lotion applied directly to an area of in need of treatment. For example, in some embodiments, a lotion or salve including activated fatty acids of the invention may be prepared and applied to a burn, radiation burn, site of dermal disorder, edema, arthritic joint or the like.

Various embodiments of the invention are also directed to a method for administering activated fatty acids. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

In some embodiments, the treatment regimen as described above may be combined with a secondary form of treatment or a secondary agent.

As used herein an "activated fatty acid" refers to a fatty acid having at least one electron withdrawing group covalently bound to a carbon of the saturated or unsaturated aliphatic chain of a fatty acid. Such activated fatty acids may be substituted by any number of electron withdrawing groups at any number of positions on the hydrocarbon chain and such electron withdrawing groups may or may not be associated with a carbon-carbon double bond. Similarly, the activated fatty acids described herein may include any number of double bonds which may or may not be associated with an electron withdrawing group. However, in the various embodiments of the invention, at least one double bond of an activated fatty acid may be associated with an electron withdrawing group. In such embodiments, the electron withdrawing group may be positioned in either cis or trans configuration at a double bond or in either R or S absolute stereochemistry at an sp chiral/stereogenic center. For example, in some embodiments, the activated fatty acids may have one electron withdrawing group, and in other embodiments, the activated fatty acids may be substituted with multiple electron withdrawing groups at multiple positions along the hydrocarbon chain.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ ($\sigma$[P]) is about −0.7 and the $\sigma$[P] for a para substituted nitro group is about 0.8. Embodiments of the invention encompass any known electron withdrawing group. For example, electron-withdrawing groups may include, but are not limited to, formyl (—COH), acyl (—COR), carbonyl (—CO), carboxyl (—COOH), carboxylate (—COOR), halo (—Cl, —F, —Br, etc.), fluoromethyl (—$CF_n$), cyano (—CN), sulfinyl (—SO), sulfonyl (—$SO_2R$), sulfonic (—$SO_3H$), 1°, 2° and 3° ammonium (—$NR_3^+$), and nitro (—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a $\sigma$ of at least about 0.2, and in certain embodiments, the electron withdrawing group may form a dipole. For example, in particular embodiments, the electron withdrawing group may be a nitro, ammonium or sulfonyl. In other embodiments, the activated fatty acids of the invention may be additionally substituted by non-electron withdrawing groups or electron donating groups including, for example, hydroxyl (—OH), carboalkoxy (—OOCR), alkyl, alkenyl, alkynyl, 1° and 2° amines (—$NR_2$), nitrate (—$ONO_2$), nitrito (—ONO) and the like.

The activated fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring activated fatty acids are generally unbranched and contain an even number of from about 4 to about 24 carbons, and others include fatty acids having from 12 to 18 carbons in the aliphatic hydrocarbon chain. In still other embodiments, activated fatty acids may have greater than 24 carbons in the aliphatic hydrocarbon chain. Embodiments of the invention encompass such naturally occurring activated fatty acids as well as non-naturally occurring activated fatty acids, which may contain an odd number of carbons and/or a non-naturally occurring linker. Thus, some embodiments of the invention include activated fatty acids having an odd number of carbons of, for example, from 5 to 23 carbons, and in other embodiments, from 11 to 17 carbons. In yet other embodiments, the activated fatty acids of embodiments may have greater than 23 carbons. The naturally and non-naturally occurring activated fatty acids of the invention may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of the activated fatty acids of various embodiments may be unsaturated or polyunsaturated. The term "unsaturated" refers to a fatty acid having a aliphatic hydrocarbon chain that includes at least one double bond in the chain or on as a substituent. In contrast, a "saturated" hydrocarbon chain does not include any double bonds or double bond substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is actually an E nitroalkene. Similarly, the nitroalkene analog of a "trans" double bond is actually a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments of the invention may include activated fatty acids having double bonds in either cis or trans configuration, and encompass compositions that may include combinations of cis and trans containing activated fatty acids and regioisomers of the activated fatty acids.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega ($\omega$)-3, $\omega$-5, $\omega$-6, $\omega$-7, $\omega$-9 fatty acids and the like. Any such activated fatty acid may be useful in embodiments of the invention. The symbol '$\omega$' is used to refer to the terminal methyl carbon of the aliphatic hydrocarbon chain. The placement of the double bond of the $\omega$-X fatty acid is the carbon-carbon bond X number of carbons from the $\omega$ carbon. For example, an $\omega$-6 fatty acid has a double bond between the $6^{th}$ and $7^{th}$ carbons from the $\omega$ carbon and an $\omega$-3 fatty acid has a double bond between the $3^{rd}$ and $4^{th}$ carbons from the $\omega$ carbon. Various embodiments of the invention include nitrated $\omega$-3 fatty acids, including, but not limited to, the nitrated forms of linolenic acid, alpha-linolenic acid, eicosapentanoic acid, docosapentaenoic acid, docosahexanoic acid and stearidonic acid; nitrated $\omega$-5 fatty acids including, but not limited to, nitrated forms of myristoleic acid; nitrated $\omega$-6 fatty acids including, but not limited to, nitrated forms of linoleic acid, gamma-linoleic acid, dihomo-gamma-linoleic acid and arachidonic acid; nitrated ω-7 fatty acids including, but not limited to, nitrated palmitoleic acid; and nitrated ω-9 fatty acids including, but not limited to, nitrated oleic acid and erucic acid. Alternatively, the activated fatty acids of the invention may also be referred to using IUPAC nomenclature in which the placement of the double bond is determined by counting from the carbon of the carboxylic acid, and 'CX' denotes the carbon number in aliphatic hydrocarbons using IUPAC nomenclature wherein X is the number of the carbon atom from the carboxylic acid. Embodiments of the invention also include synthetic equivalents to naturally occurring fatty acids and derivatives thereof.

The activated fatty acids of the invention may have an electron withdrawing group positioned at any carbon along the aliphatic hydrocarbon chain between the carboxy terminal carbon to the terminal methyl. In some embodiments, the electron withdrawing group may be positioned within about 1 carbon from the carboxy terminal carbon and within about 1 carbon from the terminal methyl. In other embodiments, the electron withdrawing group may be positioned within about 3 carbons of either the carboxy terminal carbon and/or the methyl terminal carbon, and in still others embodiments, the electron withdrawing group may be positioned within 5 carbons of either of the carboxy terminal carbon and/or the methyl terminal carbon.

In certain embodiments, the electron withdrawing group may be positioned on a carbon directly attached to a double bond of the activated fatty acid forming an "electron withdrawing alkenyl" group. The electron withdrawing group of such alkenyl groups may be on either side of the double bond. Activated fatty acids encompassed by embodiments of the invention may have one or more than one electron withdrawing alkenyl groups at any carbon on the aliphatic hydrocarbon chain. In some embodiments, an unsaturated fatty acid can have one electron-withdrawing group. For example, an activated oleic acid (ocatadecac-9-enoic acid) which is an 18 carbon, ω-6 fatty acid with one double bond (denoted "18:1") between the $6^{th}$ (C-13) and $7^{th}$ (C-12) carbons, may have an electron withdrawing group at either C-13 or C-12. In another exemplary embodiment, an activated linoleic acid (octadeac-9, 12,-dienoic acid), which is an 18 carbon, ω-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at C-9 or C-10 or C-12 or C-13. Similarly, other polyunsaturated fatty acids, with 3, 4, 5, 6 or more double bonds, can have one electron withdrawing at either position on any of the double bond carbons, including all possible permutations of positions and electron-withdrawing groups.

In other embodiments, a mono or polyunsaturated fatty acid may have two electron-withdrawing groups. For example, in one embodiment, an activated oleic acid (ocatadecac-9-enoic acid), which is an 18 carbon, ω-6 fatty acid with one double bond (denoted "18:1") between the $6^{th}$ (C-13) and $7^{th}$ (C-12) carbons, may have an electron withdrawing group at both C-13 and C-12. In another exemplary embodiment, an activated linoleic acid (octadeac-9,12,-dienoic acid), which is an 18 carbon, ω-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at any two of the positions C-9, C-10, C-12 or C-13, with the following possible permutations: C-9 and C-10, C-9 and C-12, C-9 and C-13, C-10 and C-12, C-10 and C-13, or C-12 and C-13.

In analogy to the preceding descriptions of compounds with one electron-withdrawing group or two electron-withdrawing groups, it is also possible to have three, four, five or more electron withdrawing groups. Following the same logic above, in the preceding descriptions of compounds with one electron-withdrawing group or two electron-withdrawing groups, polyunsaturated fatty acids, with 3, 4, 5, 6 or more double bonds, can have multiple electron withdrawing (three, four, five or more, as available positions for substitution permit) at any of the positions on any of the double bond carbons, including all possible permutations of positions and electron-withdrawing groups. Additionally, in any embodiments such as those described above, any number of non-electron-withdrawing groups may be covalently bound to carbons of the aliphatic chain of the activated fatty acid. For example, in some embodiments, the activated fatty acids of the invention may include one or more methyl, $C_2$-$C_6$ alkyl, alkenyl, or alkynyl or amino covalently attached to one or more carbons of the aliphatic chain of an activated fatty acid.

Other embodiments of the invention include unsaturated or polyunsaturated non-naturally occurring activated fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring activated fatty acids may include one or more linker groups, which interrupt the aliphatic hydrocarbon chain. Linkers include, but are not limited to carboxyl, oxygen, alkenyloxy, amino, imino and the like at any position within the aliphatic hydrocarbon chain.

Various embodiments of the invention include unsaturated or polyunsaturated activated fatty acids that may have a carbon-carbon double bond between any two carbons of the aliphatic chain of the fatty acid, and any number of carbon-carbon double bonds may be present in such polyunsaturated fatty acids. For example in some embodiments, polyunsaturated activated fatty acids may have 2, 3, 4, 5, 6 or more carbon-carbon double bonds. In such embodiments, each of the more than one carbon-carbon double bond may individually be in either cis or trans configuration. In some embodiments, at least one of the carbon-carbon double bonds of a polyunsaturated activated fatty acid may have an associated electron withdrawing group, and in other embodiments, more than one of the carbon-carbon double bonds of such polyunsaturated activated fatty acids may have an associated electron withdrawing group. Additionally, in such embodiments, the electron withdrawing group may be associated with either carbon of the carbon-carbon double bond or a carbon directly adjacent to either carbon of the carbon-carbon double bond. For example, in some embodiments, an electron withdrawing group may be attached to the carbon alpha (α) to a carbon-carbon double bond, and in other embodiments, an electron withdrawing group may be attached to the carbon beta (β) to a carbon-carbon double bond. In still other embodiments, an electron withdrawing group may be attached to the carbon gamma (γ) to a carbon-carbon double bond, or the electron withdrawing group may be attached to a carbon-carbon double bond. In embodiments where a polyunsaturated activated fatty acid includes two or more carbon-carbon double bonds along the aliphatic chain and an electron withdrawing group is associated with any of the two or more carbon-carbon double bonds or each of the two or more of the carbon-carbon double bonds, each electron withdrawing group may be attached to any carbon associated with each individual carbon-carbon double bonds. For example, in some embodiments, an electron withdrawing group may be associated with each of the double bonds, with the electron group attached to either the carbon alpha (α), the carbon beta (β) or the carbon gamma (γ) to each double bond. In other embodiments, some of the double bonds can have an attached electron withdrawing group and some of the double bonds will not have attached electron withdrawing groups, and those double bonds that do have attached electron withdrawing groups can have electron withdrawing groups attached at the carbon alpha (α), the carbon beta (β) or the carbon gamma (γ) to each double bond.

In particular embodiments, an unsaturated activated fatty acid having at least one electron withdrawing group may be a conjugated fatty acid. In such embodiments, two carbon-carbon double bonds in an aliphatic chain are adjacent to one another such that there is no methylene group between them. Such conjugated compounds are commonly called 1,3-dienes, or conjugated fatty acids. Such 1,3-dienes may include one or more electron withdrawing groups at any of 6 positions, at the 1, 2, 3, and/or 4 positions of the 1,3-dienes and at the two carbons adjacent to the diene (at the 0 and 5 positions, in relation to the 1, 2, 3, 4 method of identifying carbons in a 1,3-diene). For example, one associated electron withdrawing group may be attached to any of the 6 positions identified above, that is to either the 1, 2, 3, or 4 positions on the diene or to either of the carbons adjacent to the 1,3-diene (at the 0 or 5 positions, as described above). In additional embodiments, two associated electron withdrawing groups may be attached to any two of the six possible positions, three associated electron withdrawing groups could be attached to any two of the six possible positions, four associated electron withdrawing groups could be attached to any two of the six possible positions, five associated electron withdrawing groups could be attached to any two of the six possible positions, and six associated electron withdrawing groups could be attached to any two of the six possible positions. In summary, any configuration of electron withdrawing groups attached to any of the six positions described above in a 1,3-diene are encompassed by embodiments of the invention.

In certain embodiments, the activated fatty acids of the invention may undergo an isomerization following preparation such that either the cis/trans configuration of the double bond, the location of the double bond in the carbon chain, or both, may change. For example, in some embodiments, an activated fatty acid may be prepared with a carbon-carbon double bond having an electron withdrawing group attached to a carbon gamma to a carbon-carbon double bond. Following preparation, the carbon-carbon double bond may undergo an isomerization such that the electron withdrawing group is now conjugated with the carbon-carbon double bond after isomerization. Such isomerizations may occur spontaneously at any time following preparation, and may result in a composition which may have initially been prepared as including a single species of activated fatty acid that subsequently includes a combination of isomers of the first-prepared activated fatty acid originally produced. In other embodiments, an activated fatty acid may be prepared having an electron withdrawing group attached to a gamma carbon of a carbon-carbon double bond, and this carbon-carbon double bond may undergo an isomerization following administration such that an activated fatty acid is produced having the electron withdrawing group is conjugated with the carbon-carbon double bond.

In still other embodiments, the carboxy-terminal end of the activated fatty acid may be modified. For example, in some embodiments, the activated fatty acid may include a glycerol associated with the carboxy-terminal end of the activated fatty acid to create a glycerolipid, and such glycerolipids may be mono-, di-, or tri-glycerides wherein at least one of the fatty acids of a di- or tri-glyceride may be an activated fatty acid and any remaining fatty acids may be a saturated or unsaturated fatty acid. Similarly, in other embodiments, a carbohydrate may be associated with the carboxy-terminal end of an activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of an activated fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, hydroxyl (forms an alcohol), amino (forms an amine), phosphonooxyl (forms a phosphate), phosphono (forms a phosphonic acid), thio (forms a thiol), sulfo (forms a sulfoic acid) and the like. In certain embodiments, the carboxy-terminal end of the activated fatty acids of the invention may be associated with a phosphate to from a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one activated fatty acid is attached to the glycerol, remaining positions on the glycerol may include a saturated or unsaturated fatty acid or hydrogen, alkyl, or a functional group such as, for example, hydroxyl (forms an alcohol), amino (forms an amine), phosphonooxyl (forms a phosphate), phosphono (forms a phosphonic acid), thio (forms a thiol), sulfo (forms a sulfoic acid) and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In these particular embodiments, carboxy-terminal modifications on fatty acids including a glycerol may not include a nitro group. Without wishing to be bound by theory, modification of the carboxy-terminal end of activated fatty acids may enhance partitioning of the activated fatty acid after administration and may also improve resilience of the activated fatty acid by inhibiting beta-oxidation in mitochondria following administration.

For example, embodiments of the invention include compounds of general formula I and II:

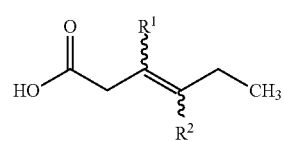

I

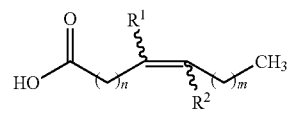

II wherein $R^1$ and $R^2$ are independently selected from hydrogen and any electron withdrawing groups including, but not limited to —COH, —COR, —CO, —COOH, —COOR, —Cl, —F, —Br, —I, —CF$_3$, —CN, —SO$_3^-$, —SO$_2$R, —SO₃H, —NH₃⁺, —NH₂R⁺, —NHR₂⁺, —NR₃⁺ and —NO₂⁻ wherein at least one of R¹ and R² is an electron withdrawing group, R is C₁-C₁₀ alkyl, and m and n are, independently, 1-20. Some embodiments include compounds of general formula III:

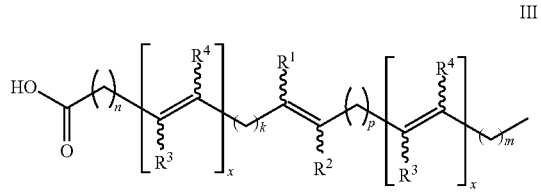

wherein R¹, R², m and n are as described above, R³ and R⁴ are, independently, selected from —H, —COH, —COR, —CO, —COOH, —COOR, —Cl, —F, —Br, —I, —CF₃, —CN, —SO₃⁻, —SO₂R, —SO₃H, —NH₃⁺, —NH₂R⁺, —NHR₂⁺, —NR3⁺ and —NO₂⁻, R is C₁-C₁₀ alkyl, k and p are, independently, 0 to 5 and x and y are independently, 0 to 3, and wherein each double bond is in either cis or trans configuration. In still other embodiments, any carbon associated with m, n, k or p may be substituted.

Compounds encompassed by the formula described above include, but are not limited to, (E)-9-nitro-octadec-9-enoic acid, (E)-10-nitro-octadec-9-enoic acid, (E)-8-nitro-octadec-9-enoic acid, (E)-11-nitro-octadec-9-enoic acid, (E)-10-acetyltetradec-9-enoic acid, (E)-9-acetyltetradec-9-enoic acid, (E)-11-acetyltetradec-9-enoic acid, (E)-8-acetyltetradec-9-enoic acid, (E)-13-chloro-docosen-13-enoic acid, (E)-14-chloro-docosen-13-enoic acid, (E)-12-chloro-docosen-13-enoic acid, (E)-15-chloro-docosen-13-enoic acid, (E)-10-methylsulfonylhexadec-9-enoic acid, (E)-9-methylsulfonylhexadec-9-enoic acid, (E)-11-methylsulfonylhexadec-9-enoic acid, and (E)-8-methylsulfonylhexadec-9-enoic acid. Other embodiments include the Z-isomer of such compounds. Further embodiments include, for example, (E)-9-nitro-pentadec-9-enoic acid, (E)-10-nitro-pentadec-9-enoic acid, (E)-8-nitro-pentadec-9-enoic acid, (E)-11-nitro-pentadec-9-enoic acid, (E)-10-acetylheptadec-9-enoic acid, (E)-9-acetylheptadec-9-enoic acid, (E)-11-acetyloctahepta-9-enoic acid, (E)-8-acetylheptadec-9-enoic acid, (E)-10-chloro-pentadec-9-enoic acid, (E)-9-chloro-pentadec-9-enoic acid, (E)-11-chloro-pentadec-9-enoic acid, (E)-8-chloro-pentadec-9-enoic acid, (E)-10-methylsulfonylnonadec-9-enoic acid, (E)-9-methylsulfonylnonadec-9-enoic acid, (E)-11-methylsulfonylnonadec-9-enoic acid, (E)-8-methylsulfonylnonadec-9-enoic acid, and the (Z)-isomers thereof. Yet other embodiments include, for example, (E)-9-nitro-eicos-11,14-ienoic acid, (E)-10-nitro-eicos-8,13-ienoic acid, (E)-8-nitro-eicos-11,14-ienoic acid, (E)-11-nitro-eicos-8,13-ienoic acid, (E)-10-acetylnonadec-10,13-ienoic acid, (E)-9-acetylnonadec-9,12-enoic acid, (E)-11-acetylnonadec-10,13-ienoic acid, (E)-8-acetylnonadec-9,12-enoic acid, (E)-10-chloro-heptadec-9,11-ienoic acid, (E)-9-chloro-hetpadec-10,12-ienoic acid, (E)-11-chloro-heptadec-9,11-ienoic acid, (E)-8-chloro-heptadec-10,11-ienoic acid, (E)-10-methylsulfonylpentadec-9,11-ienoic acid, (E)-9-methyl sulfonylpentadec-8,9-ienoic acid, (E)-11-methylsulfonylpentadec-9,10-ienoic acid, and (E)-8-methylsulfonylpentadec-8,9-ienoic acid, and (Z)-isomers thereof. As indicated by the list above, activated fatty acids of any length with any number of carbon-carbon double bonds are any position along the aliphatic chain can be prepared and are encompassed by the invention.

Activated fatty acids also include keto fatty acids such as those defined by Formula IV.

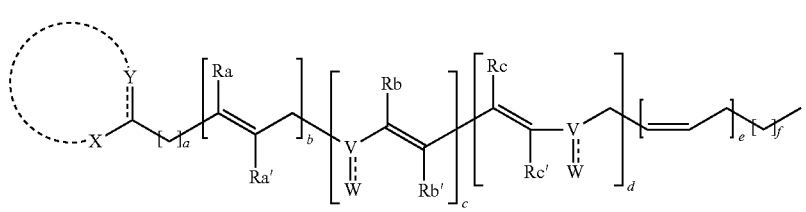

wherein, X is selected from the group consisting of —CH₂—, —OH, —S, —OR^P and —NR^P R^q; Y is —C(O)—, O, —S—, and —NR^P R^q; W is —OH, —H, =S, —SR^P, —C(O)H, —C(O), —C(O)R^P, —COOH, —CO-OR^P, —Cl, —Br, —I, —F, —CF₃, —CN, —SO₃, —SO₂R^P, —SO₃H, —NH₃⁺, —NH₂RP⁺, —NR^P R^q R¹, NO₂, =O, =NRP, =CF₂, and =CHF and V is —CH— when W is —OH, —H, —C(O)H, —C(O), —C(O)R^P, —COOH, —COOR^P, —Cl, —Br, —I, —F, —CF₃, —CN, —SO₃, —SO₂R^P, —SO₃H, —NH₃⁺, —NH₂R^P⁺, —NR^P R^q R^t and NO₂ and V is —C— when W is =O, =NR^P, =CF₂, and =CHF.

In Formula IV, a, b, c, d, e, and f may each, independently, be integers between 0 and 15. In some embodiments, when c is 0, d is not 0. Alternatively, in some embodiments, when d is 0, c is not 0. Thus, in various embodiments of the invention, activated fatty acids of Formula IV may have at least one c or at least one d. In particular embodiments, a and f may be 2 to 15, 3 to 10, 5 to 9, or any range or individual integer encompassed by these example ranges. In some embodiments, b and e may each individually be 1 to 5, and, in some embodiments, b and e may each individually be 2 or 3.

In some embodiments, substituents R^P, R^q and R^t are independently selected from H, (C₁-C₈)alkyl and (C₁-C₈) haloalkyl. In some embodiments, substituents R^a, R^a', R^b, R^b', R^c, R^c', are each independently —H, —OH, —C(O)H, —C(O), —C(O)R^P, —COOH, —COOR^P, —Cl, —Br, —I, —F, —CF₃, —CHF₂, —CH₂F, —CN, —SO₃, —SO₂R^P, —SO₃H, —NH₃⁺, —NH₂R^P⁺, —NR^P R^q R^t and NO₂. Additionally, in some embodiments, R^a and R^a' do not simultaneously represent non-hydrogen groups; R^b and R^b' do not simultaneously represent non-hydrogen groups; and, similarly, R^c and R^c' do not simultaneously represent non-hydrogen groups.

In Formula IV, an optional double bond is indicated by ====, while

when present, together with X and Y and the carbon atom to which they are bonded represents a 5- to 6-membered heterocyclyl or heteroaryl ring.

Further embodiments include compounds of Formulae V-VIII:

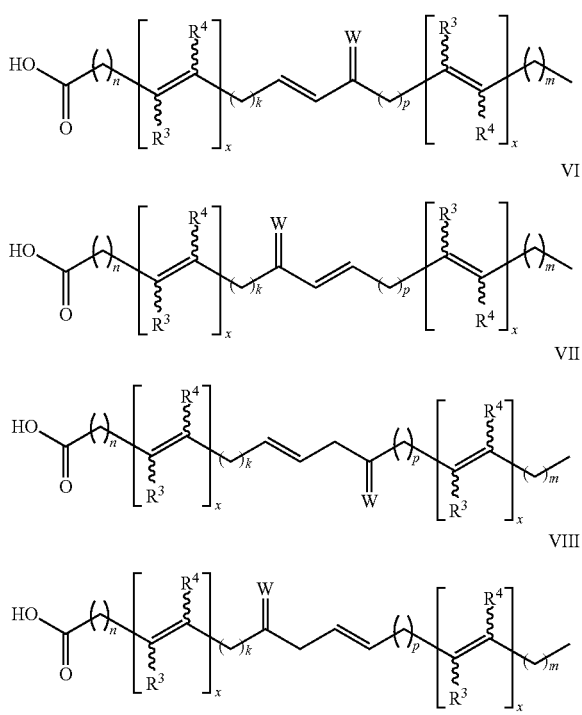

In each of Formulae V-VIII, each $R^3$ and each $R^4$ may be independently, selected from —H, —COH, —COR, —CO, —COOH, —COOR, —Cl, —F, —Br, -1, —CF$_3$, —CN, —SO$_3^-$, —SO$_2$R, —SO$_3$H, —NH$_3^+$, —NH$_2$R$^+$, —NHR$_2^+$, —NR3$^+$ and —NO$_2^-$; m, n, k, and p are, independently, 0 to 5; x and y are independently, 0 to 3; W is =O, =NR$^P$, =CF$_2$, and =CHF; R is C$_1$-C$_{10}$ alkyl; and each double bond is in either cis or trans configuration. In still other embodiments, any carbon associated with m, n, p, or k can be substituted.

In certain embodiments, the activated fatty acids may be 13-oxo-(7Z,10Z,14A,16Z,19Z)-docosa-7,10,14,16,19-pentaneoic acid, 17-oxo-(7Z,10Z,13Z,15A,19Z)-docosa-7,10,13,15,19-pentanoeic acid, 13-OH (7Z,10Z,14A,16Z,19Z)-docosa-7,10,14,16,'19-pentaneoic acid, 17-OH (7Z,10Z,13Z,15A,19Z)-docosa-7,10,13,15,19-pentaneoic acid, 13-oxo-(4Z,7Z,10Z,14A,16Z,19Z)-docosa-4,7,10,14,16,19-hexaneoic acid, 17-oxo-(4Z,7Z,10Z,13Z,15A,19Z)-docosa-4,7,10,13,15,19-hexaneoic acid, 13-OH-(4Z,7Z,10Z,14A,16Z,19Z)-docosa-4,7,10,14,16,19-hexaneoic acid or 17-OH-(4Z,7Z,10Z,13Z,15A,19Z)-docosa-4,7,10,13,15,19-hexaneoic acid where A indicates either E or Z configuration.

In certain embodiments described herein, the activated fatty acid is a nitro fatty acid. In certain embodiments described herein, the activated fatty acid is a nitro oleic acid, also referred to as OA-NO$_2$. In certain embodiments described herein, the activated fatty acid is a 10-nitro-oleic acid, also known as CXA-10 and 10-nitro-9(E)-octadec-9-enoic acid, which has the following structure:

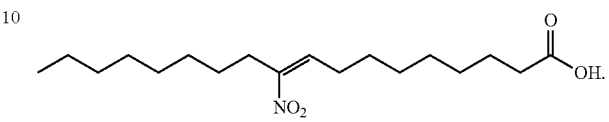

In certain embodiments, the activated fatty acids described above may include various moieties associated with the carboxyl terminus of activated fatty acids, such as, for example, sugars, cholesterol, phosphates, sphingo bases, and the like. Therefore, activated fatty acids of embodiments herein may encompass, for example, glycolipid, glycerolipid, phospholipid, sphingolipid, and cholesterol ester derivatives of the activated fatty acids described above. In other embodiments, the carboxyl terminus of the activated fatty acids may be modified to include, for example, a heterocylic ring.

The activated fatty acids of various embodiments may be prepared by any method known in the art. For example, in one embodiment, an activated fatty acid may be prepared by contacting an unsaturated fatty acid with a mercuric salt and a selenium compound to from a first intermediate; contacting the first intermediate with a reagent or reactant that can introduce an electron withdrawing group to form a second intermediate; and contacting the second intermediate with an oxidizing agent.

Without wishing to be bound by any theory, a selenium compound, such as, for example, PhSeBr, PhSeCl, PhSeO$_2$CCF$_3$, PhSeO$_2$H, PhSeCN and the like, may react with one or more carbon-carbon double bonds of the unsaturated fatty acid to form a three-membered ring intermediate on the fatty acid in a reaction that may be facilitated by the mercuric salt such as, for example, HgCl$_2$, Hg(NO$_3$)$_2$, Hg(OAc)$_2$ and the like as depicted in step I of the reaction below:

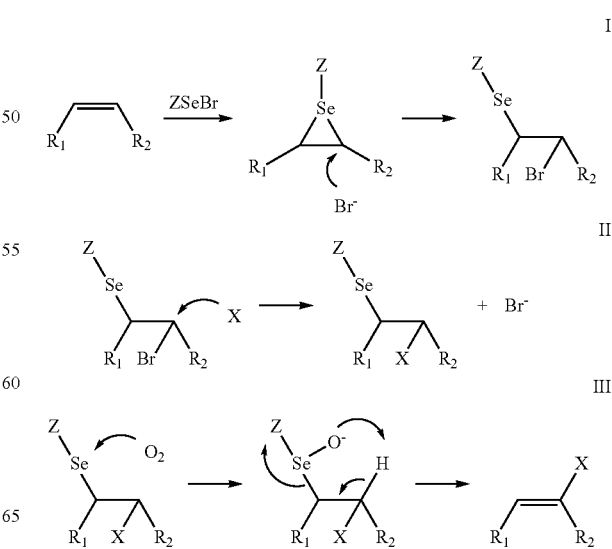

The source of the electron withdrawing group may be any compound known in the art that is capable of generating an electron withdrawing group that can be incorporated into the activated fatty acid, such as, for example, $NaNO_2$, $AgNO_2$, $HSO_2OH$, and the like. Without wishing to be bound by theory, the electron withdrawing group (X in the reaction scheme above) may become joined to the hydrocarbon chain by displacing, for example, the bromine that was associated with the selenium compound as depicted in step II of the reaction scheme provided above. It is noted that the electron withdrawing groups may also react directly with the three-membered ring episelenonium ion shown in step I at the position where the bromine is shown as attacking. Finally, as depicted in step III of the reaction scheme provided above, the oxidizing agent forms a reactive selenium-oxo functional group, which undergo molecular rearrangement and elimination of ZSeOH leading to formation of the electron withdrawing alkenyl (depicted as a nitro alkenyl) on the hydrocarbon chain. Z in the reaction scheme above may be any number of groups. For example, in certain embodiments, Z may be a phenyl group.

In other embodiments, an activated fatty acid may be prepared using a modified aldol condensation such as the Henry reaction. A review of the Henry reaction and methods related to the Henry method can be found, for example, in Frederick A. Luzzio, F. A. "The Henry reaction: recent examples" Tetrahedron 2001, 57, 915-945 which is hereby incorporated by reference in its entirety. Known variations of the Henry reaction may also be useful in preparing activated fatty acids and all such methods are embodied herein. For example, in some embodiments, variations of the Henry reaction including, but not limited to, the Wittig-like variation of the Henry reaction, the Horner-Wadsworth-Emmons variation of the Henry reaction, and the Peterson-olefination variation of the Henry reaction. In such methods, double bonds are formed using the assistance of groups temporarily included in the reactants but that do are not included in the product. For example, the Wittig reaction uses phosphorus ylides to aid in the condensation reactions with carbonyls and in the dehydration reaction to form alkenes. The Horner-Wadsworth-Emmons reaction uses phosphonate esters, and the Peterson olefination uses silicon reagents for the condensation and dehydration steps. A review of major alkene-forming name reactions by reaction of a functionalized reagent with a carbonyl compound including the Wittig reaction, Horner-Wittig, Horner-Wadsworth-Emmons can be found, for example, in Peterson, Johnson, and Julia reactions. Blakemore, P. R. "The modified Julia olefination: alkene synthesis via the condensation of metallated heteroarylalkylsulfones with carbonyl compounds J Chern. Soc., Perkin Trans. 1, 2002, 2563-2585, which is hereby incorporated by reference in its entirety.

The Henry "nitro-aldol" reaction is the condensation of a nitroalkane with either an aldehyde or a ketone carbonyl containing compound to form a nitro-aldo product with the newly-formed beta-hydroxynitroalkyl group. Dehydration (loss of water) from nitro-aldol products leads to the formation of nitroalkenes. There are many methods to perform the nitroalkane-carbonyl condensation reaction to make nitro-aldols and there are many methods for the dehydration reaction to form nitroalkenes. Examples of such methods can be found in, for example, Woodcock, S. R.; Marwitz, A. J. V. Bruno, P.; Branchaud, B. P. "Synthesis of Nitrolipids. All Four Possible Diastereomers of Nitrooleic Acids: (E)- and (Z)-, 9- and 10-Nitro-octadec-9-enoic Acids" Organic Letters, 2006, 8, 3931-3934, which provides one regioisomer and usually one of two possible alkene cis/trans or Z/E diastereomers, in high purity and usually in high chemical yield, which is hereby incorporated by reference in its entirety.

Enantioselective Henry reactions are also possible and may require the use of one or more catalysts for the reaction, and embodiments of the invention, include the use of such methods to prepare stereospecific isomers of nitroalkenes. For example, Boruwa, J.; Gogoi, N.; Saikia, P. P.; and Barua, N. C. "Catalytic Asymmetric Henry Reaction" Tetrahedron: Asymmetry 2006, 17, 3315-3326, which is hereby incorporated by reference in its entirety, describes methods for preparing stereospecific isomers of nitroalkenes.

In still other embodiments, alkenes (olefins) may be prepared by metal-mediated cross coupling reactions (joining together of two molecules to make one new molecule) by condensation onto a carbonyl compound. Such methods have not been applied to the formation of nitroalkenes or to the formation of other alkenes with electron-withdrawing substituents, but such methods could be adapted to the synthesis of alkenes with electron-withdrawing substituents. For example, named cross coupling reactions such as the Heck, Suzuki and Stille coupling, along with others may be used to prepare activated fatty acids. Such methods are well known in the art. A review of such reactions of can be found in, for example, Metal-Catalyzed Cross-Coupling Reactions de Meijere, Armin/Diederich, Francois (eds.) Wiley-VCH, Weinheim 2004. XXII, ISBN-10: 3-527-30518-1 and ISBN-13: 978-3-527-30518-6 which are hereby incorporated by reference in their entireties.

Examples of various embodiments of methods for preparing activated fatty acids may at least include the following steps:

i) combining a first component at least including an aliphatic hydrocarbon having an electron withdrawing group at one end with an second component including aliphatic hydrocarbon chain having an aldehyde at one end in the presence of a base to form a first intermediate; and ii) generating an alkene from the first intermediate. Exemplary reactions are presented in schemes I and II below:

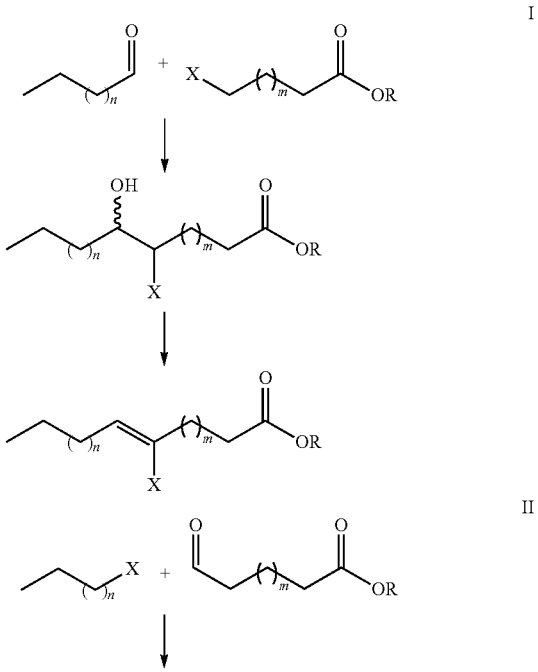

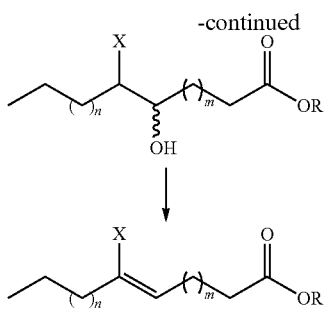

In reaction schemes I and II, the variable X represents an electron withdrawing group and can be any electron withdrawing group discussed herein above or known in the art. The variables n and m represent a number of carbon atoms in the aliphatic hydrocarbon chain, and n and m can be any number. For example, the aliphatic hydrocarbon chains of any of the starting compound may be from 2-20 carbons in length. Moreover, the position of the double bond and the arrangement of the electron withdrawing group in relation to the double bond may be determined specifically, and particular activated fatty acids may be created in high yield. For example, an oleic acid may be produced by the reaction of scheme I by combining a first substrate where m is 6 and a second substrate where n is 6.

Any activated fatty acid may be produced using the method presented above, and both naturally-occurring and non-naturally-occurring analogs may be synthesized. For example, synthesis of an exemplary nitrated fatty acids may be produced as illustrated in the general synthetic method is shown in FIG. 19.

In such embodiments, $R_1$ and $R_2$ can include any number of carbons. For example in one embodiment, a naturally occurring fatty acid having an even number of carbons (20 carbons total, in this case) may be prepared from components where $R_2$ is $CH_2CH_3$ and $R_1$ is $(CH_2)_{15}CO_2R_3$, where $R_3$ is a protecting group for the carboxylic acid functional group found in fatty acids. Similarly, a non-naturally occurring fatty acid having an odd number of carbons (19 carbons total, in this case) may be prepared from components where $R_2$ is $CH_2CH_3$ and $R_1$ is $(CH_2)_{14}CO_2R_3$, where $R_3$ is a protecting group for the carboxylic acid functional group found in fatty acids. The method illustrated in FIG. 19 can be applied to the synthesis of essentially any nitrated lipid having either an even or an odd number of carbons by incorporating different $R_1$ and $R_2$ groups. For example, each of $R_1$ and $R_2$ may be an aliphatic or substituted aliphatic carbon chain having from 1 to 20 carbons, although any greater number of carbons is also possible. Moreover, individual $R_1$ and/or $R_2$ groups may include any number of carbon-carbon double bonds, which may or may not include associated electron withdrawing groups attached to an alpha, beta, or gamma carbon of the carbon-carbon double bond. Similarly, individual $R_1$ and $R_2$ groups may include branched chains. In such embodiments, the additional carbon-carbon double bonds associated with $R_1$ and/or $R_2$ may be conjugated, unconjugated, or partially conjugated with one another or will become conjugated with a carbon-carbon double bond created as a result of the reaction. As indicated above, the reaction depicted in FIG. 19 may be carried out sequentially to create an activated fatty acid having more than one carbon-carbon double bond with associated electron withdrawing groups. In such embodiments, individual $R_1$ and $R_2$ groups for each reaction in a sequence may be from 1 to about 12 carbons, although any greater number of carbons is also possible.

Figure 19:
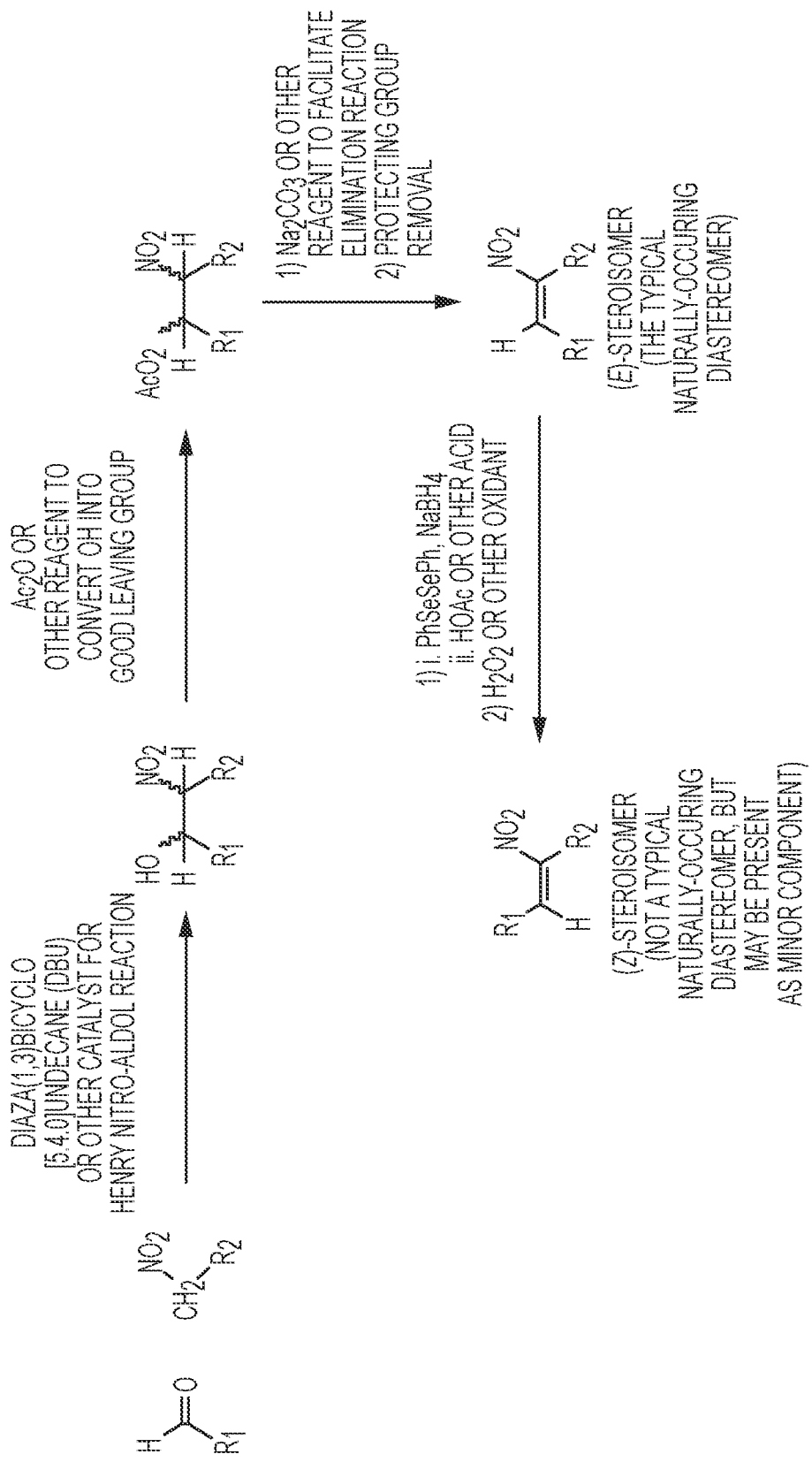
FIG. 19 shows the general synthetic method to produce nitrated fatty acids.

In some embodiments, individual $R_1$ and $R_2$ groups may contain additional functional groups other than double bonds, which may or may not be associated with a carbon-carbon double bond either existing before the reaction is carried out or following the reaction illustrated in FIG. 19. For example, individual $R_1$ and $R_2$ groups may include functional groups such as, but not limited to, alkynes, as a part of the chain, with the alkyne in the chain, alcohols, aldehyde carbonyls, ketone carbonyls, derivatives of carbonyl aldehydes and ketones, such as, oximes, hydrazones and any other carbonyl derivative known in the art, amines, amines with other groups known in the art attached to the amine, thiols, thiols with other groups known in the art attached to the thiols, any other functional group known in the art, either as the simple functional group or the functional group with another chain or group attached to it. Such functional groups may be attached to a carbon in the linear or branched chain. Without wishing to be bound by theory, the addition of additional functional groups may alter the targeting and bioavailability of the activated fatty acids of embodiments, such that specific cells or targets it within cells can be targeted.

In yet other embodiments, molecules may contain more than one carbon chain, with two or more carbon chains joined together by a non-carbon group, and in some embodiments, each of the carbon chains can be branched or linear. For example, in certain embodiments, non-carbon functional groups that can join two or more carbon chains together include, but are not limited to, those in the very common functional groups that result in the compounds listed below, wherein $R_1$ and $R_2$ are the carbon chains:

Ethers $R_1$—O—$R_2$,
Amines $R_1$—$NR_3$—$R_2$,
Esters $R_1$—C(=O)—O—$R_2$,
Amides $R_1$—C(=O)—$NR_3$—$R_2$
ThioEsters $R_1$—C(=O)—S—$R_2$
Thionoesters $R_1$—C(=S)—O—$R_2$
ThioAmides $R_1$—C(=S)—$NR_3$—$R_2$ In addition to the common non-carbon multivalent elements found in organic compounds and shown above (oxygen, nitrogen & sulfur), other functional groups known in the art, and based on any other non-carbon multivalent element may be used in embodiments of the invention. In various embodiments, any of the non-carbon chains described above could be incorporated into activated fatty acids using the general synthetic approach shown FIG. 19, in which the non-carbon chains are in $R_1$, $R_2$ or both.

Pharmaceutical Compositions

Further embodiments are directed to pharmaceutical compositions comprising activated fatty acids that are useful for treating above mentioned diseases. In certain embodiments, such pharmaceutical compositions may contain an activated fatty acid in a therapeutically effective amount and a pharmaceutically acceptable excipient, carriers and/or diluents and/or adjuvants and/or excipients, collectively referred to herein as "carrier" materials The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of activated fatty acids of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Suitable pharmaceutically acceptable base addition salts used in connection with the activated fatty acids of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

In some embodiments, a pharmaceutical composition includes a sufficient amount of activated fatty acid to provide about 5 mg to about 450 mg, about 10 mg to about 450 mg, about 25 mg to about 450 mg, about 25 mg to about 425 mg, about 25 mg to about 400 mg, about 25 mg to about 375 mg, about 25 mg to about 350 mg, about 25 mg to about 325 mg, about 25 mg to about 300 mg, about 25 mg to about 275 mg, about 25 mg to about 250 mg, about 25 mg to about 225 mg, about 25 mg to about 200 mg, about 25 mg to about 175 mg, or about 25 mg to about 150 mg of the activated fatty acid. In some embodiments, the pharmaceutical composition includes a sufficient amount of activated fatty acid to provide about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, or a range between any two of these values.

In some embodiments, a pharmaceutical composition includes a sufficient amount of activated fatty acid to provide about 50 mg to about 450 mg, about 75 mg to about 450 mg, about 100 mg to about 450 mg, about 150 mg to about 450 mg, about 175 mg to about 450 mg, about 200 mg to about 450 mg, about 225 mg to about 450 mg, about 250 mg to about 450 mg, about or about 275 mg to about 450 mg of the activated fatty acid.

In some embodiments, a pharmaceutical composition includes a sufficient amount of activated fatty acid to provide about 75 mg to about 300 mg. In some embodiments of the invention, a pharmaceutical composition includes a sufficient amount of activated fatty acid to provide from about 100 mg to about 300 mg. In some embodiments of the invention, a pharmaceutical composition includes a sufficient amount of activated fatty acid to provide from about 100 mg to about 200 mg. In some embodiments of the invention, a pharmaceutical composition includes a sufficient amount of activated fatty acid to provide from about 150 mg to about 300 mg. In some embodiments of the invention, a pharmaceutical composition includes a sufficient amount of activated fatty acid to provide about 150 mg.

In some embodiments, a pharmaceutical composition includes a sufficient amount of activated fatty acid to provide about 50 mg, about 75 mg, about 100 mg or about 150 mg of the activated fatty acid.

In some embodiments a pharmaceutical composition includes a sufficient amount of 10-nitro-9(E)-octadec-9-enoic acid to provide about 5 mg to about 450 mg, about 10 mg to about 450 mg, about 25 mg to about 450 mg, about 25 mg to about 425 mg, about 25 mg to about 400 mg, about 25 mg to about 375 mg, about 25 mg to about 350 mg, about 25 mg to about 325 mg, about 25 mg to about 300 mg, about 25 mg to about 275 mg, about 25 mg to about 250 mg, about 25 mg to about 225 mg, about 25 mg to about 200 mg, about 25 mg to about 175 mg, or about 25 mg to about 150 mg of the 10-nitro-9(E)-octadec-9-enoic acid. In some embodiments, the pharmaceutical composition includes a sufficient amount of 10-nitro-9(E)-octadec-9-enoic acid to provide about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, or a range between any two of these values.

In some embodiments, a pharmaceutical composition includes a sufficient amount of 10-nitro-9(E)-octadec-9-enoic acid to provide from about 50 mg to about 450 mg, about 75 mg to about 450 mg, about 100 mg to about 450 mg, about 150 mg to about 450 mg, about 175 mg to about 450 mg, about 200 mg to about 450 mg, about 225 mg to about 450 mg, about 250 mg to about 450 mg, about or about 275 mg to about 450 mg of 10-nitro-9(E)-octadec-9-enoic acid.

In some embodiments of the invention, a pharmaceutical composition includes a sufficient amount of 10-nitro-9(E)-octadec-9-enoic acid to provide about 75 mg to about 300 mg. In some embodiments of the invention, a pharmaceutical composition includes a sufficient amount of 10-nitro-9(E)-octadec-9-enoic acid to provide from about 100 mg to about 300 mg. In some embodiments of the invention, a pharmaceutical composition includes a sufficient amount of 10-nitro-9(E)-octadec-9-enoic acid to provide from about 100 mg to about 200 mg. In some embodiments of the invention, a pharmaceutical composition includes a sufficient amount of 10-nitro-9(E)-octadec-9-enoic acid to provide from about 150 mg to about 300 mg. In some embodiments of the invention, a pharmaceutical composition includes a sufficient amount of 10-nitro-9(E)-octadec-9-enoic acid to provide about 150 mg.

In some embodiments, a pharmaceutical composition includes a sufficient amount of 10-nitro-9(E)-octadec-9- enoic acid to provide about 50 mg, about 75 mg, about 100 mg or about 150 mg of 10-nitro-9(E)-octadec-9-enoic acid. In some embodiments, a pharmaceutical composition includes a sufficient amount of 10-nitro-9(E)-octadec-9-enoic acid to provide 150 mg of the activated 10-nitro-9(E)-octadec-9-enoic acid.

Pharmaceutical formulations comprising the compounds of the above invention and a suitable carrier can be in various forms including, but not limited to, solids, solutions, powders, fluid emulsions, fluid suspensions, semi-solids, and dry powders including an effective amount of an activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Oilman's, The Pharmaceutical Basis of Therapeutics*, 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethyleneglycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include activated fatty acid prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of an activated fatty acid in solid dosage form may vary. For example, in one embodiment, a liquid or gelatin formulation of the activated fatty acid may be prepared by combining the activated fatty acid with one or more fatty acid diluent, such as those described above, and adding a thickening agent to the liquid mixture to form a gelatin. The gelatin may then be encapsulated in unit dosage form to form a capsule. In another exemplary embodiment, an oily preparation of an activated fatty acid prepared as described above may be lyophilized to for a solid that may be mixed with one or more pharmaceutically acceptable excipient, carrier or diluent to form a tablet, and in yet another embodiment, the activated fatty acid of an oily preparation may be crystallized to from a solid which may be combined with a pharmaceutically acceptable excipient, carrier or diluent to form a tablet.

Further embodiments which may be useful for oral administration of activated fatty acids include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, activated fatty acids of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the activated fatty acids has between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to poly-oxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-7 19 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—CH2-CH2-. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include activated fatty acids administered in combination with other active such as, for example, adjuvants, protease inhibitors, or other compatible drugs or compounds where such combination is seen to be desirable or advantageous in achieving the desired effects of the methods described herein.

This invention and embodiments illustrating the method and materials used may be further understood by reference to the following non-limiting examples.

EXAMPLES

Example 1: Evaluation of
10-nitro-9(E)-octadec-9-enoic acid in a
deoxycorticosterone acetate (DOCA)/salt-induced
model of FSGS 10-nitro-9(E)-octadec-9-enoic acid, given orally after onset of renal injury, was evaluated for efficacy in a model for Focal Segmental Glomerular Sclerosis (FSGS) in humans. This was the first demonstration of the activity of oral 10-nitro-9(E)-octadec-9-enoic acid in a model of CKI. Mice were uni-nephrectomized and, after two weeks, implanted subcutaneously with DOCA (50 mg, 21-day release) or placebo sustained release pellets, with pellet replacement 3 weeks later. All groups, except the sham control group, also received 1% NaCl in tap water. 10-nitro-9(E)-octadec-9-enoic acid (daily oral gavage, 2.5 or 12.5 mg/kg) or enalapril (20 mg/kg/day in drinking water) treatments began 2 weeks after the first DOCA implantation and continued for 4 weeks. Enalapril was included for comparison because it is used as standard of care for FSGS and this is a positive control for the model.

Mice undergoing the DOCA/salt treatment without drug administration developed renal disease of relatively modest severity as expected. 10-nitro-9(E)-octadec-9-enoic acid at 2.5 mg/kg/day (but not 12.5 mg/kg) was highly effective as a renal protector 10-nitro-9(E)-octadec-9-enoic acid was undertaken in a deoxycorticosterone acetate (DOCA)/salt-induced model of early CKI in which groups of uninephrectomized mice were treated for 14 weeks with 10-nitro-9(E)-octadec-9-enoic acid (two dose levels) or enalapril. 10-nitro-9(E)-octadec-9-enoic acid at lower doses demonstrated renoprotective effects including: 1) reduced urinary albumin, nephrin and monocyte chemoattractant protein-1 (MCP-1) excretion, 2) inhibition of gene expression of pro-inflammatory cytokines (MCP-1 and osteopontin), extracellular matrix (collagen III and fibronectin) and pro-fibrotic factor, plasminogen activator inhibitor-1 (PAI-1), 3) improved renal pathological lesions as evidenced by a marked reduction in renal fibrosis, 4) reduced cardiac and renal hypertrophy, and 5) positive impact on cholesterol metabolism. The beneficial effects of 10-nitro-9(E)-octadec-9-enoic acid were significantly differentiated from enalapril, the established standard, in this treatment model of early kidney fibrosis and injury. 10-nitro-9(E)-octadec-9-enoic acid or its homolog has also been shown reduce angiotensin activity through adduction of the angiotensin receptor AT1R. Thus, 10-nitro-9(E)-octadec-9-enoic acid may have beneficial effect on the intraglomerular pressure and hemodynamics as well as on the long-term pathological effects due to prolonged systemic hypertension. The study and results are detailed below.

The study was undertaken to examine the potential therapeutic benefit of 10-nitro-9(E)-octadec-9-enoic acid in the DOCA salt model. This model exhibits hypertension and chronic renal injury that mimics human Focal Segmental Glomerular Sclerosis (FSGS).

Induction of model: Male mice (129/sv strain) were purchased from Taconic Labs. The animals were uninephrectomized (Unx) at 6 weeks of age by the vendor and shipped one week after surgery. At 2 weeks post Unx, a DOCA or placebo pellet (21-day release pellets, 50 mg/pellet, Innovative Research of America, Sarasota, Fla.) was implanted s.c. All mice were then placed on a semisynthetic diet which contained a moderate fat content and a low phytoestrogen/anti-oxidant level, which approximates a normal human diet (4). A second DOCA or placebo pellet was implanted three weeks later.

Figure 1:
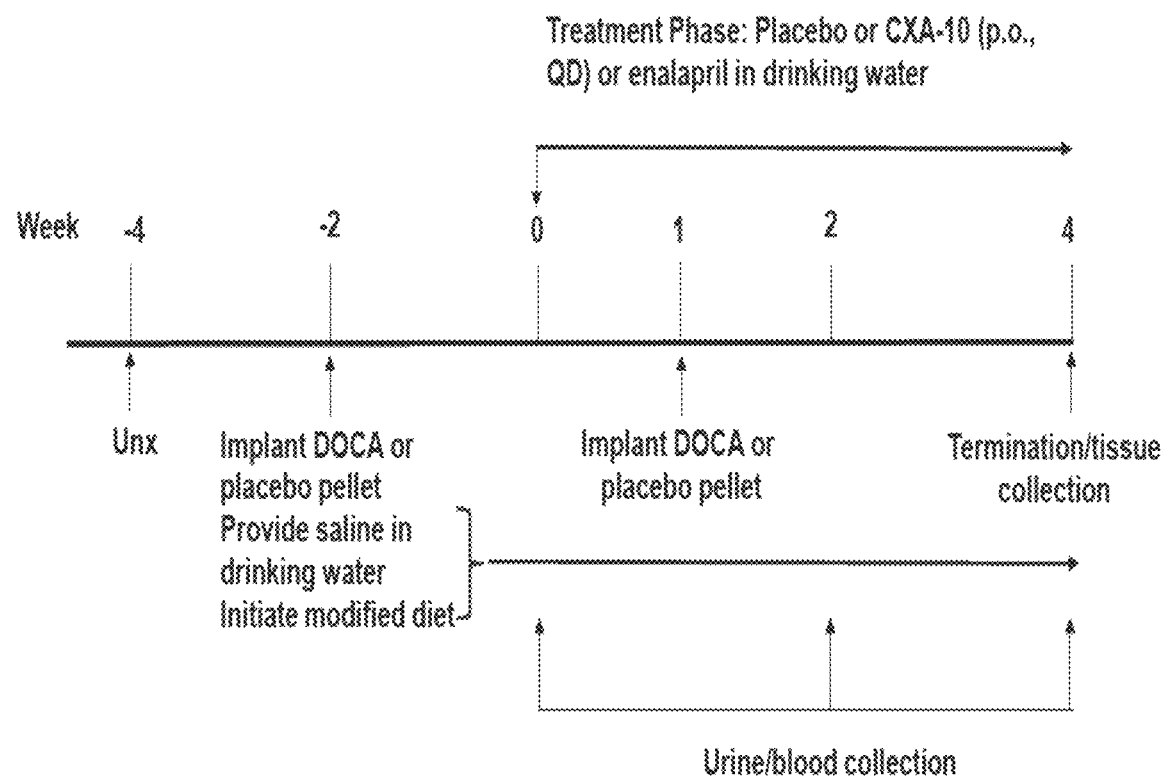
FIG. 1 describes the study design and timeline of the DOCA salt mouse model.

Treatment: Mice were treated with placebo, 10-nitro-9 (E)-octadec-9-enoic acid at a dose of 2.5 and 12.5 mg/kg, or enalapril (standard of care) for 4 weeks by oral gavage starting 2 weeks after the first DOCA implantation. One percent NaCl in tap water was given to each group except the sham control group. Body weight was measured weekly, and doses were readjusted based on the current body weight. Urine and blood samples were collected prior to treatment and at week 2 and 4 of treatment. Mice were terminated at week 4. Data is presented as the mean+SEM for the number of animals listed in each group. The study design and timeline are shown in FIG. 1.

Treatment groups include:

| Group Name | Also referred to as | # of mice | treatment |
|---|---|---|---|
| Control | Ctrl<br>Normal<br>Sham, | 10 | sham + placebo pellet |
| DOCA | Vehicle<br>Untreated<br>Placebo (Figure 12) | 10 | Unx + DOCA +<br>moderate fat/semi-<br>synthetic diet (MFD) |
| 10-nitro-9(E)-<br>octadec-9-<br>enoic acid 2.5<br>(low dose) | CXA-10 2.5 mpk<br>CXA-10 2.5<br>CXA 2.5<br>DOCA + 2.5<br>mg/kg CXA 10<br>DOCA + 2.5 | 8 | Unx + DOCA +<br>MFD + 10-nitro-<br>9(E)-octadec-<br>9-enoic acid at 2.5<br>mg/kg, p.o, QD |
| 10-nitro-9(E)-<br>octadec-9-<br>enoic acid 12.5<br>(high dose) | CXA-10 12.5 mpk<br>CXA-10 12.5<br>CXA 12.5<br>DOCA + 12.5<br>mg/kg CXA 10<br>DOCA + 12.5 | 8 | Unx + DOCA +<br>MFD + 10-nitro-<br>9(E)-octadec-9-<br>enoic acid at 12.5<br>mg/kg, p.o, QD |
| Enalapril | Enal<br>DOCA + Enal<br>DOCA + 20 mg/kg<br>Enalapril | 9 | Unx + DOCA +<br>MFD + enalapril<br>at 20 mg/kg/d<br>in drinking water |

Serum and urine analyses: Blood samples were collected from the retro-orbital sinus and samples were separated to serum. Serum and urine creatinine (enzymatic assay), blood urea nitrogen (BUN), and serum cholesterol were measured using a Cobas 400 plus bioanalyzer (Roche Diagnostics, IN). Urine samples were collected for 24 h using metabolic cages. Urine albumin was measured by immunoassay Albuwell M (Exocell Inc., Philadelphia, Pa.). Immuno-ELISA according to manufacturer's instructions was used to measure urine nephrin (Exocell Inc., Philadelphia, Pa.) and MCP-1 (Thermal Scientific, Waltham, Mass.). Kim-1 was measured using the E-90KIM Mouse ELISA Kit (Immunology Consultants Laboratory, Portland, Oreg.). Statistical analyses for serum and urine data was performed using a two-tailed Student's t-test.

Glomerular Filtration Rate: Glomerular filtration rate (GFR) was performed at the 4 week timepoint using a FIT-GFR test kit for inulin according to manufacturer's instructions (BioPal, Worcester, Mass.). A 5 mg/kg bolus intraperitoneal injection of inulin was given, followed by serial saphenous bleeds at 30, 60, and 90 minutes. Serum was isolated and quantified by an inulin ELISA. Inulin serum clearance was determined by nonlinear regression using a one phase exponential decay formula according to manufacturer's instructions.

Histological Assessment: Formalin fixed, paraffin embedded kidneys were sectioned at 3 microns and stained with hematoxylin and eosin (H&E), periodic acid-Schiff (PAS) and Masson's Trichrome for histological analysis. Slides were blindly evaluated by an experienced pathology investigator. Glomerular and tubular pathology, interstitial inflammation and interstitial fibrosis were semi-quantitatively scored on a scale of 0-4 as follows: 0=normal; 1=mild; 2=moderate; 3=marked; 4=severe.

Immunohistochemistry: Podocyte counting was assessed using anti-WT1 (Wilms Tumor 1) clone 6F-H2 at 1:100 dilution (Dako). Immunohistochemistry was performed on a Leica Bond MAX automated immunostainer (Leica Microsystems Inc. Bannockburn, Ill.). 0.05% Tween20/Tris buffered saline (DAKO) washes were performed between all steps. Tissue sections were dewaxed, treated with Proteinase K enzyme, then peroxidase. Tissues were then treated with rodent block (BioGenex, Fremont, Calif.), incubated with anti-WT-1 primary antibody which was then detected using mouse anti-mouse streptavidin-HRP. Chromagen visualization was performed using 3,3'-diaminobenzidine tetrahydrochloride (DAB) for 5 minutes, followed by hematoxylin counterstain and dehydration through increasing ethanol-water gradient to xylene, and mounted in Permount (Fisher Scientific, Pittsburgh, Pa.). Whole kidney sections were imaged using Aperio ScanScope (Aperio Technologies, Vista, Calif.). 50 glomeruli per kidney section were quantitated for the number of WT-1 positive (brown) and WT-1 negative cells (blue). Software analysis was done using custom algorithm on Spectrum Version 11.0.0.725 (Aperio Technologies). Immunohistochemistry was also performed to examine CD31 (Abcam, Cambridge, Mass.), a marker of endothelial integrity. Statistical analysis of the histological data was performed using the non-parametric Kruskal-Wallis test followed by Dunn's Multiple Comparison Test.

RT-PCR Analysis of Gene Expression: A slice of kidney from each mouse was placed in Trizol solution (Invitrogen) immediately after harvesting and stored at −80° C. until analysis. Tissues were homogenized using a bead mill in 0.5 ml of Trizol solution and total RNA was extracted with chloroform (Sigma) and purified using standard RNeasy mini kit (Qiagen), with on column DNase 1 (Qiagen) digestion to avoid non-specific fluorescence emission derived from the recognition of contaminating genomic DNA by the probe, according to manufacturer's recommendation. RNA samples were eluted in 30 µl of nuclease-free water and quantified using a Nanodrop. cDNA was generated from 2 µg of RNA by using Clontech Sprint PowerScript reagents according to manufacturer's protocol. Fluorogenic probes specific for genes assayed in the report were purchased from Applied Biosystems. PCR amplification and analysis of PCR reaction were performed and monitored using an ABI Prism 7900HT Sequence Detection System (TaqMan, Perkin-Elmer Applied Biosystem). Data analysis was carried out by using the Sequence Detection Systems v2.3 program (Applied Biosystems). For each cDNA sample the Ct value of each target sequence was normalized to reference gene (Ribosomal RNA-18S), and shown as fold changes to control group. Statistical analyses for gene expression data was performed using a two-tailed Student's t-test.

Figure 2:
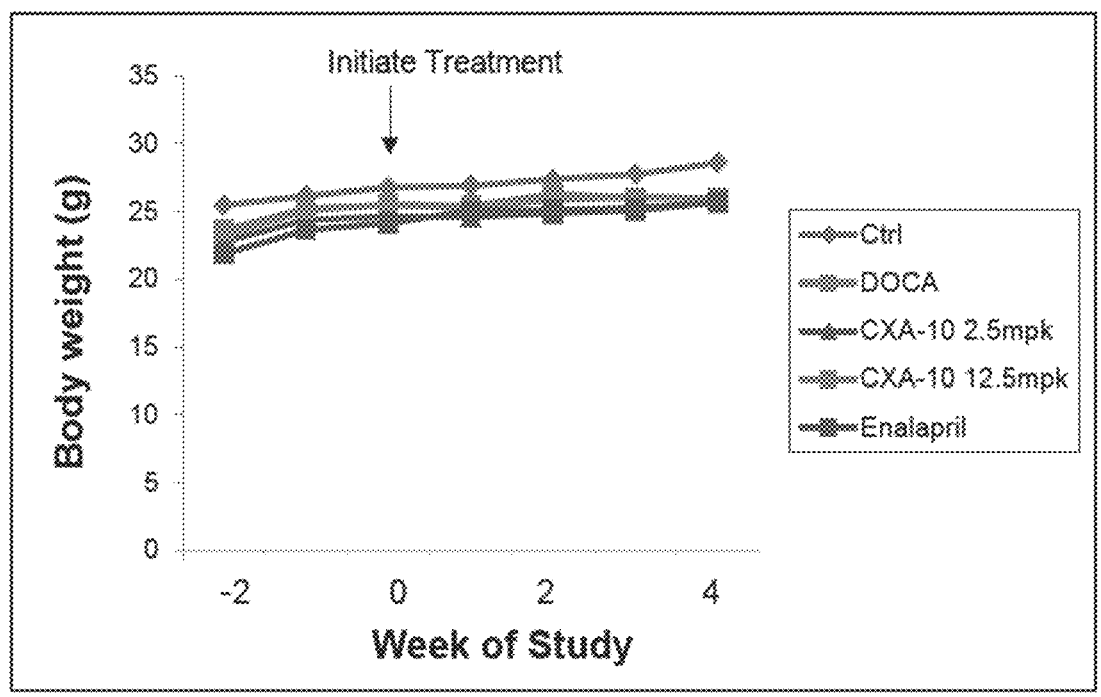
FIG. 2 shows the change in body weight over the time course obtained from the DOCA salt study. Control (Ctrl) is represented as a grey diamond, DOCA as a light grey square, CXA-10 (10-nitro-9(E)-octadec-9-enoic acid) 2.5 mpk as a medium grey triangle, CXA-10 (10-nitro-9(E)-octadec-9-enoic acid) 12.5 mpk a light grey square and Enalapril as a dark grey square.
Figure 3:
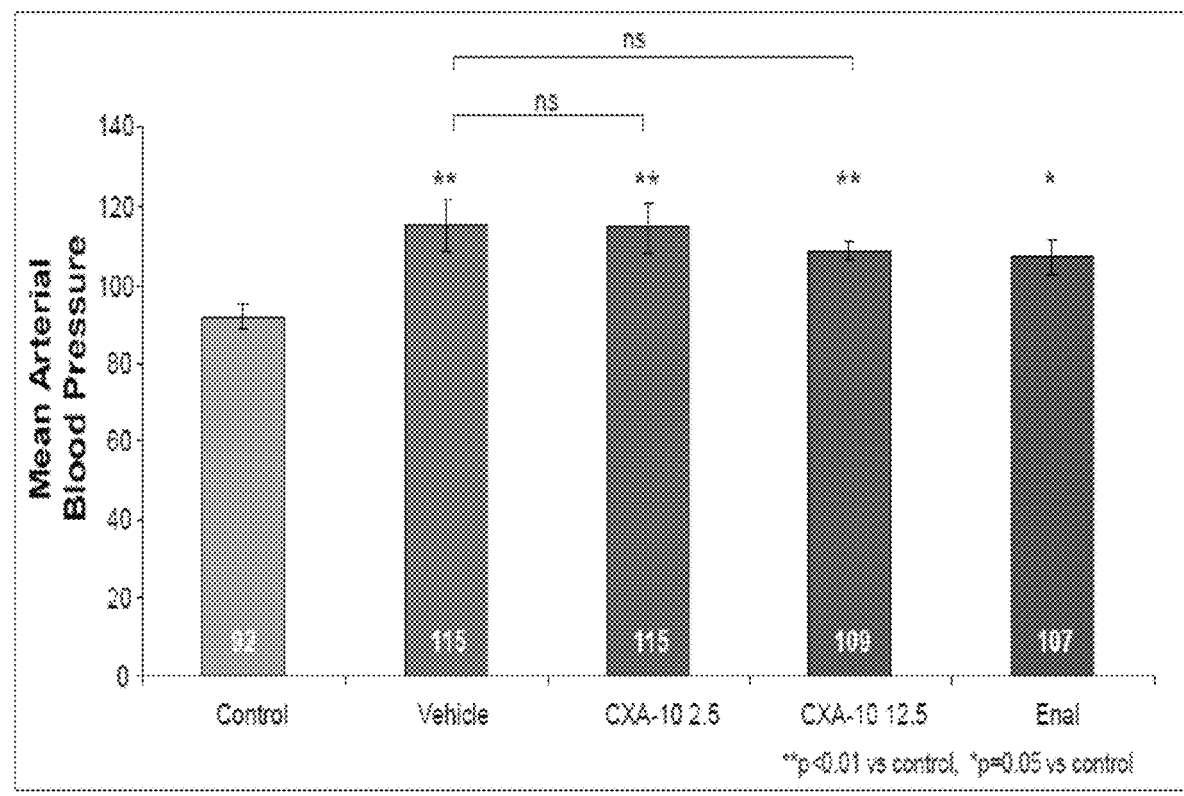
FIG. 3 shows the mean arterial blood pressure obtained from the DOCA salt study for each of the five cohorts: Control, vehicle, CXA-10 2.5 (10-nitro-9(E)-octadec-9-enoic acid, 2.5 mg), CXA-10 12.5 (10-nitro-9(E)-octadec-9-enoic acid, 12.5 mg), and Enal (Enalapril).
Figure 4:
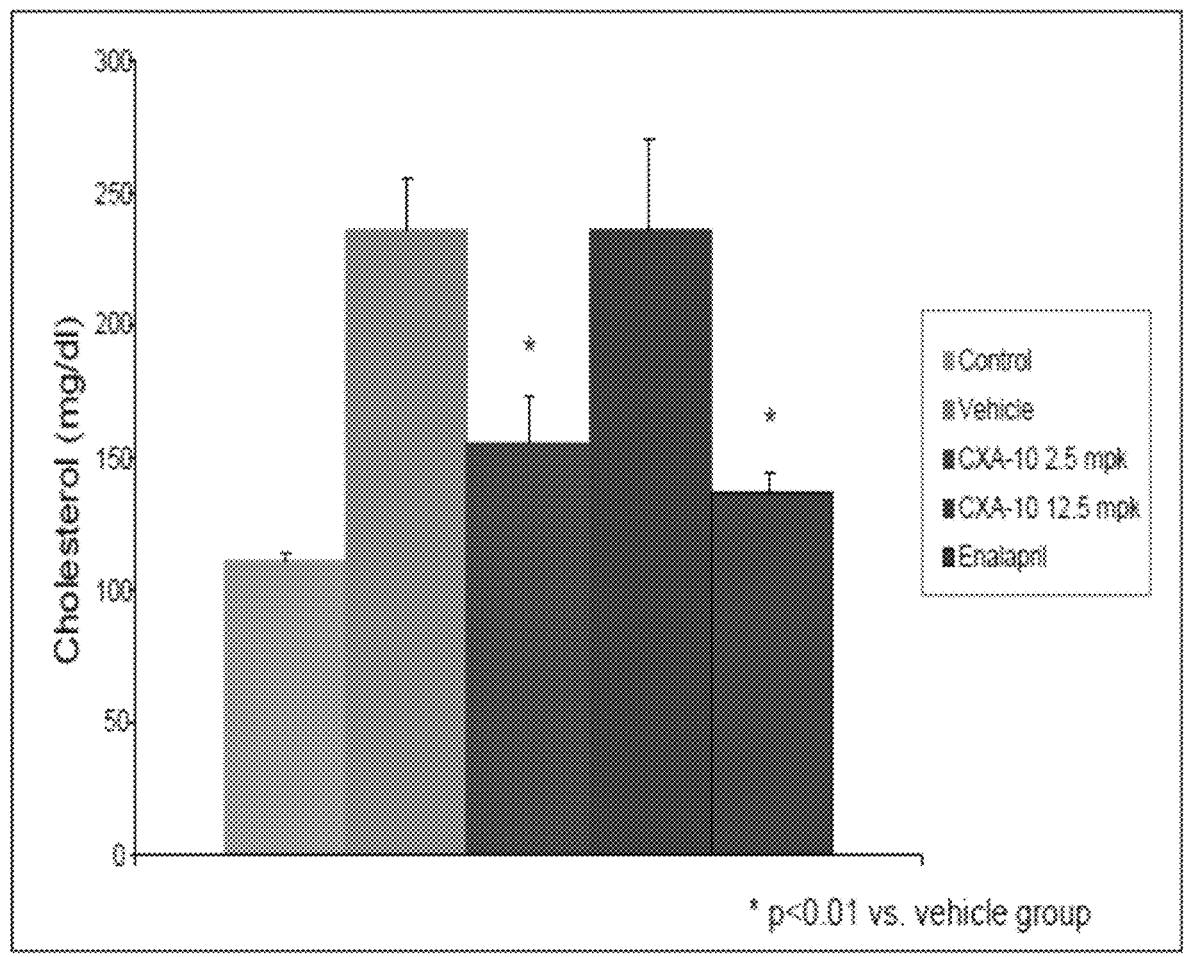
FIG. 4 shows the effect of treatment on plasma cholesterol levels obtained from the DOCA salt study. From left to right, the first bar represents the control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

Body weight was slightly decreased with Unx, but body weight gains were unaffected with 10-nitro-9(E)-octadec-9-enoic acid treatment or enalapril (FIG. 2). Blood pressure was modestly elevated in this model, but none of the treatments, including enalapril, had a significant effect on blood pressure (FIG. 3). 10-nitro-9(E)-octadec-9-enoic acid has been reported to have a positive impact on abnormal lipid metabolism. Nephrotic syndromes, including FSGS, are associated with hypercholesterolemia. In this study, plasma cholesterol was significantly elevated in animals dosed with vehicle, and was reduced with either low dose 10-nitro-9(E)-octadec-9-enoic acid or enalapril (FIG. 4).

Figure 5:
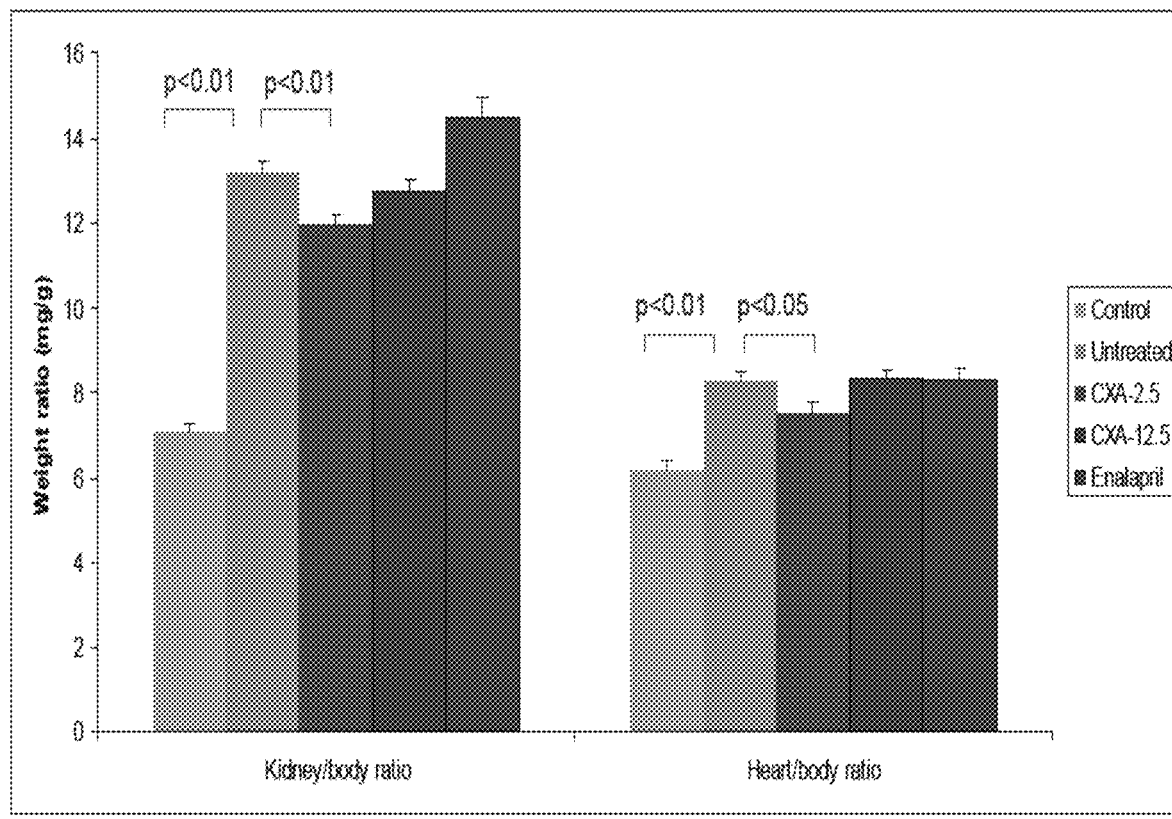
FIG. 5 shows the effect of treatment on kidney/body weight and heart/body weight ratios obtained from the DOCA salt study. Within both groups (kidney/body ratio and heart/body ratio), reading from left to right, the first bar represents the control, the second bar is untreated, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

Kidney/body weight and heart/body ratios were determined (FIG. 5). Both ratios were increased in untreated mice and reduced with low dose 10-nitro-9(E)-octadec-9-enoic acid, indicating an overall improvement in structure of the kidney and heart. However, enalapril had no effect.

Figure 7:
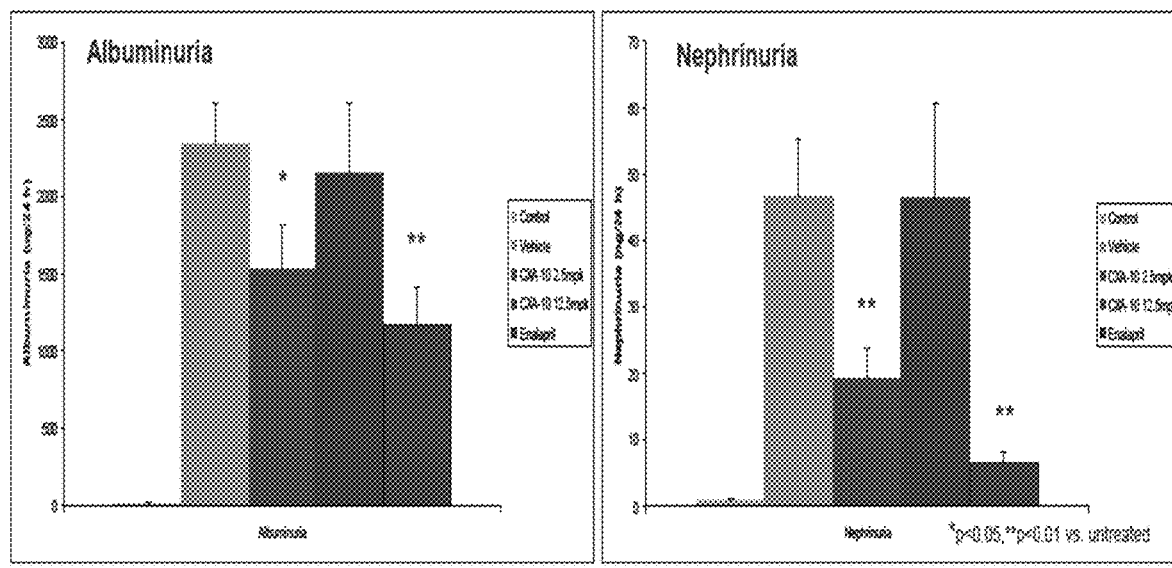
FIG. 7 shows the effect of treatment on urinary albumin and nephrin excretion obtained from the DOCA salt study. Within both graphs (Albuminuria left and Nephrinuria right), reading from left to right, the first bar represents the control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

The DOCA/salt treatment led to increased mean arterial pressure, and kidney and heart hypertrophy. The hypertension in this model is not angiotensin mediated, so neither enalapril nor 10-nitro-9(E)-octadec-9-enoic acid were expected to reduce blood pressure. Hypertrophy of both organs was partially reduced in only the lower dose 10-nitro-9(E)-octadec-9-enoic acid treatment group. The DOCA/salt treated groups showed elevated plasma cholesterol, also a hallmark of FSGS and other nephrotic syndromes, which was decreased with either the lower dose 10-nitro-9(E)-octadec-9-enoic acid or the enalapril treatment. Lower dose 10-nitro-9(E)-octadec-9-enoic acid and enalapril treatments both markedly reduced albumin excretion and urinary nephrin levels (FIG. 7).

Figure 6:
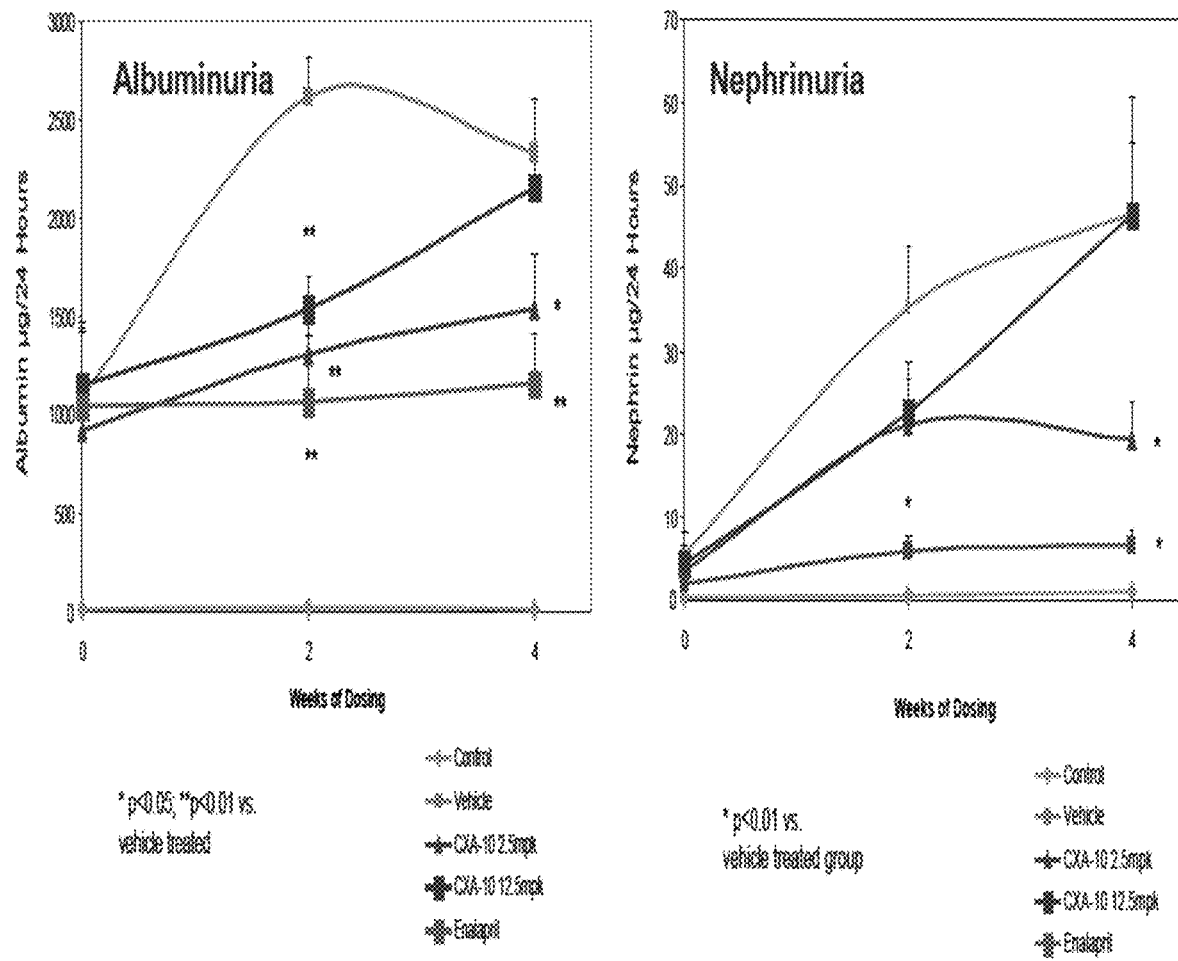
FIG. 6 shows the time course for the effect of treatment on albuminuria and nephrin excretion obtained from the DOCA salt study. Within both graphs (Albuminuria left and Nephrinuria right), control is represented as a grey diamond, vehicle as a medium grey small square, CXA-10 2.5 mpk (10-nitro-9(E)-octadec-9-enoic acid, 2.5 mg) as a medium grey triangle, CXA-10 12.5 mpk (10-nitro-9(E)-octadec-9-enoic acid, 12.5 mg) as a black rectangle and Enalapril as a dark grey rectangle. In the left graph, $*p<0.05$ and $**$ $p<0.01$. In the right graph, $*p<0.01$
Figure 8:
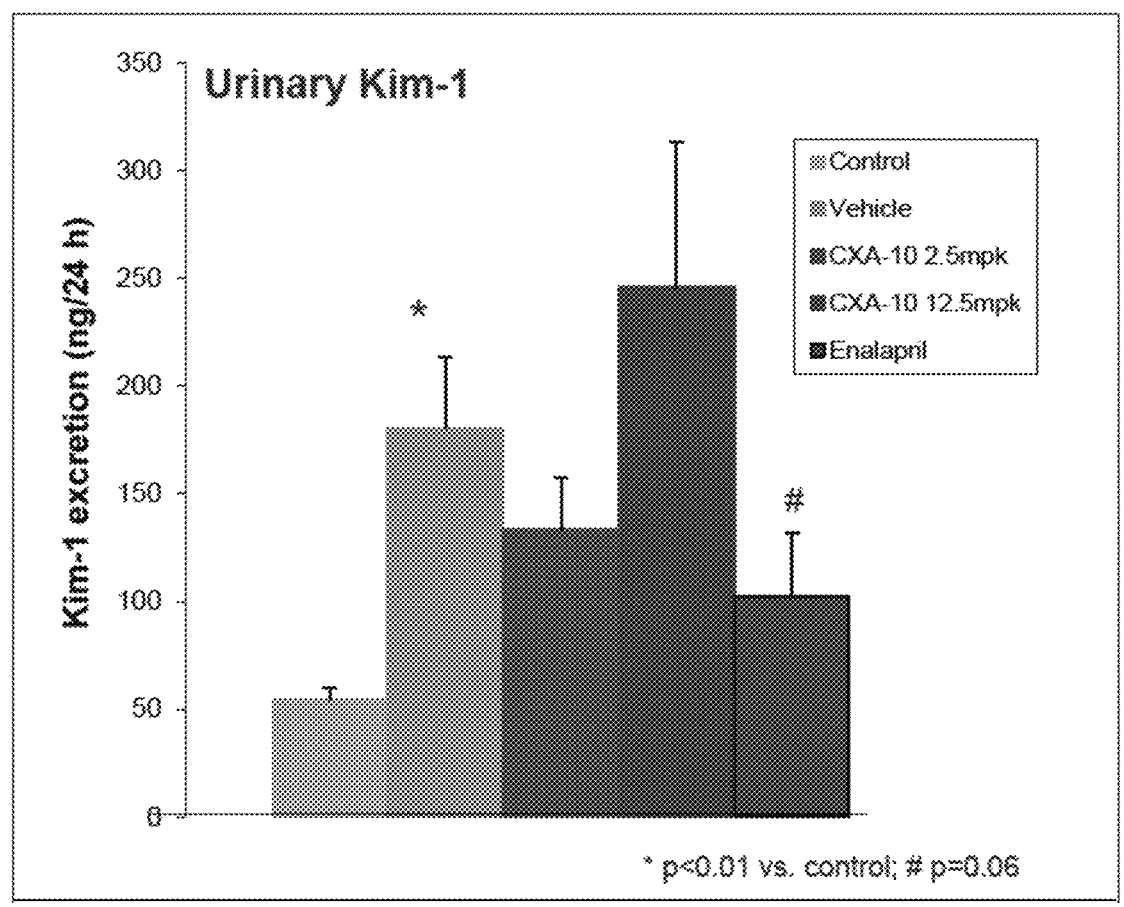
FIG. 8 shows the effect of treatment on Kim-1 in urine obtained from the DOCA salt study. Reading from left to right, the first bar represents the control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

Treatment with 10-nitro-9(E)-octadec-9-enoic acid at 2.5 mg/kg resulted in a marked reduction in albuminuria, which was reduced by 49% at week 2 and 34% at week 4 post-dosing (FIG. 6). The reduction with 10-nitro-9(E)-octadec-9-enoic acid at the low dose was comparable to enalapril. High dose 10-nitro-9(E)-octadec-9-enoic acid had an effect initially but it was not sustained. In parallel, urinary nephrin excretion was elevated and treatment effects were similar to changes in albuminuria. A comparison of the data at the 4 week timepoint indicated that the changes in albuminuria and nephrinuria showed a similar pattern with treatment (FIG. 7). These results indicate that the low dose 10-nitro-9(E)-octadec-9-enoic acid reduced albuminuria, likely through protecting podocytes from damage. Kim-1, a marker of tubular injury which associates with regions of inflammation and fibrosis, was also quantitated in urine (FIG. 8). It was found to be significantly increased in the DOCA model relative to the control group, and trended to be decreased with enalapril relative to the DOCA group.

Figure 9:
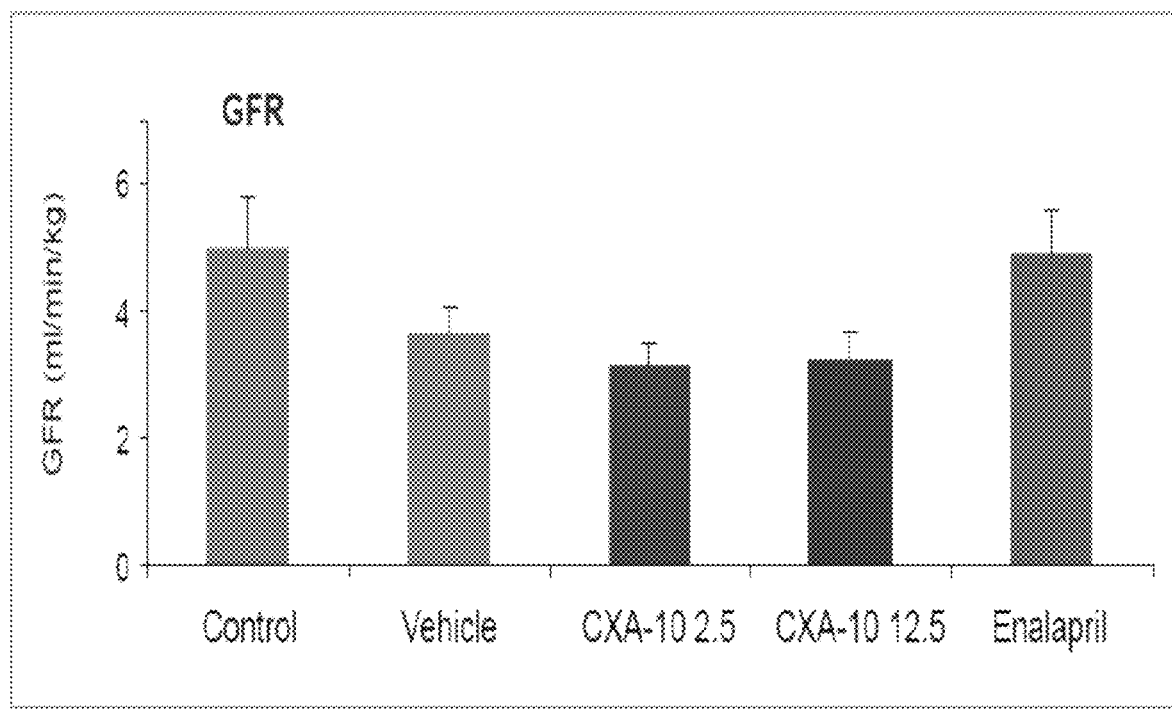
FIG. 9 shows the effect of treatment on GFR obtained from the DOCA salt study.
Figure 10:
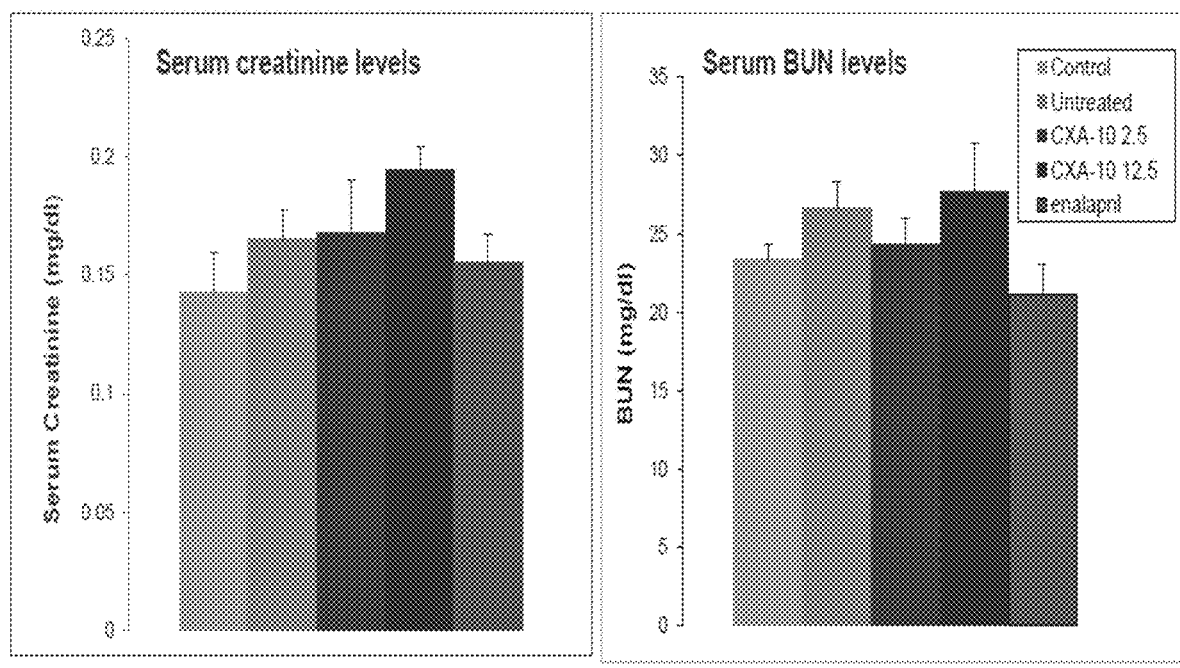
FIG. 10 shows the effect of treatment on serum creatinine and BUN levels obtained from the DOCA salt study after 4 weeks of treatment. Within both graphs (Serum creatinine levels left and Serum BUN levels right), reading from left to right, the first bar represents the control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

GFR was assessed by using the inulin method. It showed a modest decline in vehicle-treated mice, without reaching statistical significance (FIG. 9). None of the treatment groups were statistically significant from the vehicle-treated group, but there was a trend toward an increase in mice treated with enalapril. Serum creatinine and BUN (FIG. 10) levels were in the normal range for all groups. This is consistent with the modest disease severity in this model.

The histological evaluation (FIG. 11) indicated that ~15% of glomeruli displayed mild to severe glomerular damage including mesangial expansion and sclerosis in vehicle treated group. Tubular damage was also evident to some degree, showing patchy lesions of dilated tubules, casts, and tubulointerstitial expansion and fibrosis. After 4 weeks of treatment, tubulointerstitial lesions were improved in mice dosed with low dose 10-nitro-9(E)-octadec-9-enoic acid but only slightly with the high dose. The effect of enalapril was similar to the low dose 10-nitro-9(E)-octadec-9-enoic acid. Glomerulosclerosis was assessed and scored individually with score 1-4 (FIG. 12). Average scores and percent of glomerular damage (sclerosis) were significantly reduced with both doses of 10-nitro-9(E)-octadec-9-enoic acid, but this was not significantly reduced with enalapril.

Figure 13:
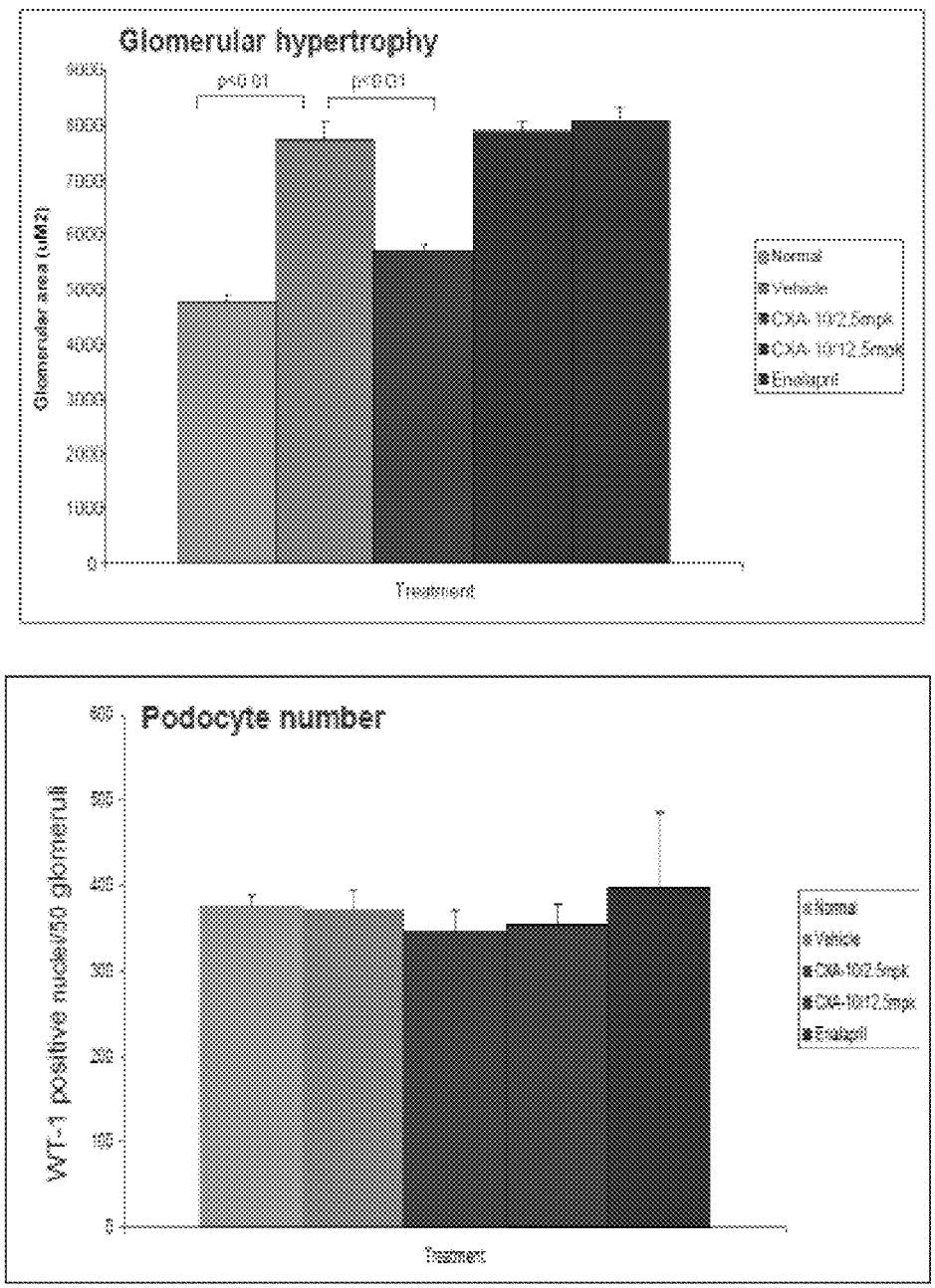
FIG. 13 shows the quantitation of glomerular hypertrophy and podocyte number following treatment in the DOCA salt study. Within both graphs (glomerular hypertrophy top and podocyte number bottom), reading from left to right, the first bar represents normal (also known as control), the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

Glomerular hypertrophy was evaluated by measuring glomerular area and expressed as a mean value of 50 glomeruli per kidney. Glomerular hypertrophy is an important marker for diabetic and hypertensive-mediated chronic kidney disease. As expected, the vehicle treated group showed hypertrophy; this was reduced with low dose 10-nitro-9(E)-octadec-9-enoic acid, while high dose and enalapril did not have an effect (FIG. 13, top panel). Podocyte number was quantified by WT-1 staining and was found to be unchanged in all treatment groups (FIG. 13, bottom panel). This finding is consistent with unchanged gene expression profile for podocyte markers (Table 2), and seems reasonable given that the disease was relatively modest. However, in an adriamycin-induced nephropathy model where 10-nitro-9(E)-octadec-9-enoic acid was continually infused at disease onset, and in the db/db model where 10-nitro-9(E)-octadec-9-enoic acid was also given by infusion, there was an increase in podocyte number with treatment.

Table 2 Shows the Effect of Treatment on the Expression of Podocyte Genes.

|   | Nephrin | Podocin |
|---|---|---|
| Control | 1.003 ± 0.035 | 1.033 ± 0.117 |
| Vehicle | 1.449 ± 0.2 | 1.234 ± 0.087 |
| CXA-10 2.5 mpk | 1.264 ± 0.0789 | 1.077 ± 0.123 |
| CXA-10 12.5 mpk | 1.313 ± 0.15 | 1.117 ± 0.084 |
| Enalapril | 1.091 ± 0.14 | 0.9991 ± 0.095 |

Endothelial injury was assessed in renal tissue by performing immunohistochemistry staining to detect CD31+ cells (FIG. 14), which is a marker for endothelial integrity. The results indicate that CD31+ cells were unchanged in all groups. The lack of change in the vehicle treated group might reflect the modest disease severity in this model.

Figure 15:
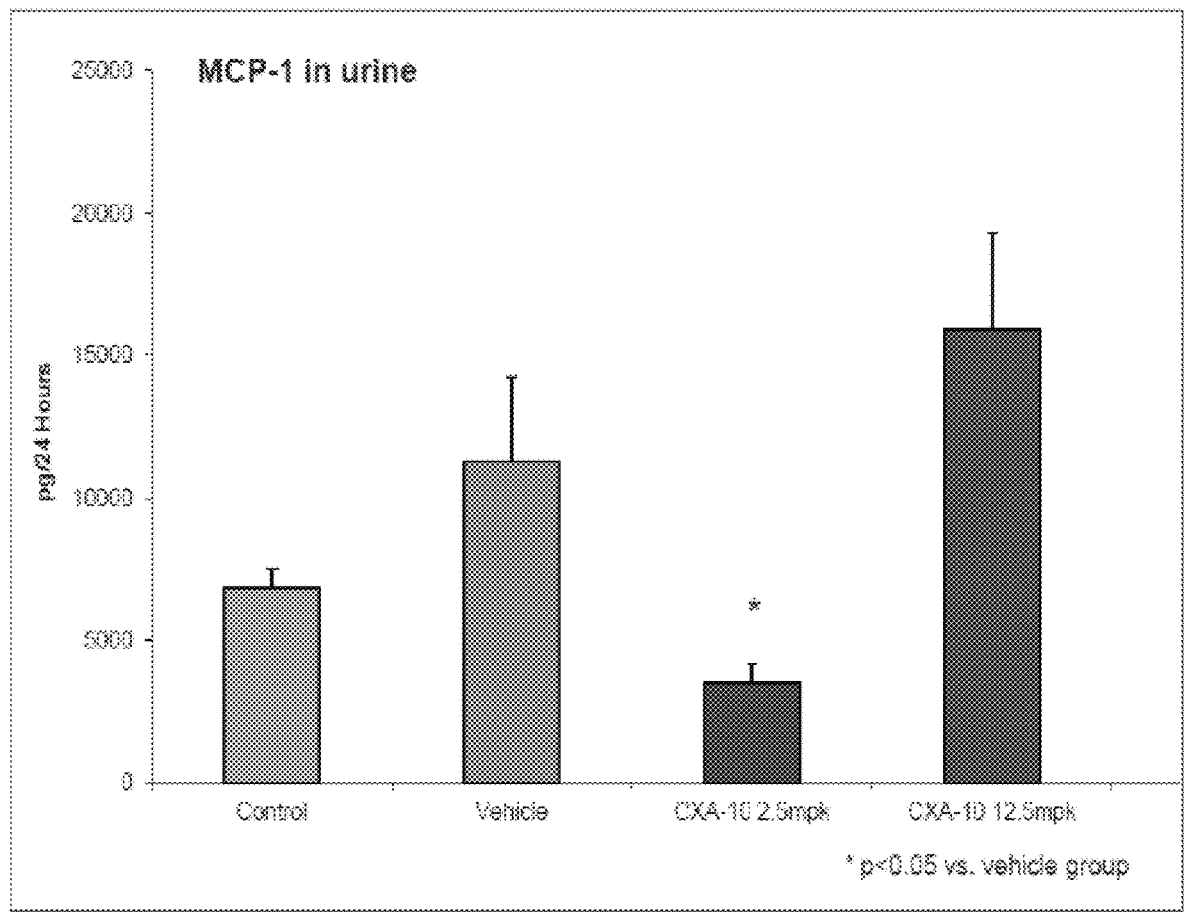
FIG. 15 shows the effect of treatment on urinary MCP-1 excretion obtained from the DOCA salt study. Reading from left to right the first bar represents control, the second bar is vehicle, the third bar is CXA-10 2.5 mpk (10-nitro-9(E)-octadec-9-enoic acid, 2.5 mg), and the forth bar is CXA-10 12.5 mpk (10-nitro-9(E)-octadec-9-enoic acid, 12.5 mg).

MCP-1 is a key chemokine that regulate migration and infiltration of monocytes/macrophages. Both MCP-1 and its receptor have been demonstrated to be induced in chronic kidney diseases and it is also considered as a potential biomarker. Urinary MCP-1 excretion was elevated in the vehicle treated group, which was significantly reduced in mice treated with low dose 10-nitro-9(E)-octadec-9-enoic acid for 4 weeks, while high dose 10-nitro-9(E)-octadec-9-enoic acid had no effect (FIG. 15). The finding supports the published anti-inflammatory property of 10-nitro-9(E)-octadec-9-enoic acid.

Figure 16:
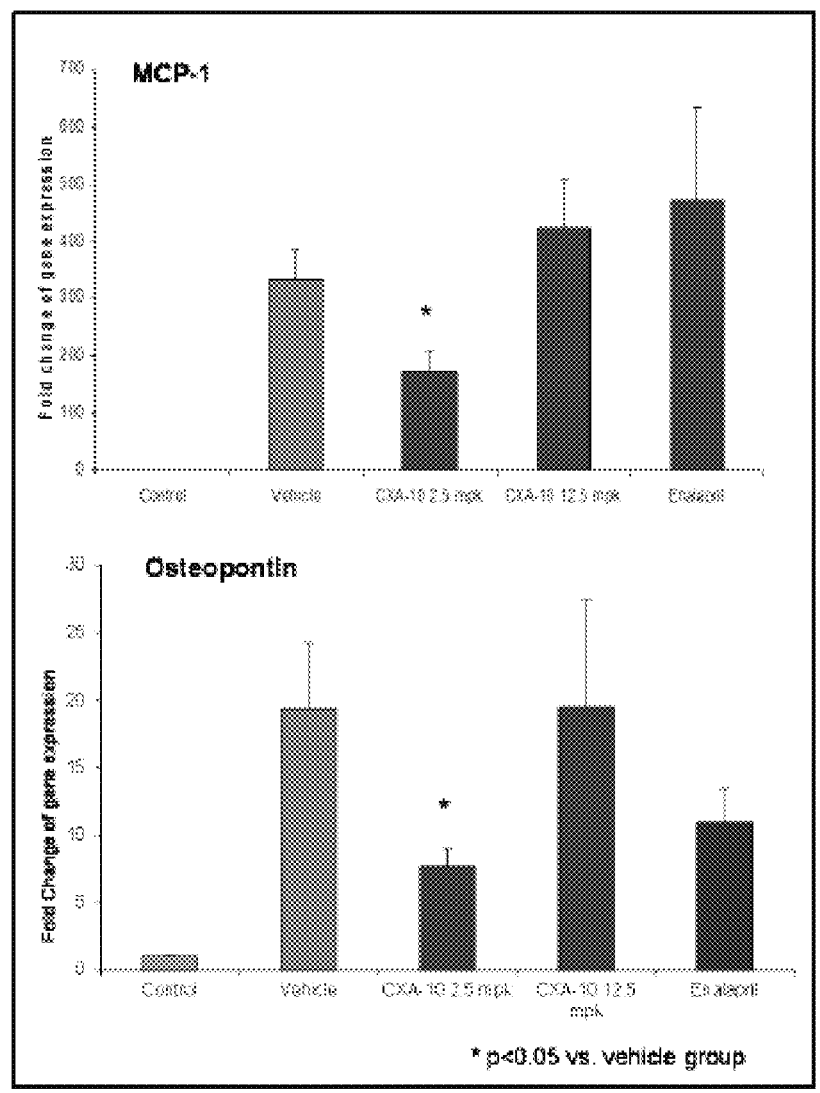
FIG. 16 shows the effect of treatment on MCP-1 and osteopontin gene expression obtained from the DOCA salt study. Reading from left to right, the first bar represents control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.
Figure 17:
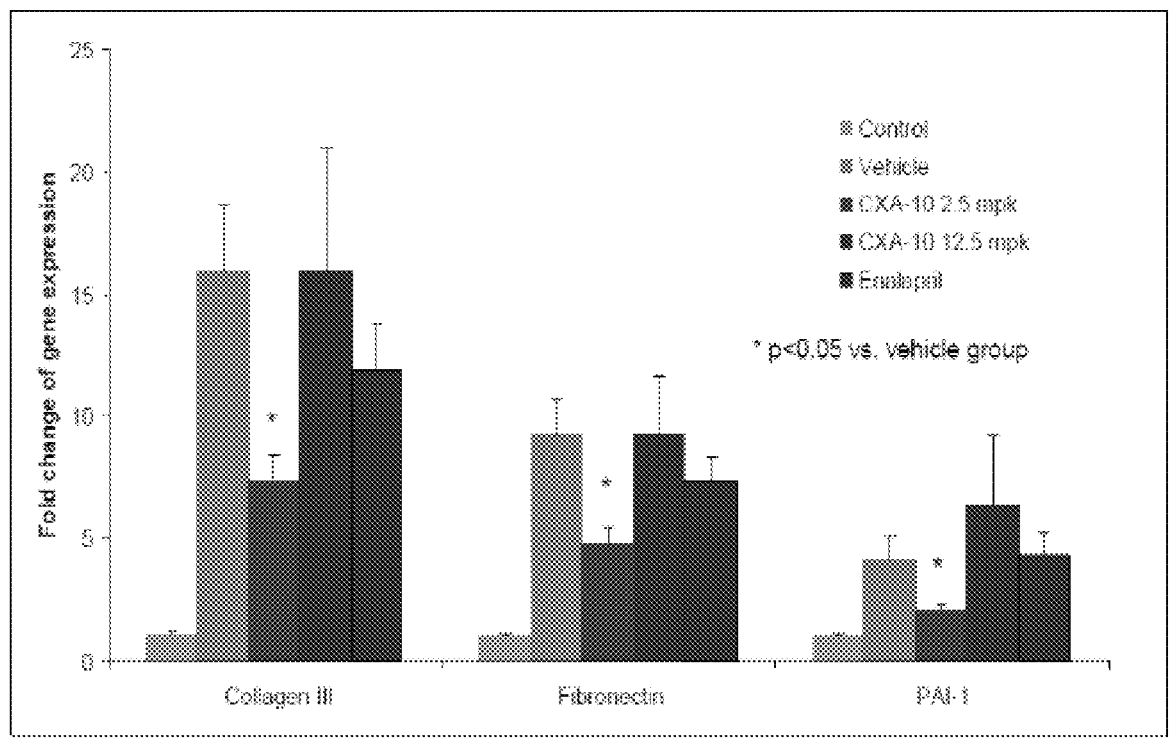
FIG. 17 shows the effect of treatment on fibrotic and inflammatory gene expression obtained from the DOCA salt study. Within all three groups (Collegon III, Fibrotectin, PAI-1), reading from left to right, the first bar represents control, the second bar is vehicle, the third bar is CXA-10 2.5 mpk (10-nitro-9(E)-octadec-9-enoic acid, 2.5 mg), the forth bar is CXA-10 12.5 mpk (10-nitro-9(E)-octadec-9-enoic acid, 12.5 mg) and the final bar is Enalapril.

Gene expression of pro-inflammatory (MCP-1 and osteopontin), extracellular matrix (collagen III and fibronectin), and PAI-1 (inflammatory and pro-fibrotic), was evaluated at mRNA level using qRT-PCR. The results (FIGS. 16 and 17) indicate that gene expression was significantly up-regulated in vehicle treated mice. Treatment with low dose 10-nitro-9(E)-octadec-9-enoic acid inhibited these genes, but neither the high dose 10-nitro-9(E)-octadec-9-enoic acid nor enalapril had an effect on any of those genes. The data reveals that, in addition to supporting its anti-inflammatory effect, 10-nitro-9(E)-octadec-9-enoic acid attenuates fibrogenesis. The lower dose 10-nitro-9(E)-octadec-9-enoic acid treatment group showed a decrease in the amount of the proinflammatory cytokine MCP-1. Similar treatment effects were observed with mRNA expression for MCP-1 and osteopontin, a pro-inflammatory marker, in kidney tissue. Expression of pro-fibrotic markers in the kidneys showed an analogous pattern (FIG. 17). Overall, 10-nitro-9(E)-octadec-9-enoic acid at the lower dose significantly improved renal disease in the murine DOCA/salt model. In addition, 10-nitro-9(E)-octadec-9-enoic acid exerted benefits, such as anti-inflammatory and anti-fibrotic effects, that were not observed with the current standard of care, enalapril, likely due to different mechanisms of action for these two agents. This difference does, however, speak to the potential promise of 10-nitro-9(E)-octadec-9-enoic acid as a novel therapeutic approach for treating kidney injury.

Figure 18:
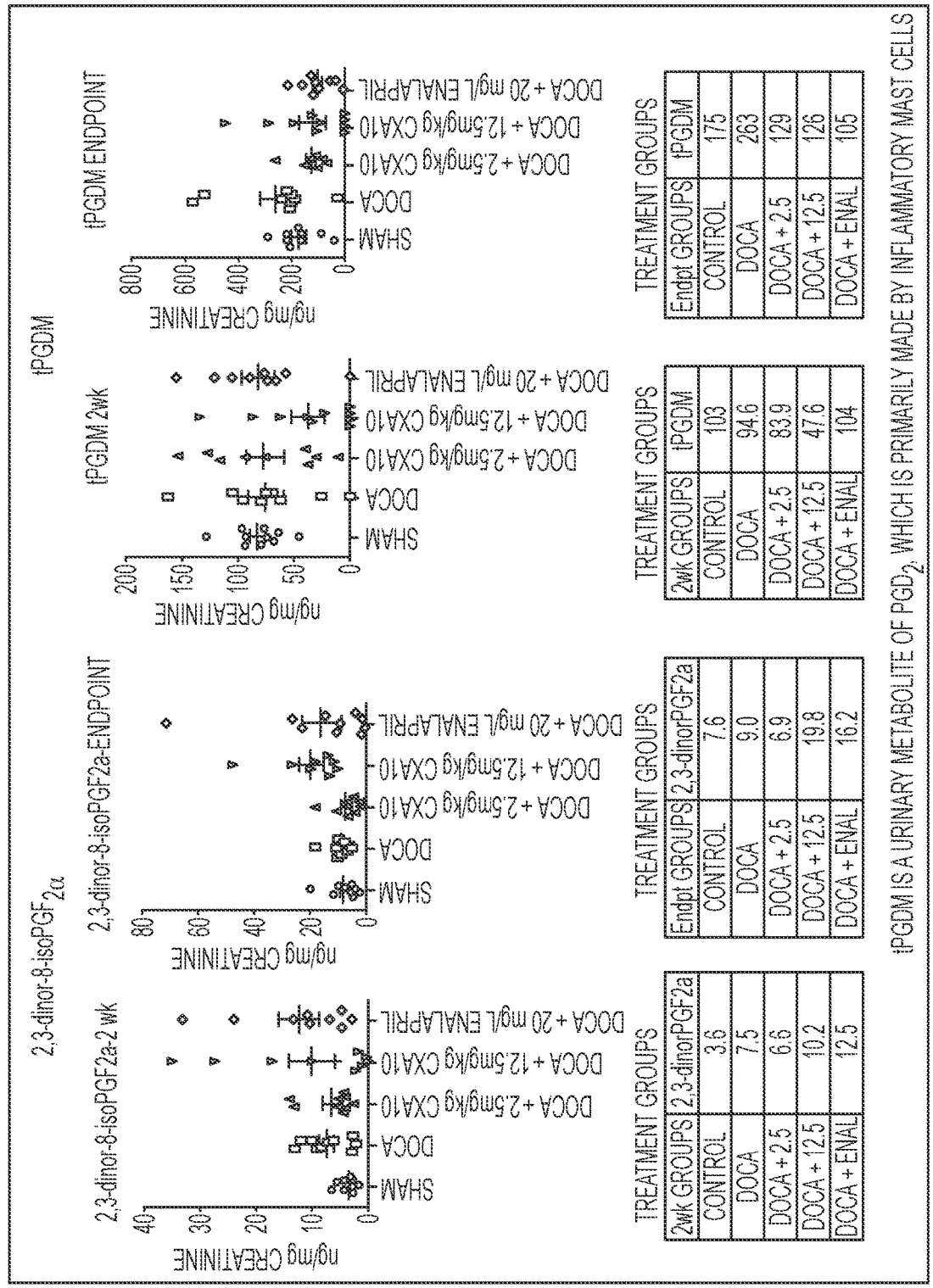
FIG. 18 shows the levels of urinary isoprostane following treatment obtained in the DOCA salt study. Reading from left to right, each graph depicts sham first (also known as control), DOCA second, DOCA+2.5 mg/ml CXA-10 (also known as CTX-10 2.5 mpk or 10-nitro-9(E)-octadec-9-enoic acid, 2.5 mg) third; DOCA+12.5 mg/ml CXA-10 (also known as CTX-10 12.5 mpk or 10-nitro-9(E)-octadec-9-enoic acid, 12.5 mg) forth; and DOCA+20 mg/ml Enalapril (also known as Enalpril) last.

Isoprostanes are a unique series of prostaglandin-like compounds formed in vivo via a non-enzymatic mechanism involving the free radical-initiated peroxidation of arachidonic acid. It has been shown that 8-iso-PGF2a (15-F2t-isoprostane) is the isoprostane that correlates best with increasing oxidative stress. Therefore, to assess the effect of treatment on oxidative stress, this isoform was measured using LC-MS. Also measured was tetranor-PGDM, a urinary metabolite of prostaglandin D2. While not statistically significant, the low dose 10-nitro-9(E)-octadec-9-enoic acid trended to have a greater reduction of 8-iso-PGF2a than the high dose or enalapril. On the other hand, elevated tetranor-PGDM was lowered with treatment of 10-nitro-9(E)-octadec-9-enoic acid and enalapril at the end time point (FIG. 18).

The findings suggest that low dose 10-nitro-9(E)-octadec-9-enoic acid (2.5 mg/kg) exerted renoprotective action in a chronic kidney disease model, as evidenced by improved renal pathological lesions, reduced albuminuria along with decreased urinary nephrin and MCP-1 excretion. Further supporting these observations are reduction in gene expression of pro-inflammatory cytokines, extracellular matrix and profibrotic factors, PAI-1, in mice dosed with low dose 10-nitro-9(E)-octadec-9-enoic acid, as compared with vehicle treated group. In addition, 10-nitro-9(E)-octadec-9-enoic acid may have a positive impact on cholesterol metabolism. The current results provide in vivo evidence that 10-nitro-9(E)-octadec-9-enoic acid is renoprotective in a chronic kidney disease model, which is likely through anti-inflammatory, anti-oxidative and anti-fibrosis effects. Interestingly, some beneficial effects of 10-nitro-9(E)-octadec-9-enoic acid can be differentiated from enalapril in this model.

Example 2: Effectiveness and Dose/Exposure-Response Relationship of 10-Nitro-9(E)-Octadec-9-Enoic Acid in Reducing Acute Kidney Injury in a Rat Model of Renal Ischemia/Reperfusion Prevention of ischemic reperfusion injury: Studies were performed to test the effectiveness and the dose/exposure-response relationship of 10-nitro-9(E)-octadec-9-enoic acid in reducing acute kidney injury in a rat model of renal ischemia/reperfusion when administered prior to the insult. A well-established and reproducible rat model of contrast-induced nephropathy was not available. Because ischemic/reperfusion injury is a facet of contrast-induced nephropathy, it was considered a reasonable alternative. In this model, the renal arteries of the rat were clamped for 35 min, followed by reperfusion. Serum creatinine was measured daily for 72 hours. The animals were then sacrificed for tissue and terminal plasma. 10-nitro-9(E)-octadec-9-enoic acid was administered over 15 min intravenously at various doses at one hour prior to the injury. The goals of this study was to: a) show efficacy of 10-nitro-9(E)-octadec-9-enoic acid in reducing acute kidney injury induced by the ischemic event when administered prior to the insult, b) define the minimally efficacious dose (and exposure) to help determine starting doses for the FIH trial in conjunction with toxicology studies, c) define the appropriate dosing regimen for clinical studies, and d) confirm the PK/PD relationship between the levels of 10-nitro-9(E)-octadec-9-enoic acid and the reduction of injury through the inhibition/activation of the appropriate signaling mediators.

10-nitro-9(E)-octadec-9-enoic acid (2.5, 12.5, and 25 mg/kg) was administered 1 hr prior to the ischemic event. Plasma samples were taken at 0, 24, 48, and 72 hr following the ischemic event, and serum creatinine levels were measured in batches using mass spectrometry to achieve precision in the results. The results are shown in FIG. 20. A statistically significant decrease in creatinine was observed in 10-nitro-9(E)-octadec-9-enoic acid-treated animals at 12.5 mg/kg following ischemia (ANOVA with Student-Newman-Keuls Multiple Comparisons Test, n=6, p<0.01 at 24 hr only).

Figure 21A:
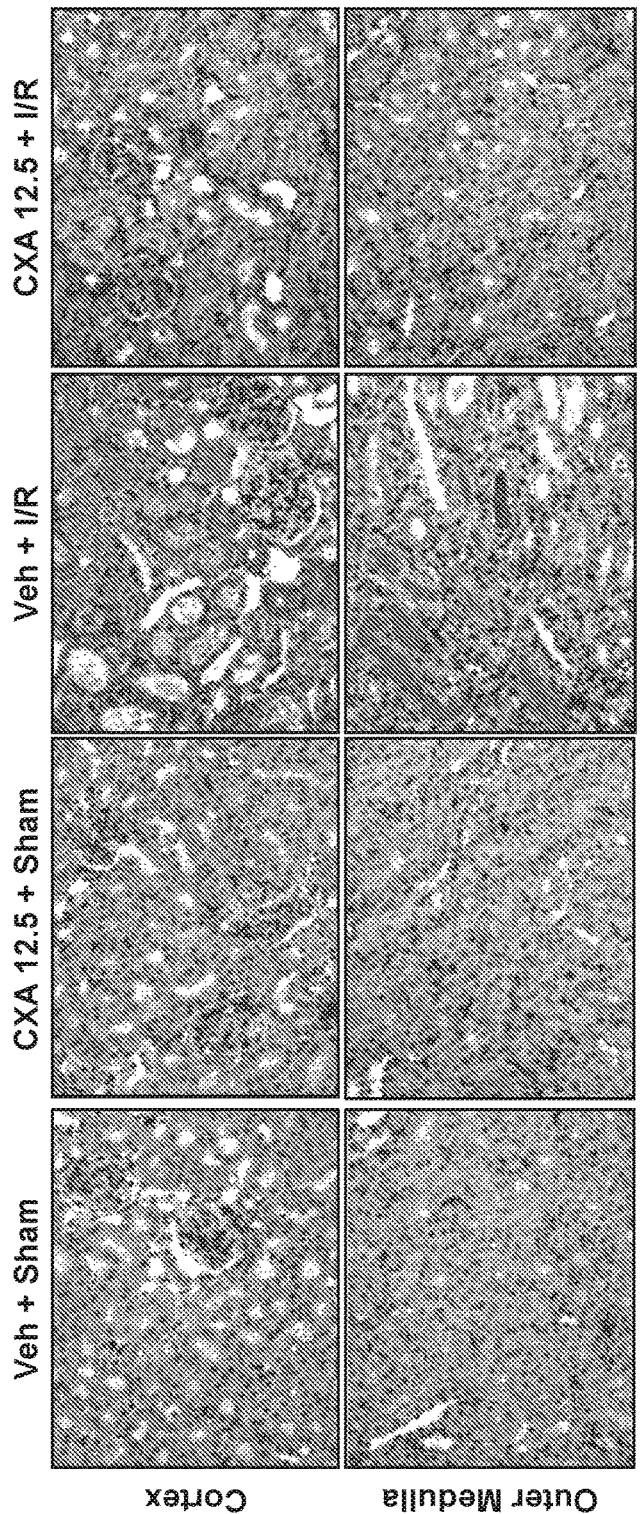
FIG. 21 shows the histological and quantitative evaluation of kidneys after I/R injury in rats treated with 12.5 mg/kg 10-nitro-9(E)-octadec-9-enoic acid in the rat ischemia reperfusion study.
Figure 21B:
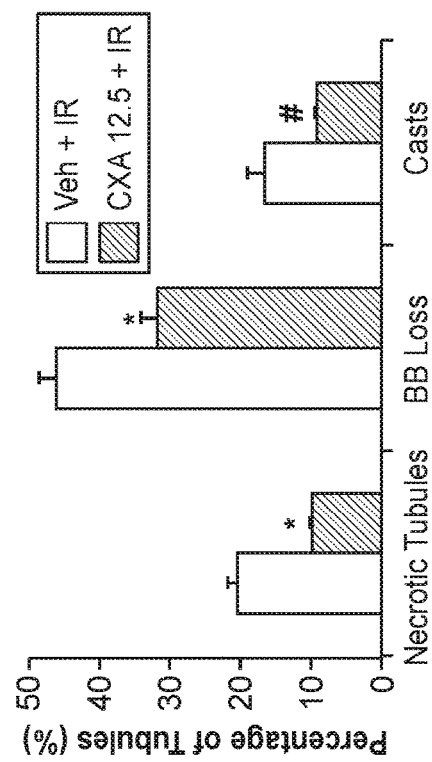

Periodic acid-Schiff staining of kidney sections and blinded scoring for renal structural injury from the treated and untreated groups showed alleviation of injury in rats treated with 12.5 mg/kg 10-nitro-9(E)-octadec-9-enoic acid (FIG. 21).

In this study, administration of 10-nitro-9(E)-octadec-9-enoic acid (12.5 mg/kg) intravenously to rats 1 hr prior to an acute kidney injury event significantly lowered the levels of serum creatinine, a marker of kidney injury, 24 hr following the event (Report CMP 2012-01). Additionally, 10-nitro-9(E)-octadec-9-enoic acid administration at the same dose preserved normal renal structure following I/R injury. The I/R model has known limitations because of the high degree of variability in causing kidney damage, as reflected in serum creatinine concentrations. Nonetheless, the blinded histopathological examination showed significant preservation of kidney tissues in 10-nitro-9(E)-octadec-9-enoic acid-treated animals at the 12.5 mg/kg dose indicating benefit at the level of the kidney despite a lack of effect on the functional measure, serum creatinine.

Example 3: Single-Center, Randomized, Double-Blind, Placebo-Controlled Study of Sequential Multiple Ascending Doses of Oral 10-Nitro-9(E)-Octadec-9-Enoic Acid in Obese Male Subjects The primary objectives of this study was to investigate the safety and tolerability of multiple ascending oral doses of 10-nitro-9(E)-octadec-9-enoic acid administered daily for 14 days; to evaluate the relationship between QTc (the corrected time between the start of the Q wave and the end of the T wave in the heart's electrical cycle) intervals and dose/exposure of 10-nitro-9(E)-octadec-9-enoic acid±metabolite(s) following administration of 10-nitro-9(E)-octadec-9-enoic acid daily for 14 days at multiple ascending dose levels; and to investigate the PK profile of 10-nitro-9(E)-octadec-9-enoic acid and its metabolite(s) following administration of 10-nitro-9(E)-octadec-9-enoic acid daily for 14 days at multiple ascending dose levels.

The secondary objectives of the study was to investigate the pharmacodynamics (PD) effects of 10-nitro-9(E)-octadec-9-enoic acid±metabolite(s) following oral administration of 10-nitro-9(E)-octadec-9-enoic acid daily for 14 days at multiple ascending dose levels on leptin, fasting blood glucose (FBG), total cholesterol, high density lipoproteins (HDL), low density lipoproteins (LDL) and triglycerides; to investigate the effects of 10-nitro-9(E)-octadec-9-enoic acid±metabolite(s) following oral administration of 10-nitro-9(E)-octadec-9-enoic acid daily for 14 days at multiple ascending dose levels on other ECG parameters (heart rate (HR), PR and QRS interval).

The exploratory objectives of this study was to investigate the PD effects of oral 10-nitro-9(E)-octadec-9-enoic acid±metabolite(s) following oral administration of 10-nitro-9(E)-octadec-9-enoic acid daily for 14 days at multiple ascending dose levels on gene expression and protein biomarkers.

The primary endpoints of this study included safety and tolerability, pharmacokinetics, and biomarkers. The safety and tolerability included physical examinations, adverse event (AE) reporting, vital signs (blood pressure, heart rate, respiratory rate), clinical laboratory values (hematology, biochemistry, and urinalysis) including serum magnesium and creatine phosphokinase (CPK), 12-lead electrocardiograms (ECGs) for safety assessments and QTcF measured on ECGs extracted from cardiac Holter monitoring. The pharmacokinetic measurements included maximum observed plasma drug concentration (Cmax), time to maximum plasma drug concentration (Tmax), terminal phase half-life (t½), area under the plasma drug concentration versus time curve (AUC0-last, AUC0-∞), clearance (CL/F), volume of distribution (Vd/F) and terminal elimination rate constant (λz).

Biomarker characterization included the following laboratory parameters: serum leptin, FBG, total cholesterol, HDL and LDL, triglycerides, HR, PR, QRS interval and T-wave morphology measured on ECGs extracted from cardiac Holter monitoring, measurements of serum RBP4, CRP, PAI-1, measurements of serum cytokines: IL-6, TNFα, MCP-1, measurements of the following biomarkers in whole blood by quantitative reverse transcriptase polymerase chain reaction (qRT-PCR) including: HO-1, NQ01, GCLM, HSP70 (HSP1A HSP1B, HSPA6), HSP22 (HSPB8) and HPS40 (DNAJA4), urine RBP4, MCP-1 and KIM-1, urinary exosomes by qRT-PCR including: HO-1, NQ01, GCLM, HSP70 (HSP1A HSP1B, HSPA6), HSP22 (HSPB8) and HPS40 (DNAJA4), gene and protein expression analyses by DNAseq, RNAseq, and western blots in PBMCs and ratio of EETs to DHETs in serum and urine.

This was a single-center, randomized, double-blind, placebo-controlled study of sequential multiple ascending doses of oral CXA-10 in obese male subjects. Eligible subjects included obese males age 19 to 57 years and BMI 27.0 to 39.5 $kg/m^2$. CXA-10 and placebo were provided as solutions in hard shell capsules. Three (3) cohorts of subjects were dosed once daily with CXA-10 for 14 days. The doses administered in this study were 25, 150 and 450 mg. Subjects enrolled in the highest dose level (450 mg) were administered 600 mg on day 1 then 450 mg for 13 days. This cohort (cohort 3) was given the option to receive an additional 450 mg dose on day 15 with a high fat (50%) breakfast.

Each cohort of subjects was randomized to receive CXA-10 (10 subjects) or placebo (4 or 5 subjects). Exposure to study medication is summarized in Table 3 below. Safety, pharmacokinetic (PK) and pharmacodynamic (PD) assessments were evaluated throughout the study. The last study visit occurred on Day 28. All subjects remained in the unit during the treatment period and were discharged approximately 24 hours after the last dose was administered. Food restrictions were incorporated to minimize variability in biomarker evaluation and body weight.

TABLE 3

STUDY DOSES.

| Cohort/Dose | CXA-10 N = subjects | Placebo N = subjects |
|---|---|---|
| 1/25 mg | 10 | 4 |
| 2/150 mg | 10 | 4 |
| 3/450 mg* | 10 | 5** |

*On day 1 cohort 3 received a single dose of 600 mg
**One subject in cohort 3 withdrew after day 9 because of family issues Specifically, subjects were admitted to the research unit on Day −2 to perform pre-dose (baseline) assessments. Some baseline assessments may have occurred on Day −1 or Day 1 prior to dosing.

On Day 1 at each dose level, subjects were randomized to receive 10-nitro-9(E)-octadec-9-enoic acid or placebo for 14 days (Days 1 through 14). Subjects remained at the unit until discharge on Day 15 after assessments were completed and reviewed. Subjects enrolled in cohort 3 were given the option to remain in the clinic through Day 16 and receive a standard FDA high fat (50%) breakfast approximately 30 minutes prior to dosing on Day 15. They remained in the unit until Day 16 (24 h after last dose on Day 15) before being discharged from the unit. The additional procedures on Day 15 and Day 16 were optional for subjects in cohort 3.

The decision to progress to the next dose level was based on a review of safety and available PK data by the Investigator and the Medical Monitor or Chief Medical Officer at Complexa after 10 subjects completed the assessments up through Day 14. For cohort 3, the decision to progress to another cohort could take place after 10 subjects have completed the assessments up through Day 15.

Safety and tolerability was evaluated throughout the study. Continuous Holter monitoring was performed on Days −1 and on Day 14 in all three cohorts. Continuous Holter monitoring could also be performed at highest dose cohort on an additional day between Days 2 and 4. The decision to conduct Holter monitoring and the actual day of the additional monitoring was determined based on emerging data.

Serial blood samples were collected from all subjects for PK and biomarker assessments prior to dosing and at various times throughout the study. Full PK profiles were obtained on Days 1 and 14. For subjects in cohort 3 who participate in the additional procedures on Day 15, full PK profiles were obtained on Days 1, 14, and 15. An abbreviated PK profile could also be obtained for the highest dose cohort only on one additional day. The actual day of PK sampling coincided with the additional day of Holter monitoring for the highest dose cohort. Subjects returned on Day 21 and Day 28 for PK, safety, and biomarker assessments.

Table 4 shows that the demographics were similar across all cohorts. No subjects dropped out of the study due to any adverse effects; one subject in cohort 3 left the study after day 9 because of unrelated issues. There were no deaths associated with this study.

TABLE 4

DEMOGRAPHIC DATA.

| Variable | Cohort 1 25 mg (n = 10) | Cohort 2 150 mg (n = 10) | Cohort 3 450 mg (n = 10) | Placebo* (n = 13) |
|---|---|---|---|---|
| Age (yrs) mean (range) | 37.5 (23, 48) | 38.1 (21, 54) | 38.3 (26, 54) | 39.3 (19, 57) |
| Sex | Males | Males | Males | Males |
| Race | | | | |
| Black/African American | 50% | 50% | 60% | 53.8% |
| White | 50% | 50% | 40% | 46.2% |
| BMI (kg/m$^2$) mean (range) | 30.2 (27, 38.7) | 28.6 (27, 33.2) | 30.1 (27.3, 39.5) | 30.6 (27.6, 37.4) |

*4 placebo subjects were randomized to a cohort

Table 5 provides the most common adverse events (AEs) seen during the study, depicted as number as well as percentage effected. Included are events that occurred in greater than 20% of the participants. The most common GI AEs were diarrhea and nausea. The most common nervous system AE was presyncope. The most common general disorder AE was fatigue. The most common muscle and CT disorder AE was back pain.

TABLE 5

MOST COMMON ADVERSE EFFECTS.

| | Cohort 1 25 mg (N = 10 | Cohort 2 150 mg (n = 10) | Cohort 3 450 mg (n = 10) | Placebo* (n = 13) |
|---|---|---|---|---|
| GI | 2 (20%) | 5 (50%) | 9 (90%) | 2 (15.4%) |
| Nervous System | 0 (0%) | 1 (10%) | 4 (40%) | 3 (23.1%) |
| Skin and SQ disorders | 2 (20%) | 0 (0%) | 1 (10%) | 1 (7.7%) |
| General Disorders | 1 (10%) | 0 (0%) | 3 (30%) | 0 (0%) |
| Muscle and CT disorders | 2 (20%) | 0 (0%) | 2 (20%) | 0 (0%) |

*4 placebo subjects were randomized to a cohort

The adverse effect of diarrhea and nausea were dose limiting. In general, the diarrhea began within 1 to 3 hours after dosing and resolved within 4 hours. Diarrhea seen was grade 1 or 2 in intensity (began as loose stools that became watery) and did not worsen with increasing dose. Table 6 shows the distribution of said GI related AEs.

TABLE 6

GI RELATED AES.
GI related AEs

| Placebo | 1 subject had nausea |
|---|---|
| Cohort 1 (25 mg) | 1 subject had nausea |

TABLE 6-continued

GI RELATED AES.
GI related AEs

| | |
|---|---|
| Cohort 2 (150 mg) | 5 subjects had diarrhea: 1 subject had diarrhea ~2 hr post dosing on each day. All other diarrhea AEs were sporadic, no subject had nausea |
| Cohort 3 (450 mg) | 9 subjects had diarrhea, 4 subjects had nausea |
| Cohort 3 (450 mg w food) | 3 subjects had diarrhea, 1 had nausea |

There were no clinically significant findings in the clinical laboratory, vital signs or ECG evaluations. There were no abnormalities in CPK (muscle enzyme) or magnesium serum levels; no effect on clinical chemistry including hepatic and renal parameters; no effect on WBCs including lymphocytes and monocytes. There was a slight decrease in HBG, HCT and RBC concentration during treatment with 10-nitro-9(E)-octadec-9-enoic acid 450 mg compared to placebo treated subjects. There were no effect on vital signs or physical examinations; no prolongation of QTc interval observed on routine ECG evaluation after dosing for 15 days; no prolongation of QTc interval based on ECG extraction from continuous 24-hour Holter monitoring. Diarrhea is dose limiting tolerability; ameliorated, but not completely prevented when administered with food. A high fat meal (50%) increases exposure to drug and delays absorption.

Figure 22:
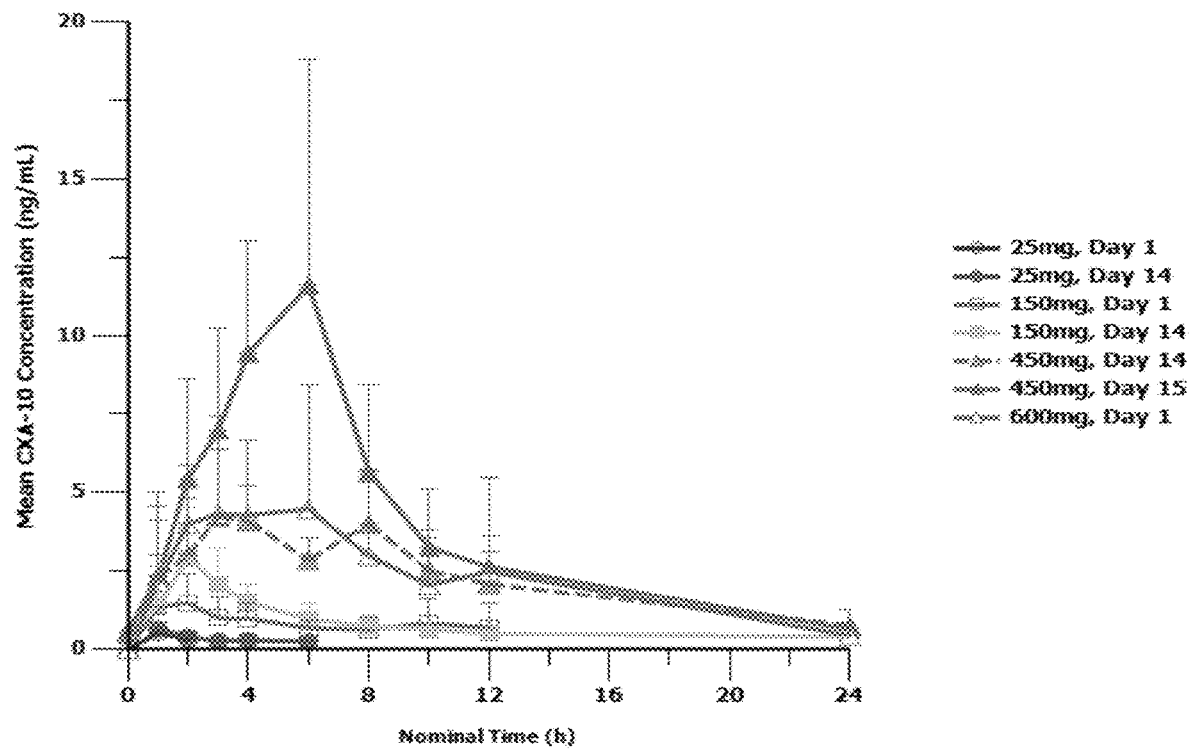
FIG. 22 shows the mean concentration-time PK profiles for all 3 cohorts in the multiple ascending dose study of 10-nitro-9(E)-octadec-9-enoic acid in obese males, on day 1 and day 14 and day 15 fed. The lines within this graph can be distinguished starting from the bottom, the bottom most open circles represent day 1 with 25 mg treatment, the filled circles represent day 14 with 25 mg treatment; followed by the open squares that represent day 1 with 150 mg treatment, the filled squares represent day 14 with 150 mg treatment; followed by the open triangles that represent day 1 with 600 mg treatment, the filled triangles represent day 14 with 450 mg treatment; the top most filled triangles represent day 15 with 150 mg treatment.

The pharmacokinetics profiles of 10-nitro-9(E)-octadec-9-enoic acid generally show dose proportional concentration-times with minimal accumulation, see FIG. 22. Table 7 provides data for days 21 and 28. Under fed conditions, $C_{max}$ increased about 2-fold and AUC increased about 1.7-fold with a delay in absorption. Median $T_{max}$ increased from 3 to 6 hours between fasted and fed conditions.

TABLE 7

CONCENTRATION-TIME PK PROFILES FOR DAYS 21 AND 28.

| | Day 21 (ng/mL) | Day 28 (ng/mL) |
|---|---|---|
| 25 mg | (n = 1) 0.17 | 0 |
| 150 mg | (n = 7) 0.33 | (n = 5) (0.39 |
| 450 mg | (n = 8) 0.38 | (n = 9) 0.30 |

Figure 23:
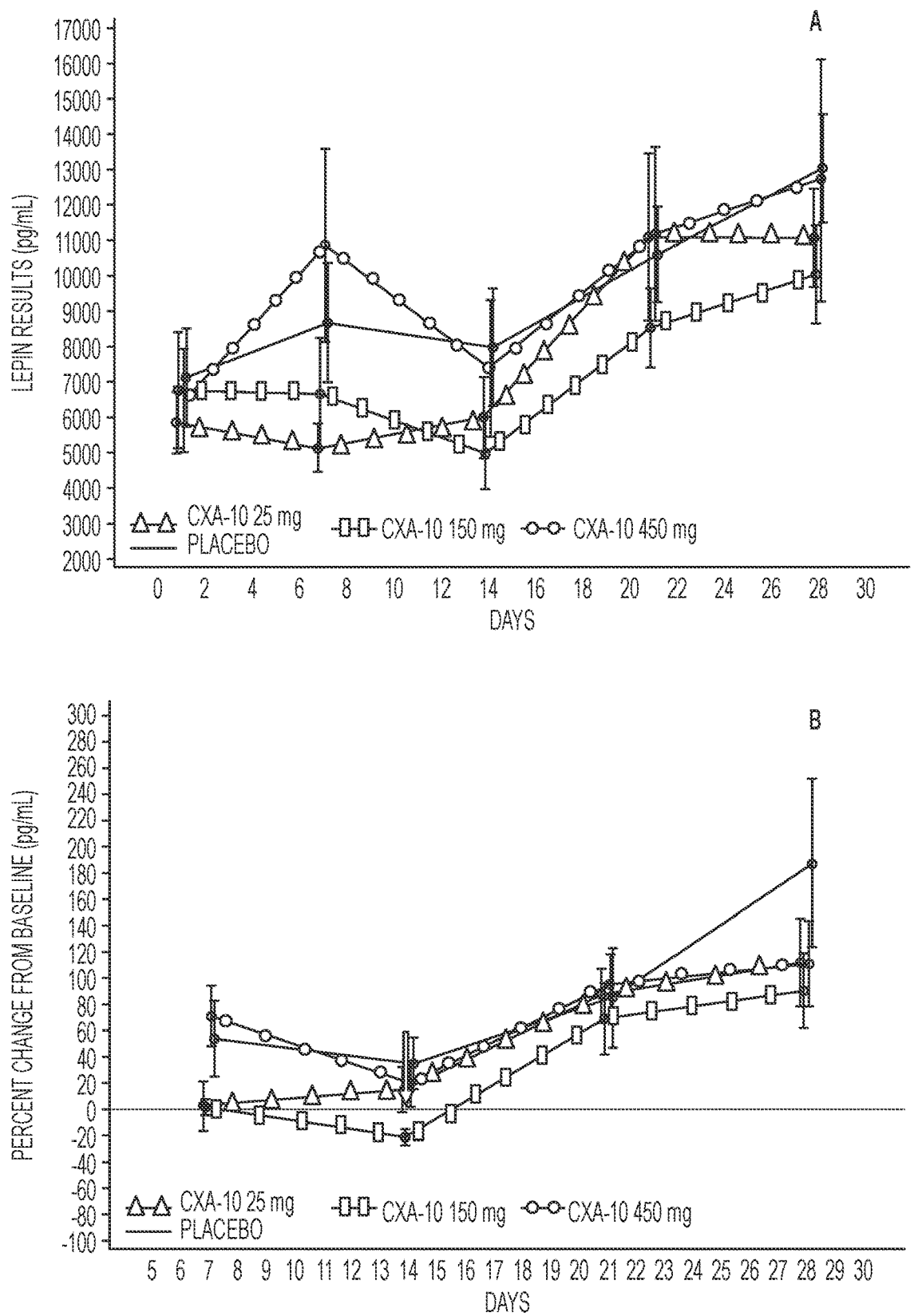
FIG. 23 shows the Leptin concentrations as the mean by treatment (A) and the percent change from baseline treatment (B) from the multiple ascending dose study of 10-nitro-9(E)-octadec-9-enoic acid in obese males. In both graphs a black line represents placebo, a dark gray triangle represents CXA-10 (10-nitro-9(E)-octadec-9-enoic acid) 25 mg, a light gray rectangle represents CXA-10 (10-nitro-9(E)-octadec-9-enoic acid) 150 mg, and a light gray circle represents CXA-10(10-nitro-9(E)-octadec-9-enoic acid) 450 mg.

Leptin concentrations decreased 21.5% from baseline at day 14 during treatment with 10-nitro-9(E)-octadec-9-enoic acid 150 mg compared to an increase of 35% in placebo treated obese subjects, see FIG. 23B and Table 8. FIG. 23A is a graph of ng/ml of leptin over time by treatment.

TABLE 8

LEPTIN CONCENTRATIONS AND PERCENT CHANGE AT DAY 14.

| | Cohort 2 150 mg (n = 10) % change from baseline | Placebo (n = 12) | LS Mean Difference (pg/mL) (CI) |
|---|---|---|---|
| Day 14 | −21.5 | +35 | −56.5 (−140.5, 27.5) |

Figure 24:
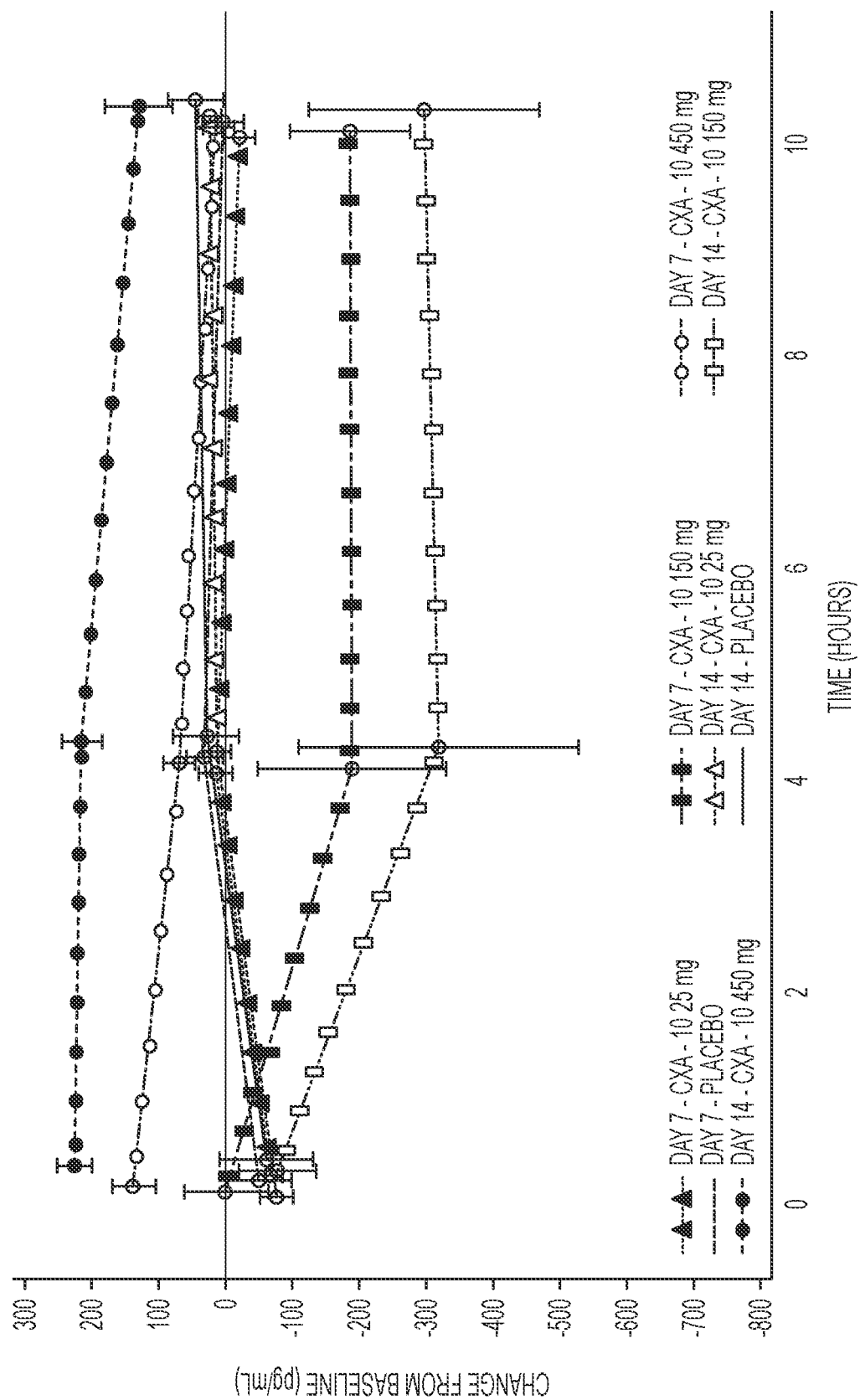
FIG. 24 shows the MCP-1 change from baseline by treatment from the multiple ascending dose study of 10-nitro-9(E)-octadec-9-enoic acid in obese males. A dashed line is Day 7-Placebo, a solid line is Day 14-Placebo, a dashed line with dark gray triangles is Day 7-CXA-10 (10-nitro-9(E)-octadec-9-enoic acid) 25 mg, a solid line with dark gray triangles is Day 14-CXA-10 (10-nitro-9(E)-octadec-9-enoic acid) 25 mg, a dashed line with light gray rectangles is Day 7-CXA-10 (10-nitro-9(E)-octadec-9-enoic acid) 150 mg, a solid line with light gray rectangles is Day 14-CXA-10 (10-nitro-9(E)-octadec-9-enoic acid) 150 mg, a dashed line with light gray circles is Day 7-CXA-10 (10-nitro-9(E)-octadec-9-enoic acid) 450 mg, a solid line with light gray circles is Day 14-CXA-10 (10-nitro-9(E)-octadec-9-enoic acid) 450 mg.

The mean change from baseline of MCP-1 during treatment with 150 mg 10-nitro-9(E)-octadec-9-enoic acid was significantly different compared to placebo treated obese subjects, see FIG. 24 and Table 9. Time points taken at 0, 4 and 10 hours. Normal range for MCP-1 is 200-722 pg/mL.

TABLE 9

MCP-1 CONCENTRATION AT DAY 14.

| Time | LS Mean Difference (pg/mL) (CI) |
|---|---|
| Day 14 (0-10 hr) | −228.5 (−387.2, −69.77) |

Figure 25:
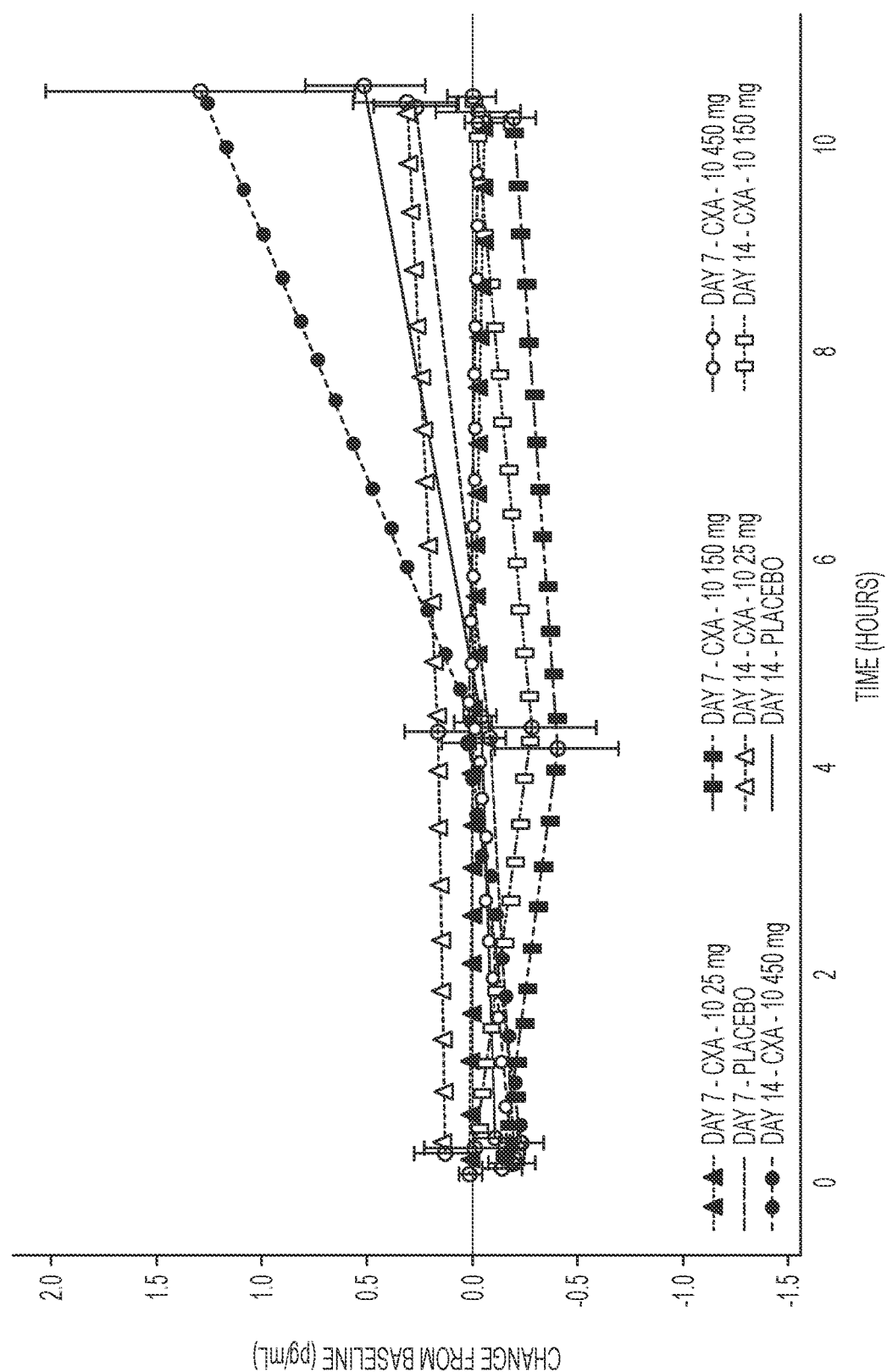
FIG. 25 shows the IL-6 concentrations as mean change from baseline by treatment from the multiple ascending dose study of 10-nitro-9(E)-octadec-9-enoic acid in obese males. A dashed line is Day 7-Placebo, a solid line is Day 14-Placebo, a dashed line with dark gray triangles is Day 7-CXA-10 (10-nitro-9(E)-octadec-9-enoic acid) 25 mg, a solid line with dark gray triangles is Day 14-CXA-10 (10-nitro-9(E)-octadec-9-enoic acid) 25 mg, a dashed line with light gray rectangles is Day 7-CXA-10 (10-nitro-9(E)-octadec-9-enoic acid) 150 mg, a solid line with light gray rectangles is Day 14-CXA-10 (10-nitro-9(E)-octadec-9-enoic acid) 150 mg, a dashed line with light gray circles is Day 7-CXA-10 (10-nitro-9(E)-octadec-9-enoic acid) 450 mg, a solid line with light gray circles is Day 14-CXA-10 (10-nitro-9(E)-octadec-9-enoic acid) 450 mg.

IL-6 concentrations showed a trend to decrease from baseline in obese subjects treated with 10-nitro-9(E)-octadec-9-enoic acid 150 mg on days 7 and 14, see FIG. 25. Normal range for IL-6 is 0-2 pg/mL.

Figure 26:
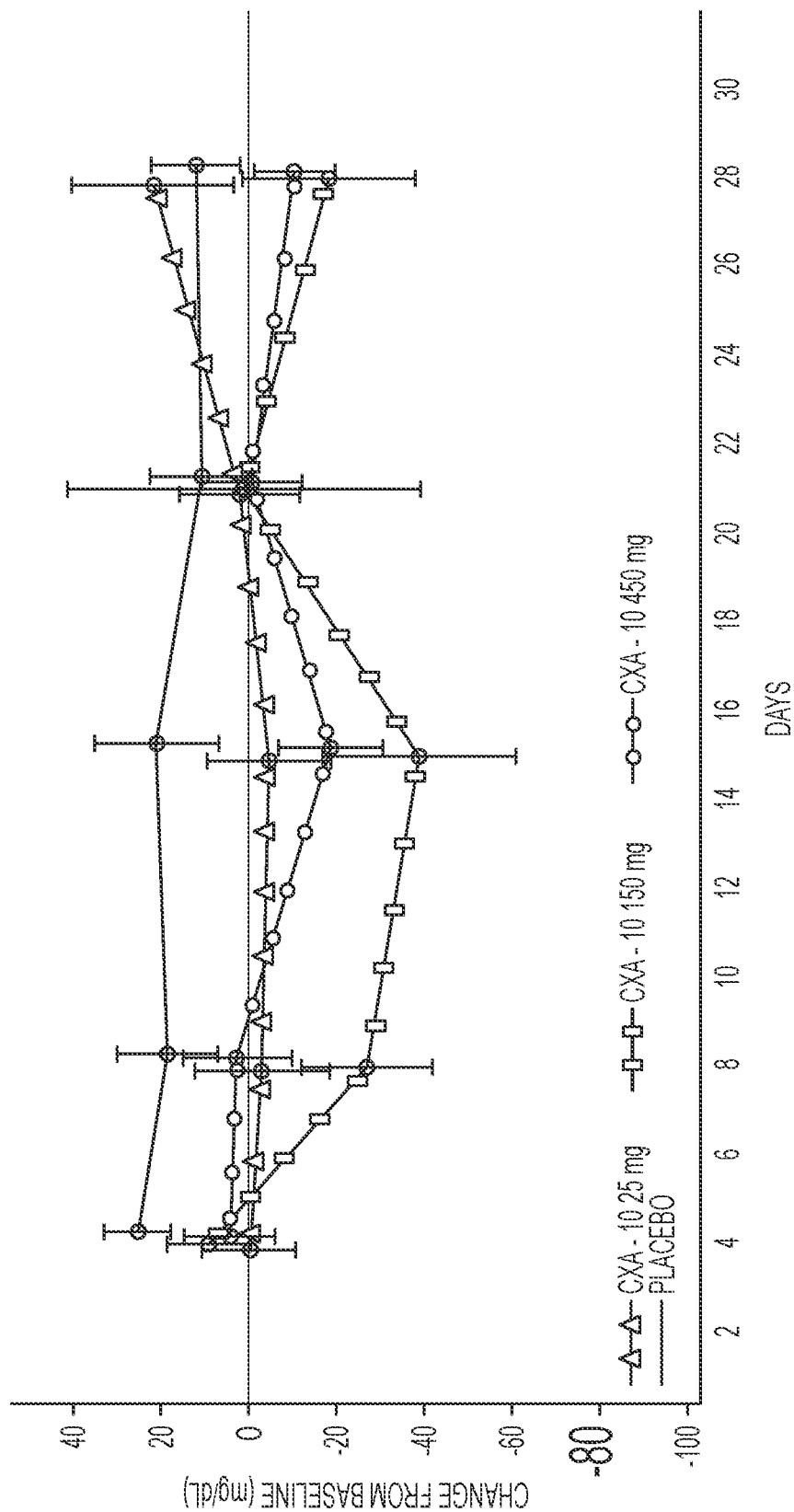
FIG. 26 shows the triglyceride change from baseline by treatment from the multiple ascending dose study of 10-nitro-9(E)-octadec-9-enoic acid in obese males. Within this graph, a black line represents placebo, a dark gray triangle represents CXA-10 (10-nitro-9(E)-octadec-9-enoic acid) 25 mg, a light gray rectangle represents CXA-10 (10-nitro-9(E)-octadec-9-enoic acid) 150 mg, and a light gray circle represents CXA-10(10-nitro-9(E)-octadec-9-enoic acid) 450 mg.

The triglyceride change from baseline decreased in 10-nitro-9(E)-octadec-9-enoic acid treated obese subjects and was significantly different at days 8 and 15 in obese subjects administered 150 mg 10-nitro-9(E)-octadec-9-enoic acid, see FIG. 26 and Table 10. Normal range for triglycerides is greater than 150 mg/dL.

TABLE 10

MEAN DIFFERENCE IN TRIGLYCERIDES.

| Time | LS Mean Difference (pg/mL) (CI) |
|---|---|
| Day 8 | −45.44 (−87.38, −3.50) |
| Day 15 | −59.6 (−102.3, −16.91) |

Figure 27:
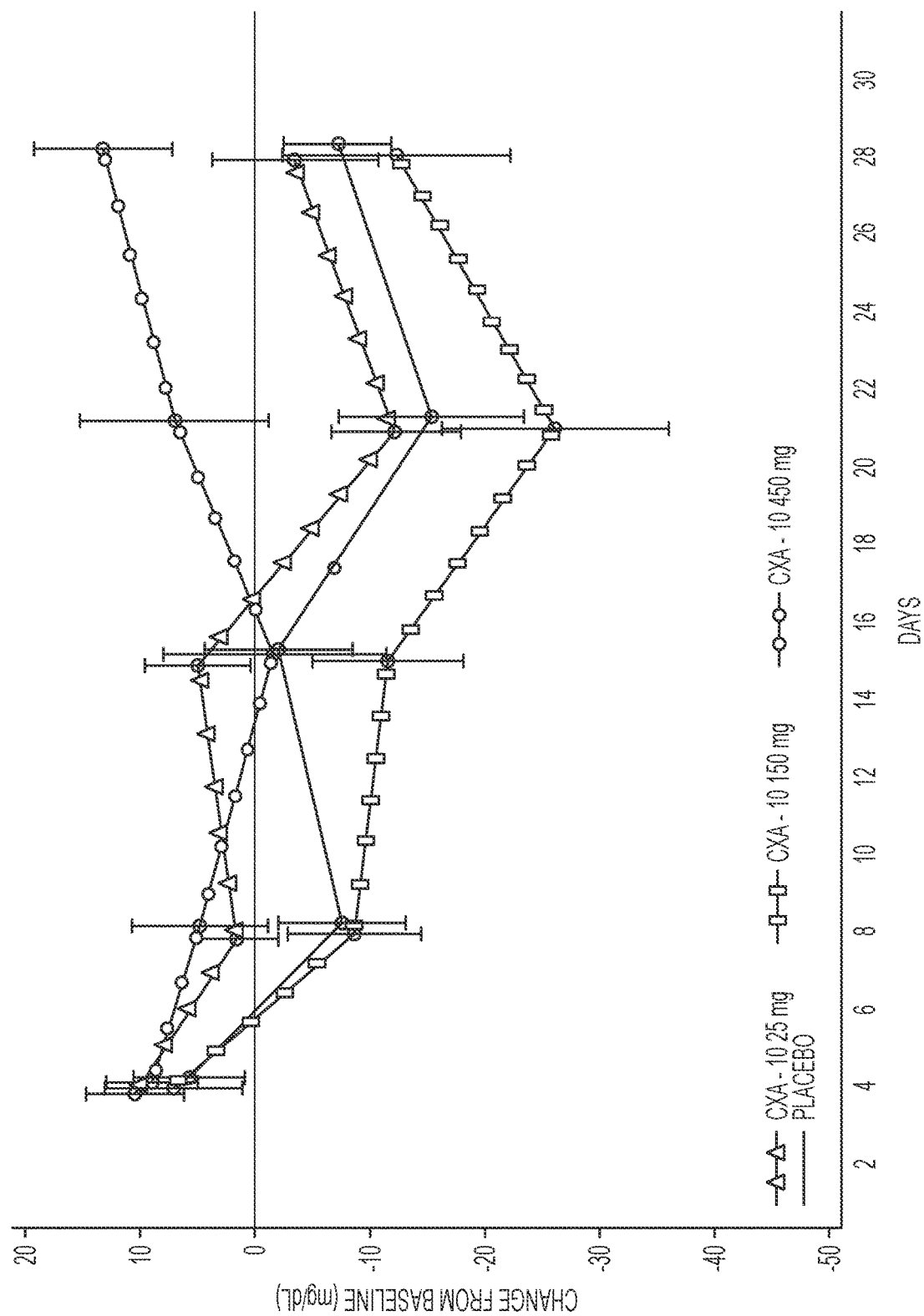
FIG. 27 shows cholesterol concentrations mean change from baseline by treatment from the multiple ascending dose study of 10-nitro-9(E)-octadec-9-enoic acid in obese males. Within this graph, a black line represents placebo, a dark gray triangle represents CXA-10 (10-nitro-9(E)-octadec-9-enoic acid) 25 mg, a light gray rectangle represents CXA-10 (10-nitro-9(E)-octadec-9-enoic acid) 150 mg, and a light gray circle represents CXA-10(10-nitro-9(E)-octadec-9-enoic acid) 450 mg.

Cholesterol concentrations showed a trend to decrease from baseline in obese subjects treated with 10-nitro-9(E)-octadec-9-enoic acid 150 mg, see FIG. 27.

Treatment with 10-nitro-9(E)-octadec-9-enoic acid in obese subjects was shown to effect both metabolic and inflammatory pathways consistent with the effects seen in numerous animal models. These markers include Leptin for metabolic abnormalities, inflammatory serum markers MCP-1 and IL-6 for NF-κB inhibition and cholesterol and triglycerides for lipid effects.

There was a consistent decrease across all 5 biomarkers (leptin, cholesterol, triglycerides, MCP-1 and IL6) at the 150 mg dose group. Similar reductions in biomarkers were not uniformly observed at the 450 mg dose group.

Example 4: Study of the Pharmacokinetic Interaction of 10-Nitro-9(E)-Octadec-9-Enoic Acid Administered to Steady State with Pravastatin and Vytorin® (Simvastatin and Ezetimibe) in Healthy Males The mechanism of action of 10-nitro-9(E)-octadec-9-enoic acid is to induce the activity of the post-translational modulator Nrf2. Nrf2 may cause induction of transporters involved in drug metabolism, specifically multidrug resistance proteins 1-4 (MRP1-4), organic anion transporting polypeptide 1B1 (OATP1B1), and uridine diphosphate-glucuronosyl-transferase (UGT). Drugs metabolized through these transporters are used frequently in the treatment of patients with CKI (ACEi, ARB and statins). The overall design of the trial was to administer drugs that are metabolized through these transporters to quantify the impact 10-nitro-9(E)-octadec-9-enoic acid may have on the exposure of these drugs. The results from this study may be used to guide dose adjustments for concomitant medications used in the CKI population during treatment with 10-nitro-9(E)-octadec-9-enoic acid.

This was an exploratory study in a small, well controlled group of healthy subjects to explore the effect of 10-nitro-9(E)-octadec-9-enoic acid on pravastatin and Vytorin® (combination of simvastatin and ezetimibe). These drugs were selected because they are selective substrates for UGT, transporters and cytochrome P450 3A4, although there are no data to indicate Nrf2 has an effect on CYP450 3A4. Based on in vitro CYP450 evaluation, 10-nitro-9(E)-octadec-9-enoic acid should not have an effect on CYP450 3A4 ($IC_{50}$>33µ), nor on any other isoform.

Pravastatin is not significantly mediated by CYP enzymes but is a substrate of MRP2 and the uptake transporter OATP2, which makes it a specific probe for transporter effects.

Vytorin® (simvastatin and ezetimibe combination product) will allow for the administration of a single dosage form for the examination of 2 drugs (simvastatin and ezetimibe).

Simvastatin is a CYP3A4 and an OATP1B1 substrate. No effect of Nrf2 is expected on CYP3A4; therefore, simvastatin may be a specific probe for OATP1B1. A study has been reported in the literature on the effects of the inducer rifampin on simvastatin exposure showing that the exposure decreased to $\frac{1}{10}^{th}$ of that before rifampin treatment.

Ezetimibe is primarily metabolized in the small intestine and liver via glucuronide conjugation (a phase II reaction) with subsequent biliary and renal excretion. Minimal oxidative metabolism (a phase I reaction) has been observed; therefore, this drug could be a probe for UGT. Ezetimibe and ezetimibe-glucuronide are the major drug-derived compounds detected in plasma, constituting approximately 10% to 20% and 80% to 90% of the total drug in plasma, respectively. PK analysis of both ezetimibe and ezetimibe-glucuronide studied.

One objective of this study was To investigate the effect of steady state concentrations of CXA-10, after multiple oral doses, on the pharmacokinetic (PK) profiles of pravastatin and the two components of Vytorin® (combination of simvastatin and ezetimibe)

Another objective of this study was to investigate the safety and tolerability of multiple oral doses of CXA-10 alone and when administered with pravastatin and Vytorin®.

Figure 28:
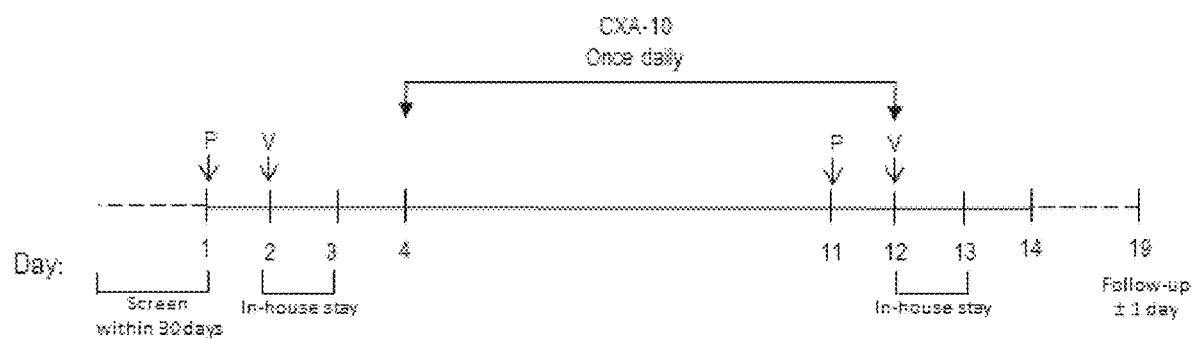
FIG. 28 shows the study design and timeline for the pharmacokinetic interaction of 10-nitro-9(E)-octadec-9-enoic acid administered to steady state with pravastatin and Vytorin® (Simvastatin and Ezetimibe) in Healthy Males study. P is pravastatin and V is Vytorin®.

This was a single-center, open-label study in 10 healthy male subjects age 19 to 31 years and BMIs 21 to 26 kg/m² received single doses of pravastatin (40 mg) and Vytorin® (ezetimibe/simvastatin 10 mg/20 mg/day) alone and after the administration of 10-nitro-9(E)-octadec-9-enoic acid oral 150 mg daily 8 days and 9 days respectively after the first 10-nitro-9(E)-octadec-9-enoic acid dose (i.e. day 11 and day 12 of the study). All subjects received pravastatin (40 mg) only on Day 1 and Vytorin® (ezetimibe/simvastatin 10 mg/20 mg/day) only on Day 2. On Days 4 to 10, subjects received 150 mg oral 10-nitro-9(E)-octadec-9-enoic acid daily with food. On Day 11, subjects received 10-nitro-9(E)-octadec-9-enoic acid along with a single dose of pravastatin. On Day 12, subjects received 10-nitro-9(E)-octadec-9-enoic acid along with a single dose of Vytorin®. The study design is illustrated in FIG. 28.

Specifically, eligible subjects reported to the research unit on Day −1 to perform pre-dose (baseline) assessments after which they were discharged.

After an overnight fast, subjects received pravastatin 40 mg with food on Day 1 and remained in the unit for approximately 10 h for PK sampling of pravastatin levels after which they were discharged. After an overnight fast on Day 2, subjects returned to the unit to receive Vytorin® with food. PK samples were collected for simvastatin and ezetimibe levels up to 24-h after Vytorin® dosing while subjects remained in the unit overnight. Subjects were discharged on Day 3, after the 24-h PK sample after Vytorin® dosing was collected. On the days pravastatin and Vytorin® were administered, subjects received a standard FDA high fat (50%) breakfast approximately 30 minutes prior to dosing. The 24-h PK samples for pravastatin and predose sample (0 h) for pravastatin and Vytorin® were collected prior to dosing on those respective days.

After an overnight fast, subjects reported to the unit in the morning of Day 4 and had a 48-h PK sample collected for measuring simvastatin and ezetimibe levels after Vytorin® dosing. They then received a standard FDA high fat (50%) breakfast followed by an oral dose of 150 mg of 10-nitro-9(E)-octadec-9-enoic acid. The high fat breakfast was given approximately 30 minutes prior to dosing with 10-nitro-9(E)-octadec-9-enoic acid.

Subjects were asked to report to the unit in a fasted state (overnight fast) daily for 6 more days (Days 5 to 10) to receive 10-nitro-9(E)-octadec-9-enoic acid once-daily with food as on Day 4 and for safety assessments. On Day 10 subjects remained in the unit to collect PK samples for 10-nitro-9(E)-octadec-9-enoic acid levels. The first PK sample (0 h) was collected prior to 10-nitro-9(E)-octadec-9-enoic acid dosing. Subjects were discharged after the collection of the last PK sample (12 h) for that day.

On the morning of Day 11, subjects received 10-nitro-9(E)-octadec-9-enoic acid with food as on Day 4 and have a PK sample collected for 10-nitro-9(E)-octadec-9-enoic acid (24 h). They also received pravastatin followed by PK sampling for pravastatin levels for 10 hours. The 24-h PK samples for 10-nitro-9(E)-octadec-9-enoic acid and predose (0 h) for pravastatin were collected prior to dosing on Day 11. Pravastatin was administered at approximately the same time after the meal as when administered on Day 1. The subjects were discharged after the last PK sampling.

After an overnight fast, subjects returned to the unit on Day 12 to receive 10-nitro-9(E)-octadec-9-enoic acid with food as on Day 4. They also received Vytorin® on Day 12. PK samples for simvastatin and ezetimibe levels were collected throughout the 24 h period after Vytorin® dosing while subjects remained in the unit overnight. The predose (0 h) Vytorin® PK sample was collected prior to dosing. Vytorin® was administered at approximately the same time after the meal same as when administered on Day 2. Subjects were discharged on Day 13, after the 24-h PK sample after Vytorin® dosing was collected. Subjects returned to the unit on the morning of Day 14 for the collection of the last PK sample (48 h) for simvastatin and ezetimibe levels.

Safety and tolerability was evaluated throughout the study. The timing of discharge was determined by the Investigator or designee based on safety and tolerability assessment. On dosing days, subjects remained in the research unit for a minimum of 1 h after dosing prior to discharge. On Day 4, on the first day of 10-nitro-9(E)-octadec-9-enoic acid dosing, subjects remained in the unit for 4 to 6 h after dosing prior to discharge to assess safety and tolerability.

Subjects returned to the unit for a follow-up visit on Day 19±1 day (approximately 7 days after the last dose of the study medication).

Safety and PK assessments were evaluated throughout the study. During the in-house portion of the study, urine was collected over the 24-h period on Day 2 and Day 12. Urine samples obtained from the 24-h collection on each study day were used to measure the levels of creatinine to determine whether the administration of 10-nitro-9(E)-octadec-9-enoic acid inhibited the OCT2 transporter.

Safety was evaluated by physical examinations; adverse events (AEs); vital signs (blood pressure, heart rate, respiratory rate); clinical laboratory values (hematology, biochemistry, and urinalysis), specifically, serum Mg and CPK and electrocardiograms (ECGs).

Blood samples for the determination of plasma concentrations of pravastatin, simvastatin and simvastatin acid, ezetimibe and ezetimibe-glucuronide, 10-nitro-9(E)-octadec-9-enoic acid and its metabolite(s) were collected at the approximate nominal times listed in FIG. 29.

A total of 3 of 10 subjects in the study reported AEs. One subject had nasopharyngitis, 1 subject had abdominal discomfort after the administration of pravastatin and 1 subject had 7 AEs that may have been attributed to Norovirus infection (abdominal discomfort, diarrhea, nausea, vomiting, feeling of body temperature change and decreased appetite). GI AEs related to 10-nitro-9(E)-octadec-9-enoic acid observed in previous studies were not observed in this study. Thus these events may have been prevented by administering 10-nitro-9(E)-octadec-9-enoic acid with food. All reported AEs were mild to moderate in intensity and all resolved without sequelae.

There were no serious AEs, withdrawals due to AEs or deaths during the reporting period.

Triplicate ECGs were obtained just prior to the start of dosing on Day 1 and single ECGs were obtained at all other time points. The average of the 3 ECG interval measurements at the pre-dose time point was considered as baseline. All 12-Lead ECGs were obtained after the subject has rested in a fully supine position for at least 10 minutes. There were no clinically significant abnormalities reported on any electrocardiogram (ECG) parameter. There were no QT/QTcF interval prolongations observed during the study.

There were no clinically significant abnormalities reported on vital signs and no clinically significant findings in clinical laboratory evaluations including serum Mg and CPK. The study also examined the 24-h urine total creatinine excretion prior to and following administration of 10-nitro-9(E)-octadec-9-enoic acid to examine the effects of 10-nitro-9(E)-octadec-9-enoic acid, if any, either directly on OCT2 transporters to reduce creatinine secretion or through enhanced creatinine generation. There were no changes in serum creatinine levels nor any relevant changes in 24-hour urine creatinine excretion measurements as a result of 10-nitro-9(E)-octadec-9-enoic acid administration.

10-nitro-9(E)-octadec-9-enoic acid concentrations were measured in human plasma by MicroConstants Inc. (San Diego Calif.) using a validated reversed-phase LC-MS/MS assay. The bioanalytical assay is selective for 10-nitro-9(E)-octadec-9-enoic acid only concentrations. Therefore, all references to plasma 10-nitro-9(E)-octadec-9-enoic acid refer to the parent (10-nitro-9(E)-octadec-9-enoic acid) concentrations and not to metabolites. Concentrations of pravastatin and 3-alpha-hydroxy pravastatin, ezetimibe (total) and unconjugated ezetimibe, simvastatin and simvastatin-beta-hydroxyl acid were measured in human plasma by inVentiv Health Clinique Inc (Quebec Canada) using a validated LC/MS/MS assay. Serial blood samples were collected from all subjects for PK assessments at various times throughout the study as noted above.

Figure 30:
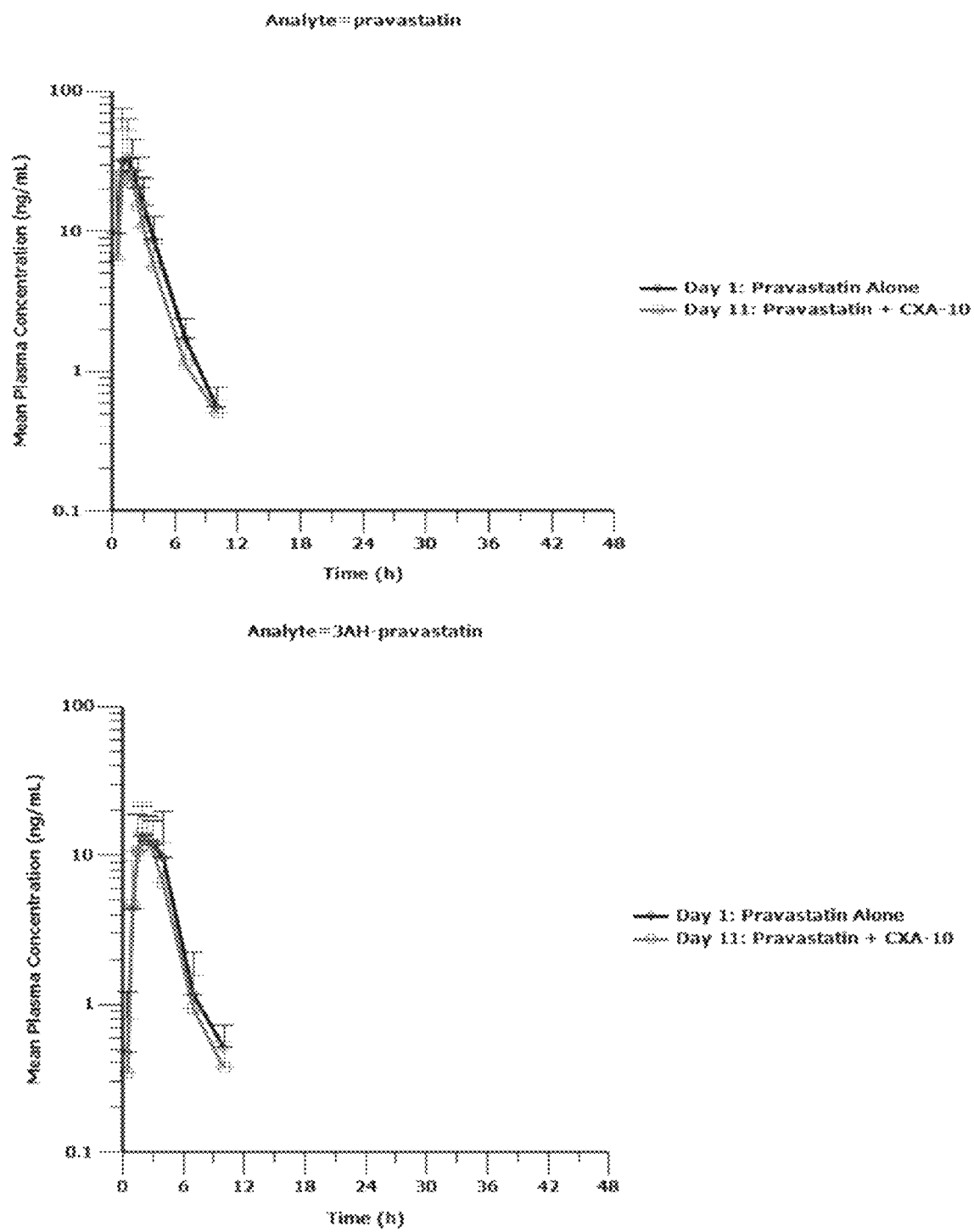
FIG. 30 shows mean (+SD) plasma pravastatin concentration-time profiles following oral administration of 40 mg of pravastatin (A) and 3-alpha-hydroxy pravastatin (B) from the study of the pharmacokinetic interaction of 10-nitro-9(E)-octadec-9-enoic acid administered to steady state with pravastatin and Vytorin® (Simvastatin and Ezetimibe) in Healthy Males. Day 1: Pravastatin Alone is represented by a dark grey line with and unshaded circle and Day 11.

FIGS. 30 to 32 show pharmacokinetic profiles of the analyte alone and analyte after administration of 10-nitro-9(E)-octadec-9-enoic acid. FIG. 33 is a table that shows the summary statistics of test (analyte when administered with 10-nitro-9(E)-octadec-9-enoic acid) to reference (analyte alone).

Mean $C_{max}$ and $AUC_{(0-t)}$ of pravastatin and its metabolite decreased 20% and 25%, respectively on co-administration with 10-nitro-9(E)-octadec-9-enoic acid. Mean $C_{max}$ and $AUC_{(0-t)}$ of ezetimibe decreased 20% and 5%, respectively on co-administration with 10-nitro-9(E)-octadec-9-enoic acid. Mean $C_{max}$ and $AUC_{(0-t)}$ of simvastatin increased 10% and 25%, respectively on co-administration with 10-nitro-9(E)-octadec-9-enoic acid (FIG. 33). Mean $C_{max}$ and $AUC_{(0-t)}$ of simvastatin hydroxyl acid increased 2.5-fold and 2.25-fold, respectively on co-administration with 10-nitro-9(E)-octadec-9-enoic acid (FIG. 33). Based on the mean differences in $C_{max}$ or AUC between subjects dosed alone (pravastatin or Vytorin®) and in combination with 10-nitro-9(E)-octadec-9-enoic acid, a possible drug interaction can be inferred with the simvastatin component of Vytorin. Furthermore, the point estimate decrease in $C_{max}$ and $AUC_{(0-t)}$ described above and in FIG. 33, infers that 10-nitro-9(E)-octadec-9-enoic acid had induced the activity of the post-translational modulator Nrf2 in humans and would therefore be expected to have a beneficial impact on unhealthy humans in need of Nrf2 activation such as those suffering from, for example, solid organ fibrosis, inflammatory disease, cardiovascular disease, renal disease, kidney failure, ischemic kidney injury, acute kidney injury (AKI), chronic kidney injury (CKI), chronic kidney disease (CKD), obesity associated chronic kidney disease, diabetic nephropathy, kidney fibrosis, focal segmental glomerulosclerosis (FSGS), including primary FSGS, and secondary FSGS, sickle cell nephropathy, glomerulonephritis (with and without nephrotic syndrome), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases.

A paired t-test was used to evaluate if the mean of the ln-transformed PK parameters ($C_{max}$, $AUC_{(0-t)}$ and $AUC_{(0-inf)}$) were different between the days the concomitant administered drugs (pravastatin or Vyotrin®) were administered and after co-administration with the 10-nitro-9(E)-octadec-9-enoic acid (FIG. 33). Pravastatin and ezetimibe did not appear to show clinically significant interactions, as point estimates for PK parameters were generally approximately 75 to 100 (95% CI). However, simvastatin hydroxy acid showed a greater than two fold increase and demonstrated statistical significance suggesting that there is a decrease in OATP1B1 transporter activity to account for the increased plasma concentrations of this active metabolite.

Example 5: Predicted Therapeutic Dose/Exposure Range for 10-Nitro-9(E)-Octadec-9-Enoic Acid in Humans A pharmacometrician integrated animal model pharmacokinetic with 10-nitro-9(E)-octadec-9-enoic acid specific pharmacokinetic data obtained from the oral toxicology studies to develop an appropriate pharmacokinetic model and estimate exposures for humans based on assumptions derived from animal data. The model was then updated as pharmacokinetic results became available from an Oral First in Human (FIH) Study, and doses and exposures were re-estimated. From this exposure response model, Cmax and Cave concentrations were determined over the dosing interval in humans (once daily). Based on these data, oral doses of 25, 150, and 600 mg once daily were chosen for the Multiple Ascending Dose Study (Example 3) to provide a broad range of exposures covering anticipated effective concentrations, ranging from 1.0 to 9.0 ng/mL (~3-30 nM). It was predicted that there would be 1 effect at 25 mg daily, and efficacy would be likely evident at 150 mg daily based on translation from animal to human exposures. Subsequently, efficacy in the Multiple Ascending Dose Study (Example 3) was evaluated at these doses based on changes in serum protein biomarkers indicative of the downstream activity of the 10-nitro-9(E)-octadec-9-enoic acid pharmacological actions (specifically, leptin, MCP-1, IL-6, serum triglyceride and cholesterol levels).

PKPD modeling of pharmacologically relevant biomarker data from the Multiple Ascending Dose Study (Example 3) was conducted, and based on this modeling, the most effective dose was determined to be 150 mg once daily; however, there is variability around this estimate. Thus in the subsequent study, Example 4, further confirmation of the dose of 150 mg once daily was sought.

Supporting data from study of Example 4, designed to evaluate the effects of therapeutic dose of 10-nitro-9(E)-octadec-9-enoic acid on transporters known to be affected by Nrf2 activation, did indeed demonstrate that 150 mg of 10-nitro-9(E)-octadec-9-enoic acid daily affected the plasma concentrations of pravastatin and simvastatin whose metabolism is through these transporters. Thus, this study confirmed the activity of 10-nitro-9(E)-octadec-9-enoic acid on Nrf2 activation at 150 mg consistent with the results of the MAD Study (Example 3) and predictions from animal to human translation PKPD modeling.

Because 10-nitro-9(E)-octadec-9-enoic acid is a signaling agent with hormetic properties, it was thought prudent to confirm the dose response in patients with the targeted chronic active disease process. Thus, three doses for the Three Month Open Label Randomized Study of Two Titration Regimens of 10-nitro-9(E)-octadec-9-enoic acid in Patients with Nephrotic Syndrome due to Primary Focal Segmental Glomerulosclerosis (FSGS, Example 6), 75, 150, and 300 mg once daily, were chosen based on the results to date. The pharmacokinetic levels at these doses in humans will be within the range of concentrations at which 10-nitro-9(E)-octadec-9-enoic acid has consistently shown pharmacodynamic activity based on animal and human data and appropriate modeling. The study in FSGS (Example 6) has a novel design to confirm the effective dose (or doses) in patients with this orphan disease.

Example 6: Three Month Open Label Randomized Study of Two Titration Regimens of 10-Nitro-9(E)-Octadec-9-Enoic Acid in Patients with Nephrotic Syndrome Due to Primary Focal Segmental Glomerulosclerosis (FSGS)

One primary objective of this study is to characterize the reduction in proteinuria as measured by urinary protein:creatinine ratio (Up/c ratio) from baseline to end of treatment (3 months). Another objective is to determine the safety profile of patients treated with 10-nitro-9(E)-octadec-9-enoic acid for three months.

Secondary objectives are: to characterize the changes in serological markers of nephrotic syndrome: serum albumin, triglyceride and total cholesterol concentrations, in patients at 3 months of dosing compared to baseline; to evaluate 10-nitro-9(E)-octadec-9-enoic acid dose dependent reduction in proteinuria; to evaluate the effect of 3 months of treatment with 10-nitro-9(E)-octadec-9-enoic acid on Patient Reported Outcomes (using a standardized instrument for FSGS); to evaluate effect of 10-nitro-9(E)-octadec-9-enoic acid on systolic and diastolic blood pressure; to evaluate the changes from baseline in serum and urinary biomarkers of disease activity in patients treated with 10-nitro-9(E)-octadec-9-enoic acid at end of treatment; to evaluate the change in renal function (estimated glomerular filtration rate, eGFR, and serum creatinine) from baseline in patients treated with 10-nitro-9(E)-octadec-9-enoic acid; to evaluate the single and multi-dose pharmacokinetics of 10-nitro-9(E)-octadec-9-enoic acid (±major metabolites) in FSGS patients at various levels of eGFR; and to evaluate PKPD relationships, as data permit.

This is an open label, randomized study of two dose titration regimens of 10-nitro-9(E)-octadec-9-enoic acid. To determine subject eligibility for enrollment in the study, screening assessments will be performed within approximately 6 weeks (42 days) prior to the first dose of study drug. Eligible subjects will enter the baseline phase of the study Day −14 up to day 1 to establish baseline parameters, including but not limited to: multiple urinary protein/creatinine ratios on spot urine collections (First void Specimens) from which a mean baseline value will be calculated, measurements of blood pressure, and other serum and urinary measurements as indicated. Thereafter, subjects will be randomized to one of two dose titration regimens: Group 1: 75 mg/day 10-nitro-9(E)-octadec-9-enoic acid with possible titration to 150 mg/day, or Group 2: 150 mg/day 10-nitro-9(E)-octadec-9-enoic acid with possible titration to 300 mg/day. Each group will consist of up to 12 subjects. Subjects will be dosed for 2 weeks at the first level of the dose titration, either 75 (Group 1) or 150 mg (Group 2) 10-nitro-9(E)-octadec-9-enoic acid once daily at which time a limited battery of laboratory tests of pertinent pharmacology biomarkers will be obtained and evaluated. Dose titration upwards to the next dose of the titration regimen, either 150 mg (Group 1) or 300 mg (Group 2) daily, in each subject will be determined on the basis of these laboratory data according to a predetermined set of guidelines. Dosing will continue until conclusion at 3 months. No dose adjustment will be undertaken during this period of dosing unless the subject is intolerant of the highest dose due to side effects, in which case, reduction of the dose may be allowed to the lower dose in that regimen. All subjects will receive their initial dose of study drug on day 1. Sequential measures of urinary protein/creatinine ratios, renal function (serum creatinine and eGFR), serum and urine biomarkers of 10-nitro-9(E)-octadec-9-enoic acid target engagement, clinical safety (including body weight), PROs and collection of PK samples will be assessed throughout the study (FIG. 34) and will provide data on the magnitude and time course of associated drug effects in subjects with FSGS. PK sampling will be conducted on all subjects throughout the course of the study. The timing of the PK sampling in relation to dosing will be documented. The study design is detailed in FIG. 35.

Safety evaluations of particular interest will be loose stools/diarrhea, body weight, hematological parameters (particularly absolute lymphocyte counts), development of myalgias, and elevated serum CPK, magnesium, creatinine and liver function tests due to these effects having been observed with other drugs that have some overlapping pharmacological actions.

Proteinuria is highly variable, even over short periods of observation. In order to establish a well-defined baseline and to assess variability with a subject, multiple measurements of Up/c will be conducted at baseline, at interim time points, and at 3 months of dosing, and at one month of follow-up.

All renal biopsies will be reviewed by a single renal pathologist well recognized for expertise in histopathological evaluation of FSGS and its subtypes prior to enrollment.

The clinical history of each enrolled subject will be reviewed by a single nephrologist well versed in FSGS and its various causes to ensure compliance with the inclusion/exclusion criteria.

The primary endpoint for this trial will be mean reduction in proteinuria compared to baseline. Reduction in proteinuria will also be assessed by the proportion of subjects achieving the following degrees of reduction (responder analysis): 25% reduction in Up/c; 50% reduction in Up/c; 75% reduction in Up/c; Partial remission (PR): ≥50% decline in Up/c ratio from baseline to a level ≤3 g protein/g creatinine; Complete remission (CR): A decline from baseline Up/c ratio to a level <0.3 g protein/g creatinine.

In addition, changes in serum albumin, triglyceride and cholesterol as well as Patient Reported Outcomes will be evaluated.

Adverse event profile, body weight, systolic and diastolic blood pressure, 12-lead ECGs, clinical laboratory assessments and vital signs will be conducted as part of the safety evaluation. Blood pressure will also be evaluated for safety and for changes compared to baseline using digital monitors. Medications use and all changes in that usage will be recorded during the course of the study.

For 10-nitro-9(E)-octadec-9-enoic acid parent and metabolite(s): $C_{max}$, $AUC_{0-t}$, $AUC_{0-inf}$, $t_{max}$, $t_{1/2}$, $t_{lag}$, CL/F, Vd/F, $\lambda_z$. Other PK parameters may be calculated, as appropriate. Plasma samples for complete PK profile will be collected on Day 1 prior to dosing and after dosing. Sparse plasma samplings will be collected throughout the rest of the study, and analyzed appropriately as the data permit, as per protocol Changes in serological measures of nephrotic syndrome including lipids (total, LDL, and HDL cholesterol and triglycerides, etc) and albumin will be evaluated from baseline to end of dosing and at one month after completion of dosing. Serum creatinine and eGFR will be evaluated at baseline, over the course of the study and at the end of dosing and at one month after completion of dosing. Other serum and urine biomarkers (leptin, fasting blood glucose insulin ratios, MCP-1 etc.) will undergo evaluation from baseline to end of dosing at 3 months and at follow-up, as data permit.

PK/PD effects on various FSGS parameters and biomarkers, as the data permit and as is appropriate.

In addition to the formal evaluation of efficacy, exploratory analyses will be performed to the extent the data allow. This analysis may include additional covariates (e.g., FSGS variant, baseline urinary proteinuria, baseline serum creatinine, APOL-1 status, etc., as appropriate.). Additional details will be specified in a separate statistical analysis plan (SAP).

The power of this study is dependent on the anticipated remission rates in the absence of therapy. In a review of FSGS in adults, Korbet describes spontaneous remission rates of <5%. Furthermore, improvement over time in the absence of an effective treatment is entirely unanticipated. Tumlin et al reported that Up/c ratios increased by 9% in placebo treated steroid resistant patients after 4 months of treatment. For this reason, a statistically significant mean improvement over time will be attributed to treatment regimen, despite being confounded with time.

What is claimed is:

1. A method of treating focal segmental glomerular sclerosis (FSGS), comprising:
    administering to a human patient with FSGS an oral daily dose of 10-nitro-9(E)-octadec-9-enoic acid in an amount greater than 25 mg and less than 450 mg per day.

2. The method of claim 1, wherein the oral daily dose is 75-300 mg.

3. The method of claim 2, wherein the oral daily dose is 150 mg.

4. The method of claim 1, wherein the oral daily dose is a single undivided dose.

5. The method of claim 1, wherein the patient has primary FSGS.

6. The method of claim 5, wherein the patient has primary FSGS with nephrotic syndrome.

* * * * *